(12) United States Patent
Rezaie et al.

(10) Patent No.: US 11,992,699 B2
(45) Date of Patent: *May 28, 2024

(54) INTERNAL ULTRAVIOLET THERAPY

(71) Applicant: CEDARS-SINAI MEDICAL CENTER, Los Angeles, CA (US)

(72) Inventors: Ali Rezaie, West Hollywood, CA (US); Mark Pimentel, Los Angeles, CA (US); Gil Y. Melmed, Los Angeles, CA (US); Ruchi Mathur, Los Angeles, CA (US); Gabriela Guimaraes Sousa Leite, Porter Ranch, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/693,855

(22) Filed: Mar. 14, 2022

(65) Prior Publication Data

US 2023/0035292 A1 Feb. 2, 2023

Related U.S. Application Data

(63) Continuation of application No. 17/507,343, filed on Oct. 21, 2021, now Pat. No. 11,318,325, which is a
(Continued)

(51) Int. Cl.
*A61N 5/06* (2006.01)

(52) U.S. Cl.
CPC ......... *A61N 5/0624* (2013.01); *A61N 5/0603* (2013.01); *A61N 2005/0604* (2013.01);
(Continued)

(58) Field of Classification Search
CPC ............... A61N 5/0624; A61N 5/0603; A61N 2005/0604; A61N 2005/0651;
(Continued)

(56) References Cited

U.S. PATENT DOCUMENTS

| 5,053,033 A | 10/1991 | Clarke |
| 5,573,531 A | 11/1996 | Gregory |

(Continued)

FOREIGN PATENT DOCUMENTS

| AU | 2017273699 A1 | 12/2018 |
| CA | 2515304 A1 | 2/2004 |

(Continued)

OTHER PUBLICATIONS

Extended European Search Report for EP 20877251.7 dated Jan. 21, 2022, 6 pages.
(Continued)

*Primary Examiner* — Jonathan T Kuo
(74) *Attorney, Agent, or Firm* — Nixon Peabody LLP

(57) ABSTRACT

A UV light delivery device for performing intra-corporeal ultraviolet therapy is provided. The device includes an elongated body separated by a proximal end and a distal end. The device also includes a UV light source configured to be received at the receiving space. In some examples, the UV light source is configured to emit light with wavelengths with significant intensity between 320 nm and 410 nm and is utilized in conjunction with an endotracheal tube or a nasopharyngeal airway.

22 Claims, 44 Drawing Sheets

Related U.S. Application Data continuation of application No. 16/992,893, filed on Aug. 13, 2020, now Pat. No. 11,179,575.

(60) Provisional application No. 63/012,727, filed on Apr. 20, 2020, provisional application No. 62/915,448, filed on Oct. 15, 2019.

(52) U.S. Cl.
CPC .............. *A61N 2005/0651* (2013.01); *A61N 2005/0661* (2013.01)

(58) Field of Classification Search
CPC .... A61N 2005/0661; A61N 2005/0608; A61N 2005/0609; A61N 2005/061; A61N 2005/0611; A61N 5/06–2005/073
See application file for complete search history.

(56) References Cited

U.S. PATENT DOCUMENTS

| | | | |
|---|---|---|---|
| 5,855,203 A | 1/1999 | Matter | |
| 6,316,872 B1 | 11/2001 | Ge et al. | |
| 7,311,722 B2 * | 12/2007 | Larsen | A61N 5/062 606/9 |
| 7,409,954 B2 | 8/2008 | Dobkine et al. | |
| 9,023,092 B2 | 5/2015 | Natale et al. | |
| 9,820,798 B2 * | 11/2017 | Schwartz | A61B 18/06 |
| 10,004,918 B2 | 6/2018 | Klang | |
| 10,357,661 B2 * | 7/2019 | Hellstrom | A61B 1/0605 |
| 10,842,567 B2 * | 11/2020 | Grace | A61B 18/26 |
| 11,179,575 B2 * | 11/2021 | Rezaie | A61N 5/0603 |
| 11,318,325 B2 * | 5/2022 | Rezaie | A61N 5/0603 |
| 2002/0120358 A1 | 8/2002 | Lalonde | |
| 2004/0232359 A1 | 11/2004 | Fiset | |
| 2005/0070759 A1 | 3/2005 | Armstrong | |
| 2005/0075703 A1 * | 4/2005 | Larsen | A61N 1/40 607/88 |
| 2005/0107853 A1 | 5/2005 | Krespi et al. | |
| 2006/0069314 A1 | 3/2006 | Farr | |
| 2006/0130846 A1 | 6/2006 | Rife | |
| 2006/0047329 A1 | 7/2006 | Krespi et al. | |
| 2006/0167531 A1 | 7/2006 | Gertner et al. | |
| 2006/0183987 A1 | 8/2006 | Murray | |
| 2006/0217787 A1 | 9/2006 | Olson | |
| 2007/0135874 A1 | 6/2007 | Bala | |
| 2008/0073565 A1 | 3/2008 | Jeon | |
| 2008/0159908 A1 | 7/2008 | Redmond | |
| 2008/0194973 A1 | 8/2008 | Imam | |
| 2008/0257355 A1 | 10/2008 | Rao et al. | |
| 2009/0179547 A1 | 7/2009 | Auday | |
| 2009/0216177 A1 | 8/2009 | Akiyama et al. | |
| 2009/0287137 A1 | 11/2009 | Crowley | |
| 2010/0220472 A1 | 9/2010 | Dahm | |
| 2010/0241198 A1 | 9/2010 | Klepper | |
| 2011/0081323 A1 | 4/2011 | Kleinsek et al. | |
| 2011/0084275 A1 | 4/2011 | Yamamuro et al. | |
| 2011/0226966 A1 | 9/2011 | Takahashi et al. | |
| 2012/0004710 A1 | 1/2012 | Kerber | |
| 2012/0321509 A1 | 12/2012 | Bak | |
| 2013/0104884 A1 | 5/2013 | Vazales | |
| 2013/0261368 A1 * | 10/2013 | Schwartz | A61B 18/06 607/2 |
| 2013/0274549 A1 | 10/2013 | Natale et al. | |
| 2014/0150782 A1 | 6/2014 | Vazales | |
| 2014/0235942 A1 * | 8/2014 | Hellstrom | A61B 1/0615 128/200.26 |
| 2015/0209457 A1 | 7/2015 | Bonutti et al. | |
| 2016/0002277 A1 | 1/2016 | Sichtnik | |
| 2016/0008624 A1 | 1/2016 | Grossman | |
| 2016/0038621 A1 | 2/2016 | Victor et al. | |
| 2016/0114185 A1 | 4/2016 | Mankin | |
| 2016/0128767 A1 * | 5/2016 | Azamian | A61B 18/1492 606/41 |
| 2017/0265942 A1 * | 9/2017 | Grace | A61B 18/245 |
| 2017/0281966 A1 | 10/2017 | Basiony | |
| 2019/0168023 A1 | 6/2019 | Eltorai | |
| 2019/0175938 A1 | 6/2019 | Rezaie et al. | |
| 2020/0346032 A1 | 11/2020 | Rezaie et al. | |
| 2020/0384016 A1 | 12/2020 | Molloy et al. | |
| 2021/0030811 A1 | 2/2021 | Kim et al. | |
| 2021/0106844 A1 | 4/2021 | Rezaie et al. | |
| 2022/0040497 A1 | 2/2022 | Rezaie | |
| 2023/0147752 A1 | 5/2023 | Rezaie et al. | |
| 2023/0302292 A1 | 9/2023 | Rezaie et al. | |
| 2024/0024697 A1 | 1/2024 | Rezaie et al. | |

FOREIGN PATENT DOCUMENTS

| | | |
|---|---|---|
| CA | 3024711 A1 | 12/2017 |
| CN | 1646191 A | 7/2005 |
| CN | 109414591 A | 3/2019 |
| EP | 3463570 A1 | 4/2019 |
| EP | 3893993 A1 | 10/2021 |
| HK | 40001485 A | 2/2020 |
| IN | 201827043869 A | 10/2019 |
| JP | 2000285854 A | 10/2000 |
| JP | 2007511279 A | 5/2007 |
| JP | 2008528188 A | 7/2008 |
| JP | 2009-505365 A1 | 2/2009 |
| JP | 2011530327 A | 12/2011 |
| JP | 2014-233712 A | 12/2014 |
| JP | 2019517305 A | 6/2019 |
| KR | 20190015357 A | 2/2019 |
| MX | 2018014694 A | 5/2019 |
| NZ | 748479 A | 10/2021 |
| SG | 11201810515 T | 12/2018 |
| WO | 2010/029292 A1 | 3/2010 |
| WO | 2010058607 A1 | 5/2010 |
| WO | 2011083381 A1 | 7/2011 |
| WO | 2014022867 | 2/2014 |
| WO | 2014165854 A1 | 10/2014 |
| WO | 2017/210366 A1 | 12/2017 |
| WO | 2021076399 A1 | 4/2021 |
| WO | 2021189020 A1 | 9/2021 |
| WO | 2022036263 A1 | 3/2022 |
| WO | 2022235966 A1 | 11/2022 |

OTHER PUBLICATIONS

JP Notice of Reasons for Rejection for JP2018-562598 dated Jul. 7, 2022, 5 pages.
IPRP for PCT/US20/054758 dated Apr. 19, 2022, 9 pages.
ISR-WO for PCT/US2021/046011 dated Nov. 17, 2021, 10 pages.
Pekmezovic et al., Candida pathogens induce protective mitochondria-associated type I interferon signalling and a damage-driven response in vaginal epithelial cells, Nature Microbiology, 2021, pp. 643-657.
International Search Report and Written Opinion for PCT/US2017/035316 dated Oct. 2, 2017, 12 pages.
European Supplementary Search Report for EP17807445.6 dated Feb. 26, 2020, 14 pages.
Extended European Search Report or EP17807445.6 dated Jun. 25, 2020, 13 pages.
ISR and WO for PCT/US20/054758 dated Jan. 11, 2021, 9 pages.
JP Notice of Reasons for Rejection for JP2018-562598 dated Nov. 2, 2020, 16 pages.
NZ Examination Report for App No. 748479 dated Oct. 14, 2020, 5 pages.
NZ Examination Report for App No. 748479 dated Mar. 24, 2021, 4 pages.
Hamamoto et al., New water disinfection system using UVA light-emitting diodes, Journal of Applied Microbiology, Aug. 30, 2007, vol. 103:6: 2291-2298.
Aihara, et al., Vegetable surface Sterilization system using UVA Light-Emitting Diodes, Journal of Medical Invesstigation, Sep. 27, 2014, vol. 61, pp. 285-290.
SG Written Opinion for 11201810515T dated Mar. 2, 2020, 4 pages.
SG Written Opinion for 11201810515T dated Jan. 20, 2021, 7 pages.

(56) References Cited

OTHER PUBLICATIONS

Wikipedia, Inverse-square law, 2021; https://en.wikipedia.org/wiki/inverse-square_law#Light_and_other_electromagnetic_radiation (Year: 2021).

ISR-WO for PCT/US2021/023354 dated Jun. 30, 2021, 9 pages.

European Centre for Disease Prevention and Control, Outbreak of severe acute respiratory syndrome coronavirus 2 (SARS-COV-2): increased transmission beyond China—fourth update, Feb. 14, 2020 [retrieved May 26, 2021], retrieved from the internet: <URL: https://www.ecdc.europa.eu/sites/default/files/documents/SARS-CoV-2-risk-assessment-14-feb-2020.pdf>, pp. 1-12.

International Search Report and Written Opinion for PCR.US2022/027915 dated Aug. 3, 2022, 12 pages.

Rezaie et al., Ultraviolet A light effectively reduces bacteria and viruses including coronavirus, PLOS One, 2020, vol. 15(8), pp. 1-19.

El Maadidi et al., A NovelMitochondrial MAVS/Caspase-8 Platform Links RNA Virus-Induced Innate Antiviral Signaling to Bax/Bak-Independent Apoptosis, The Journal of Immunology, 2014, vol. 192, pp. 1171-1183.

Leite et al., Ultraviolet-A light increases mitochondrial anti-viral signaling protein in confluent human tracheal cells via cell-cell signaling, Journal of Photochemistry & Photobiology, 2021, vol. 226, pp. 1-7.

Rezaie et al., Endotracheal application of ultraviolet a light in critically ill severe acute respiratory syndrome coronavirus-2 patients: A first-in-human study, retrieved from the internet https://doi.org/10.1101/2021.03.05.21252997, Mar. 8, 2021, pp. 1-19.

Fu et al., SARS-CoV-2 membrane glycoprotein M antagonizes the MAVS-mediated innate antiviral response, Cellular & Molecular Immunology, 2021, vol. 18, pp. 613-620.

Ren et al., Regulation of MAVS Expression and Signaling Function in the Antiviral Innate Immune Response, Front. Immunol., 2020, vol. 11, pp. 1-12.

\* cited by examiner

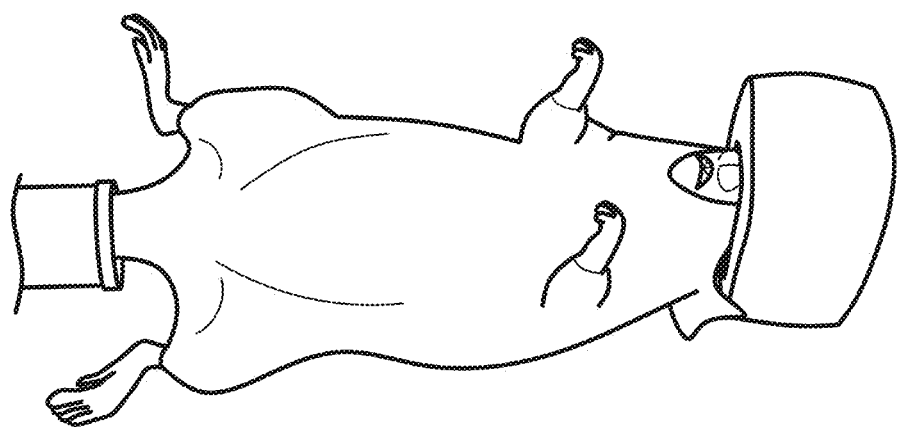
FIG. 13
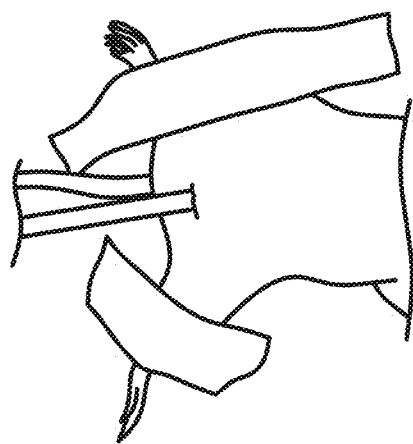 
FIG. 14A FIG. 14B

| Microbial strains | Liquid broth | Solid medium (agar-based plates) | Temperature of incubation °C | Atmosphere | Time of incubation Initial (hour) | Time of incubation Prior UVA exposure (hour) | Intensity of UVA light (µW/cm²) | Time of UVA exposure (minutes) |
|---|---|---|---|---|---|---|---|---|
| Candida albicans (Robin) Berkhout ATCC® 10231™ | Sabouraud Dextrose | Sabouraud Dextrose | 24 to 26 | Aerobic | 16 to 24 | 4 to 6 | 1700 | 20, 40 and 60 |
| Clostridioides difficile (Prevot) Lawson et al. ATCC® 700057™ | Brain Heart Infusion | Reinforced Clostridial | 36 to 37 | Anaerobic | 24 to 48 | 6 to 8 | 2000 | 20, 40 and 60 |
| Enterococcus faecalis ATCC® 29212™ | Brain Heart Infusion | Trypticase Soy Agar with 5% Sheep Blood | 36 to 37 | Aerobic | 18 to 24 | 4 to 6 | 2400 | 20, 40 and 60 |
| Escherichia coli GFP ATCC® 25922 GFP™ | Luria Bertani | Luria Bertani | 36 to 37 | Aerobic | 16 to 24 | 2 to 3 | 1300 | 20, 40 and 60 |
| Escherichia coli - clinical isolate | Luria Bertani | Luria Bertani | 36 to 37 | Aerobic | 16 to 24 | 2 to 3 | 1100 to 1300 | 20, 40, 60 and 80 |
| Klebsiella pneumoniae ATCC® BAA-1705™ | Luria Bertani | Luria Bertani | 36 to 37 | Aerobic | 16 to 24 | 2 to 3 | 1300 | 20, 40 and 60 |
| Proteus mirabilis ATCC® 29906™ | Luria Bertani | Hectoen Enteric | 36 to 37 | Aerobic | 16 to 24 | 2 to 3 | 2400 | 20, 40 and 60 |
| Pseudomonas aeruginosa ATCC® 15442™ | Luria Bertani | Luria Bertani | 36 to 37 | Aerobic | 16 to 24 | 2 to 3 | 3500 | 20, 40 and 60 |
| Staphylococcus epidermidis (Winslow and Winslow) Evans ATCC® 14990™ | Tryptic Soy Broth | Trypticase Soy Agar with 5% Sheep Blood | 36 to 37 | Aerobic | 24 to 48 | 3 to 5 | 2150 | 20, 40 and 60 |
| Streptococcus pyogenes Rosenbach ATCC® 19615™ | Tryptic Soy Broth | Trypticase Soy Agar with 5% Sheep Blood | 36 to 37 | Anaerobic | 24 to 48 | 3 to 5 | 1800 | 20, 40 and 60 |

Fig. 32

| Microorganism | UVA Intensity (µW/cm²) | Group | Baseline CFUx10⁷/mL | 20 min CFUx10⁷/mL | P value | 40 min CFUx10⁷/mL | P value | 60 min CFUx10⁷/mL | P value |
|---|---|---|---|---|---|---|---|---|---|
| Clostridioides difficile | 2,000 | Exposed | 0.1 | 0.08 | 0.01 | 0.01 | 0.003 | 0.0031 | 0.01 |
|  |  | Control | 0.1 | 0.13 |  | 0.17 |  | 0.39 |  |
| Candida albicans | 1,700 | Exposed | 0.14 | 0.09 | 0.007 | 0.03 | 0.001 | 0.0032 | 0.001 |
|  |  | Control | 0.14 | 0.17 |  | 0.2 |  | 0.16 |  |
| Pseudomonas aeruginosa | 3,500 | Exposed | 0.81 | 0.07 | <0.001 | No growth | <0.001 | No growth | <0.001 |
|  |  | Control | 0.81 | 0.61 |  | 0.93 |  | 0.85 |  |
| Klebsiella pneumoniae | 1,300 | Exposed | 5.9 | 6.34 | 0.17 | 3.34 | <0.001 | 1.53 | <0.001 |
|  |  | Control | 5.9 | 7.49 |  | 10.5 |  | 13.81 |  |
| Escherichia coli | 1,300 | Exposed | 1.25 | 0.41 | <0.001 | 0.21 | 0.001 | 0.03 | <0.001 |
|  |  | Control | 1.25 | 3.31 |  | 4.2 |  | 5.52 |  |
| Enterococcus faecalis | 2,400 | Exposed | 9.21 | 2.99 | 0.1 | 0.61 | 0.01 | 0.08 | 0.01 |
|  |  | Control | 9.21 | 10.6 |  | 14.72 |  | 17.74 |  |
| Streptococcus pyogenes | 1,800 | Exposed | 1.17 | 0.68 | 0.64 | 0.64 | 0.001 | 0.17 | 0.004 |
|  |  | Control | 1.17 | 0.83 |  | 1.68 |  | 1.31 |  |
| Proteus mirabilis | 2,400 | Exposed | 0.62 | No growth | <0.001 | No growth | <0.001 | No growth | <0.001 |
|  |  | Control | 0.62 | 0.59 |  | 0.49 |  | 0.54 |  |
| Staphylococcus epidermidis | 2,150 | Exposed | 0.57 | 0.43 | 0.01 | 0.03 | <0.001 | 0.000117 | <0.001 |
|  |  | Control | 0.57 | 0.59 |  | 0.69 |  | 0.7 |  |

Fig. 33

INTERNAL ULTRAVIOLET THERAPY

CROSS REFERENCE TO RELATED APPLICATIONS

This application claims the benefit of priority under 35 U.S.C. § 120 as a continuation of U.S. application Ser. No. 17/507,343 filed Oct. 21, 2021, now issued as U.S. Pat. No. 11,318,325, issued on May 3, 2022, which is a continuation of U.S. application Ser. No. 16/992,893 filed Aug. 13, 2020, now issued as U.S. Pat. No. 11,179,575, issued on Nov. 23, 2021. This application also includes a claim of priority under 35 U.S.C. § 119(e) to U.S. provisional patent application No. 62/915,448 filed Oct. 15, 2019, and U.S. provisional patent application No. 63/012,727 filed Apr. 20, 2020, the contents of which are incorporated herein by reference in their entirety.

FIELD OF THE DISCLOSURE

The present invention is directed to systems and methods for intra-corporeal ultraviolet therapy.

BACKGROUND OF THE DISCLOSURE

The following description includes information that may be useful in understanding the present invention. It is not an admission that any of the information provided herein is prior art or relevant to the presently claimed invention, or that any publication specifically or implicitly referenced is prior art.

Infectious diseases, immune-mediated and inflammatory diseases continue to pose a global challenge. Despite significant strides made in the past several decades, treatment of these diseases remains suboptimal. For example, many patients may contract upper respiratory infections and pneumonia when on ventilators, which may result in death. For instance, patients that undergo ventilator treatment are intubated with an endotracheal tube ("ETT") and may acquire an infection though the ventilation system (e.g., may acquire pneumonia). Accordingly, there is a need to reduce the rates of viral, bacterial, and other infections in the respiratory and other somatic systems of patients.

SUMMARY OF THE DISCLOSURE

A UV light delivery system for performing intra-corporeal ultraviolet therapy is provided. The system includes a delivery tube adapted to be positioned inside of an endotracheal (ET) tube, nasopharyngeal airway (NPA) or other similar device; and at least one UV light source inside the delivery tube positioned to delivery UV light outward from the delivery tube, wherein the at least one UV light source is configured to emit wavelengths between 335 nm and 350 nm. The delivery tube may be transparent or partially transparent.

The at least one UV light source may be a string of LED light sources. In some examples, the string of LED light sources may be configured to emit UV light with a peak wavelength of between 335 and 350 nm, or between 338 and 342 nm. The UV light source may be configured to emit light with a threshold intensity sufficient for treating infections between 335 nm and 350 nm.

The UV light source may be configured to delivery UV light along a substantial length of the delivery tube. The delivery tube may be a catheter. The UV light source may be configured to only emit light with an intensity of greater than 10% of its maximum intensity between 335 nm and 350 nm.

The system may also include a delivery tube adapted to be positioned inside of an endotracheal delivery (ET) tube; and at least one UV light source inside the ET delivery tube positioned to emit UV wavelengths outward form the ET delivery tube, wherein the at least one UV light source is configured to emit wavelengths between 335 nm and 350 nm. The UV light source may be configured for intermittent emission. The UV light source may be configured to emit wavelengths comprising at least one of: UV-A and UV-B or only UV-A.

The system may further comprise a power source connected to the UV light source.

The UV light source may be configured to treat infectious agents in the ET Tube and in the larynx.

Also disclosed is a method of treating a patient for an infectious condition inside the patient's body, the method comprising: inserting a delivery tube inside a respiratory patient cavity; and emitting UV-A light in the range of 335-350 nm from a UV light source positioned in the delivery tube to emit UV wavelengths outward from the delivery tube for a threshold duration and a threshold intensity.

The method may include a delivery tube that is a catheter with a string of LED light sources that have a peak wavelength of between 339-346 nm. The respiratory cavity may be the trachea or the nasopharynx.

The infectious condition may be selected from the group consisting of a bacterial infection, a viral infection, a fungal infection, pneumonia, and combinations thereof.

The threshold duration may comprise at least 20 minutes. The threshold intensity may comprise at least 13, 15, or 18 W/m2. The threshold intensity may comprise an intensity of at least 1,100 microWatt/cm$^2$ 1,100 microWatt/cm$^2$, 2,000 microWatt/cm$^2$, or 2,100 microWatt/cm$^2$, 2,200 microWatt/cm$^2$, or 2,300 microWatt/cm$^2$.

The delivery tube may be inserted inside an endotracheal tube. The delivery tube may also be inserted inside an endotracheal tube while suctioning the endotracheal tube.

Additional features and advantages of the disclosure will be set forth in the description that follows, and in part, will be obvious from the description; or can be learned by practice of the principles disclosed herein. The features and advantages of the disclosure can be realized and obtained by means of the instruments and combinations particularly pointed out in the appended claims. These and other features of the disclosure will become fully apparent from the following description and appended claims, or can be learned by the practice of the principles set forth herein.

BRIEF DESCRIPTION OF THE DRAWINGS

In order to describe the manner in which the above-recited disclosure and its advantages and features can be obtained, a more particular description of the principles described above will be rendered by reference to specific examples illustrated in the appended drawings. These drawings depict only example aspects of the disclosure, and are therefore not to be considered as limiting of its scope. These principles are described and explained with additional specificity and detail through the use of the following drawings:

FIG. 13 illustrates an exemplary UV emitting device implemented in the colon of a mouse, in accordance with the principles of the present disclosure;

FIGS. 14A and 14B illustrate an exemplary UV emitting device of the present disclosure inserted into the vaginal canal of a rat, in accordance with the principles of the present disclosure;

FIG. 32 illustrates a table showing the intensities and exposure durations of UVA light applied to bacterial cultures in one example.

FIG. 33 illustrates a table showing bacterial counts over time during UV light exposure in one example.

DETAILED DESCRIPTION

Definitions

Figure 1A:
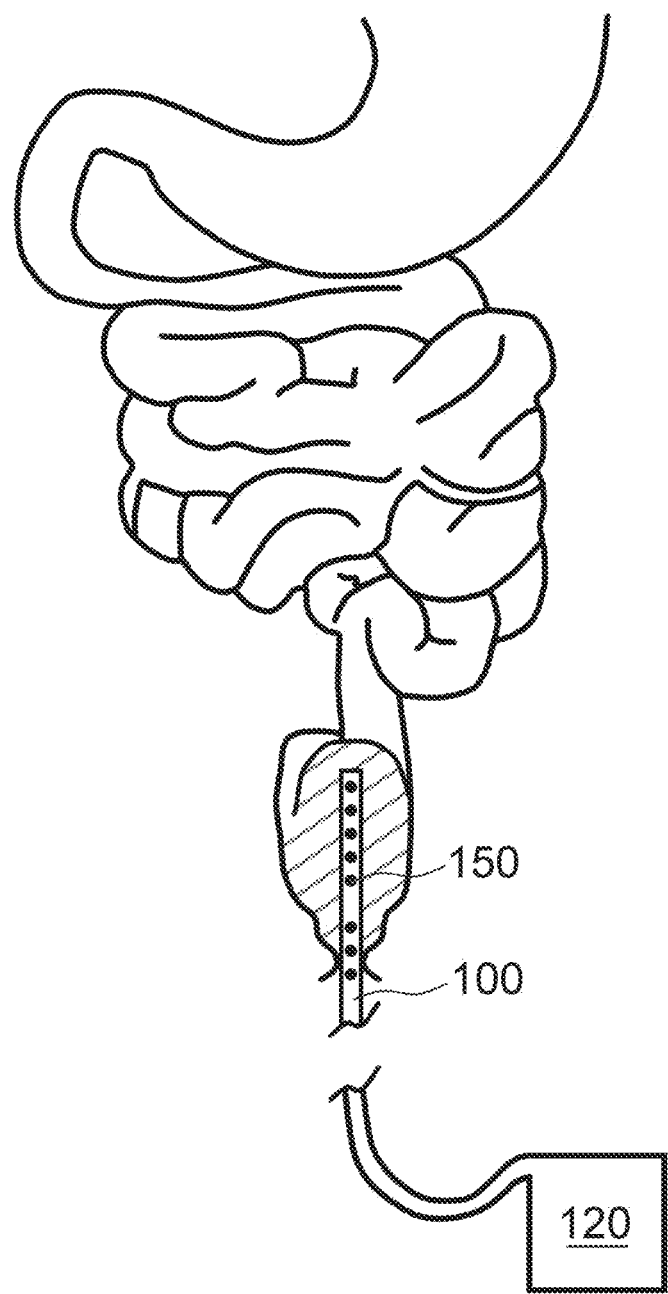
FIG. 1A illustrates a cross sectional view of an exemplary UV emitting device inserted into a colon of a patient, in accordance with the principles of the present disclosure.

Unless defined otherwise, technical and scientific terms used herein have the same meaning as commonly understood by one of ordinary skill in the art to which this invention belongs. Szycher's Dictionary of Medical Devices CRC Press, 1995, may provide useful guidance to many of the terms and phrases used herein. One skilled in the art will recognize many methods and materials similar or equivalent to those described herein, which could be used in the practice of the present invention. Indeed, the present invention is in no way limited to the methods and materials specifically described. For example, the Figures primarily illustrate the present invention in the gastrointestinal tract, but as indicated throughout, the disclosed systems and methods can be used for other applications.

In some embodiments, properties such as dimensions, shapes, relative positions, and so forth, used to describe and claim certain embodiments of the invention are to be understood as being modified by the term "about."

As used herein, "ETT" refers to an endotracheal tube, which is a flexible tube placed through the mouth of a patient into the trachea to assist a patient in breathing while connected to a ventilator.

As used herein, "NPA" refers to a nasopharyngeal airway, which is a flexible tube placed through the nasal passageway and ending at the base of the tongue to assist in maintaining an open airway.

As used herein, the term "LED" refers to a light emitting diode that is a semiconductor light source that emits light across various visible and non-visible light spectrums. LEDs typically have an emission spectrum that includes a set of wavelengths that vary in intensity over their emission spectrum range, and typically follow a bell or similar shaped intensity curve over that wavelength range. Specific LEDs are typically described using their wavelength of peak emission intensity, or the wavelength at which the LED emits its highest intensity of radiation.

Accordingly, LEDs typically emit light across a range of wavelengths, and specific LEDs may also be described using the range of wavelengths it emits over a threshold intensity (in some examples, a percentage of the LEDs maximum intensity). For instance, a given LED may emit light with at least 10% of its maximum emission intensity only between the wavelengths of 335 nm and 345 nm. Below 335 nm and above 345 nm, that LED's intensity of emission may be less than 10% of that LED's peak intensity emission wavelength ("peak wavelength" herein), and in some cases too low to be therapeutically relevant. Therefore, for many treatment applications, only the wavelengths between 335 nm and 345 nm would have an impact on treatment for that specific LED.

Accordingly, the range of wavelengths described herein may be the range of wavelengths that is therapeutically effective or significant for a particular treatment application, duration, and intensity of emission delivered by the LED to the treatment site (or based on power of emission emitted by the LED). In some examples, the range of wavelengths may be the range of wavelengths emitted by the LEDs that have an intensity that is at least 1, 2, 3, 4, 5, 6, 7, 8, 9, 10, 11, 12, 13, 14, 15, 16, 17, 18, 19, or 20% of the peak emission intensity.

Accordingly, disclosed herein are emission spectrum ranges for various LED light sources which correspond to the ranges for which the LED emits a threshold intensity percentage of its maximum intensity. Examples of various LED spectrum emission ranges and peak intensity wavelengths of emission of commercially available LEDs are described in Filippo, et al, "LEDs: Sources and Intrinsically Bandwidth-Limited Detectors," the content of which is incorporated by reference in its entirety.

Various examples of the invention will now be described. The following description provides specific details for a thorough understanding and enabling description of these examples. One skilled in the relevant art will understand, however, that the invention may be practiced without many of these details. Likewise, one skilled in the relevant art will also understand that the invention can include many other obvious features not described in detail herein. Additionally, some well-known structures or functions may not be shown or described in detail below, so as to avoid unnecessarily obscuring the relevant description.

The terminology used below is to be interpreted in its broadest reasonable manner, even though it is being used in conjunction with a detailed description of certain specific examples of the invention. Indeed, certain terms may even be emphasized below; however, any terminology intended to be interpreted in any restricted manner will be overtly and specifically defined as such in this Detailed Description section.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations may be depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Overview

While UV light in the UV-A and UV-B range has traditionally been used to treat dermatologic disorders, it has not been developed for broader infection or inflammation treatment inside the human body. The present disclosure describes a system for emission of therapeutic doses of UV light via a catheter, capsule, endoscope, tube, or port that can be used to manage internal infections and inflammatory conditions inside a patient. The UV light source disclosed herein is intended to provide a safe and effective alternative to antibiotics and anti-inflammatory/immunosuppressant drugs to various internal canals of a patient (e.g. colon, vagina, trachea).

In some examples, only UV-A light or only UV-B light may be emitted for certain indications and treatments. For instance, a UV light source may have wavelengths centered around 335 nm, 340 nm, or 345 nm or nearby ranges as disclosed herein. In other embodiments, the UV light sources may emit wavelengths between 320 nm-410 nm, and/or have a peak intensity of emission within that range. It should be understood that various wavelengths can be provided using the systems and methods. In some examples, the wavelength range provided may be the highest wavelength possible that is therapeutically effective in a certain intensity and duration of application.

FIG. 1A illustrates an example of a UV light administrative system that includes a delivery tube 100 and several UV light sources 150, and a power source 120 to power the system. Accordingly, as illustrated, a caregiver (e.g., physician) can navigate the delivery tube 100 to a colon of a patient. Once navigated to the intended treatment target of the patient, the power source 120 may be energized to emit UV light from the light sources 150 into the therapeutic target (e.g. colon).

Figure 1B:
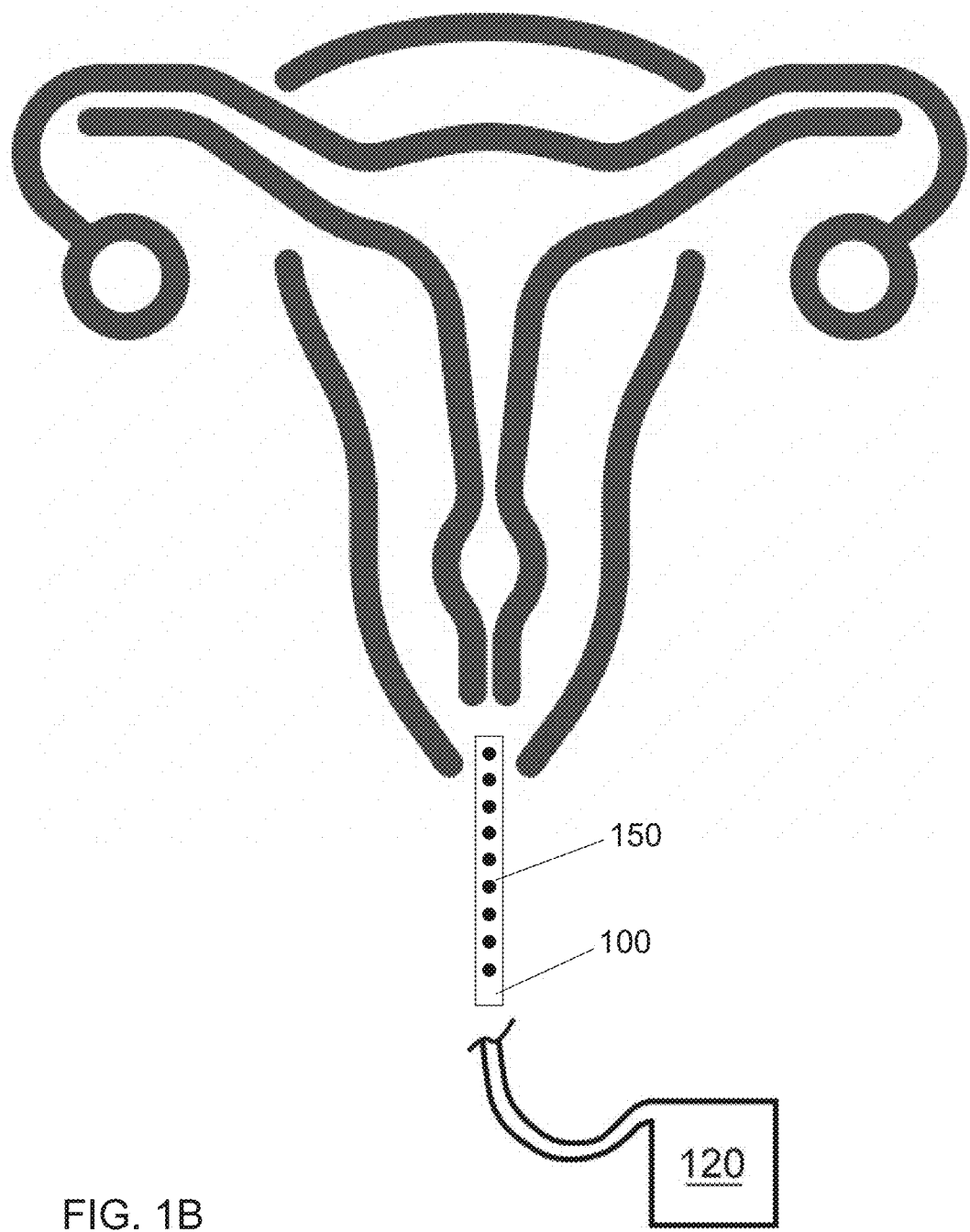
FIG. 1B illustrates a cross sectional view of the exemplary UV emitting device inserted into a vagina of a patient, in accordance with the principles of the present disclosure.

FIG. 1B illustrates an example of a UV light administrative system that includes a delivery tube 100, several UV light sources 150, and a power source 120. Accordingly, a caregiver (e.g., physician) can navigate the delivery tube 100 to a vagina of a patient. Once navigated to the vagina of the patient, the delivery tube 100 can be energized by the power source 120 to emit therapeutic light (e.g., UV light) into the vaginal canal. The UV light source disclosed herein is intended to provide a safe and effective alternative to antibiotics and anti-inflammatory/immunosuppressant drugs to the colon region and/or the vagina region.

Figure 1C:
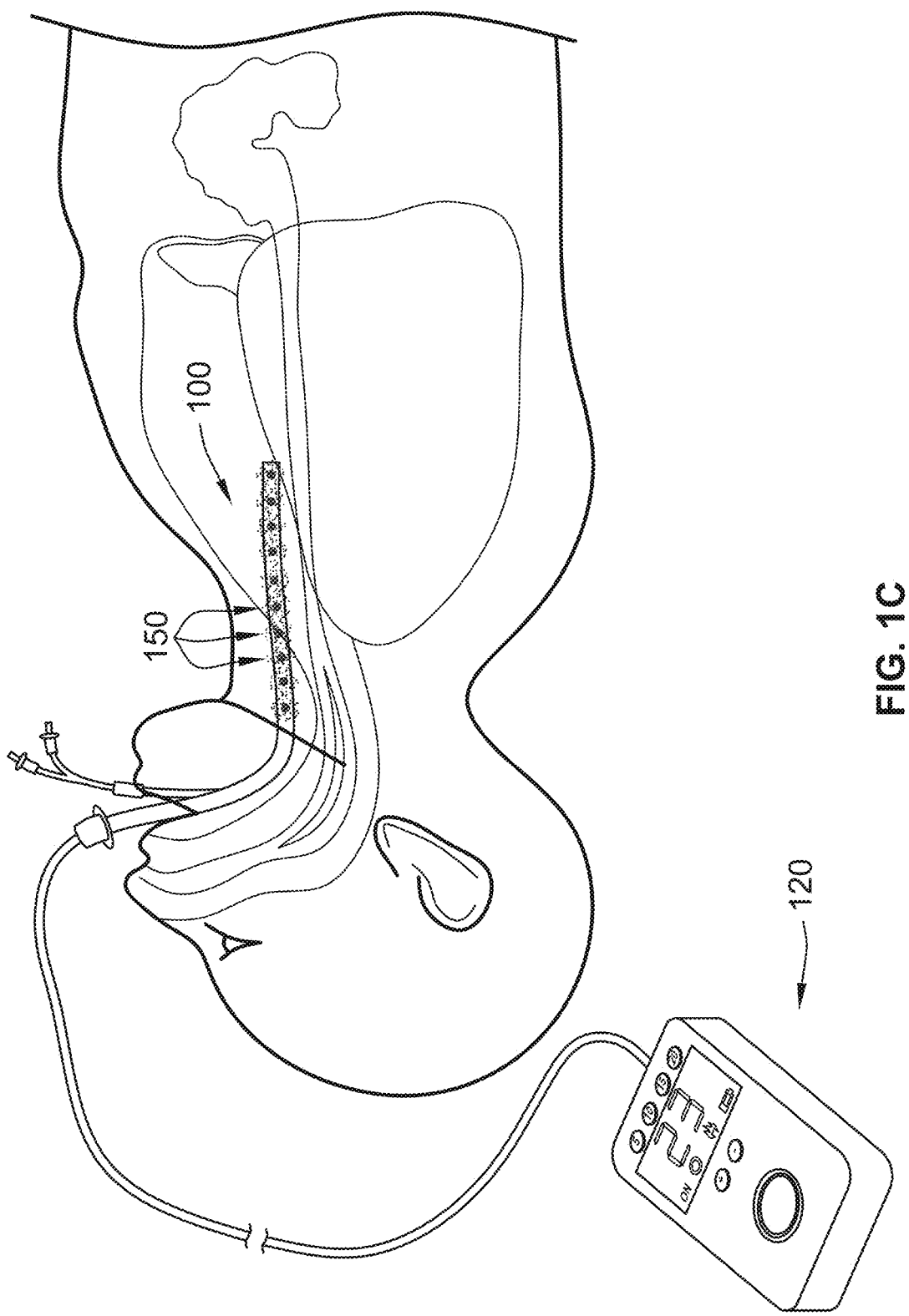
FIG. 1C illustrates a cross sectional view of the exemplary UV emitting device inserted into a trachea of a patient, in accordance with the principles of the present disclosure.

FIG. 1C illustrates an example of a UV light administrative system that includes a delivery tube 100, UV light sources 150, a power source 120, and a control system. The control system provides power and controls the duration and/or intensity of treatment. Accordingly, as illustrated, a caregiver (e.g., physician) can navigate the delivery tube 100 to a trachea of a patient during ventilation. Once navigated to the trachea of the patient, the power source 120 can be energized so that it delivers power to the light sources 150 through the delivery tube 100 (e.g. wired connections) to emit therapeutic light (e.g., UV light) into the trachea and/or other respiratory canals.

For instance, systems and methods have been developed to provide internal ultraviolet therapy in conjunction with an endotracheal tube (ETT) as disclosed herein. Accordingly, the delivery tube 100 may be navigated inside an ETT during ventilation of a patient. In other examples, the delivery tube 100 may be connected to or built into an ETT, or an ETT may have light sources 150 incorporated into the ETT. Accordingly, the light sources 150 may be positioned within the tube 150 and/or ETT so that the UV light sources 150 radiate the respiratory tissue in the tracheal airways surrounding the ETT.

Figure 1D:
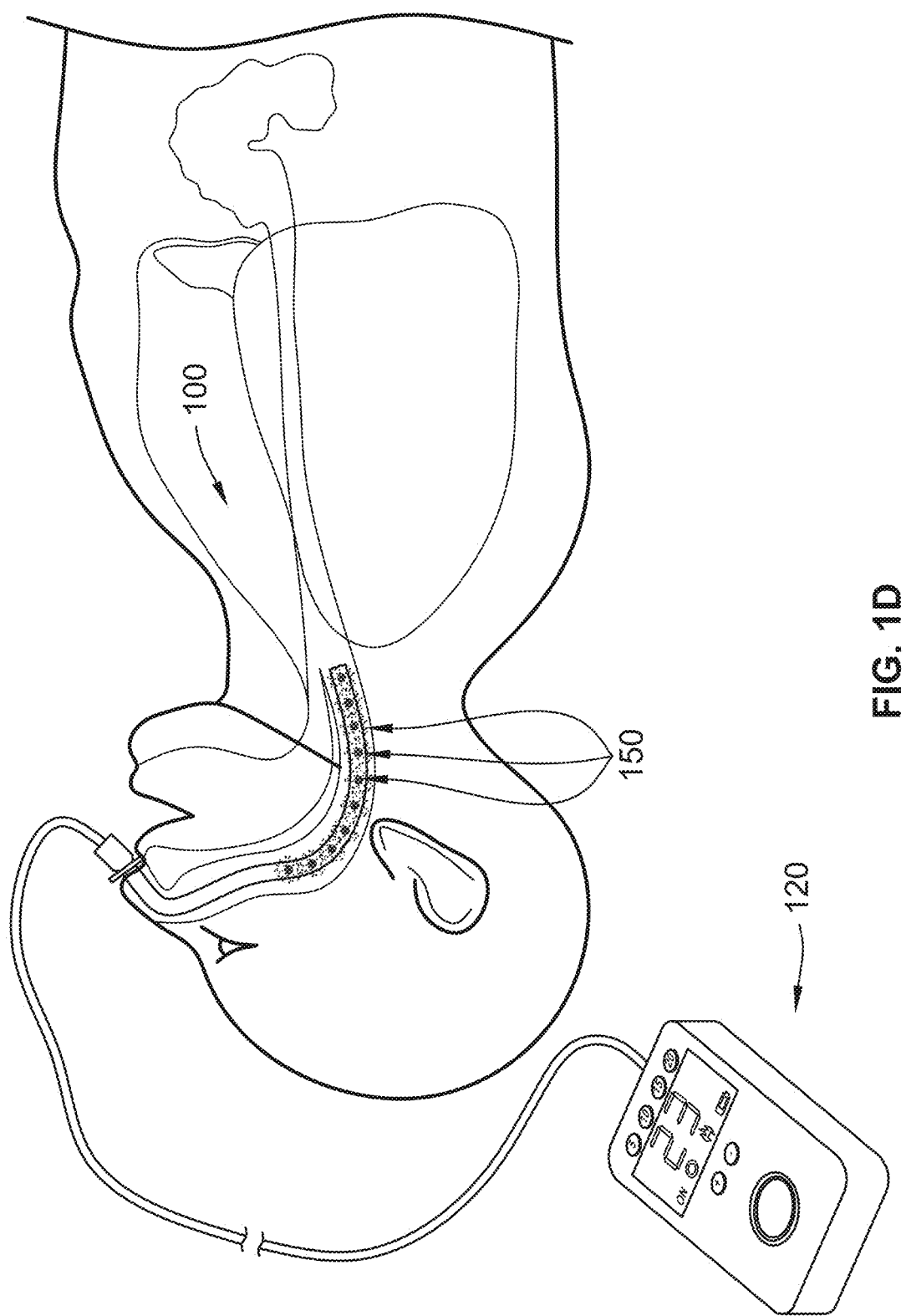
FIG. 1D illustrates a cross sectional view of the exemplary UV emitting device inserted into a nasopharynx of a patient, in accordance with the principles of the present disclosure.

FIG. 1D illustrates an example of a UV light administrative system that includes a delivery tube 100, UV light sources 150, a power source 120, and a control system. The control system provides power and controls the duration and/or intensity of treatment. Accordingly, as illustrated, a caregiver (e.g., physician) can navigate the delivery tube 100 to the nasopharynx of a patient. Once navigated to the nasopharynx of the patient, the power source 120 can be energized so that it delivers power to the light sources 150 through the delivery tube 100 (e.g. wired connections) to emit therapeutic light (e.g., UV light) into the nasopharynx and/or other respiratory canals.

For instance, systems and methods have been developed to provide internal ultraviolet therapy in conjunction with a nasopharynx airway (NPA) as disclosed herein. Accordingly, the delivery tube 100 may be navigated inside an NPA of a patient. In other examples, the delivery tube 100 may be connected to or built into an NPS, or an NPA may have light sources 150 incorporated into the NPA. Accordingly, the light sources 150 may be positioned within the tube 150 and/or NPA so that the UV light sources 150 radiate the respiratory tissue in the nasopharynx surrounding the NPA.

Delivery Systems

A delivery tube/rod 100 for delivering therapeutic UV light to various portions inside a body is provided. The delivery tube/rod can include at least one UV light source 150. The delivery tube/rod 100 can be a catheter, endoscope, capsule (for swallowing or suppository), or any other medical device configured to receive a UV light source 150.

In some examples, the UV delivery tube 100 may be configured as a catheter, and navigated inside of an ETT or an NPA during respiratory or other therapy of a patient. In some embodiments, the UV delivery tube/rod 100 is configured as an endoscope, which is inserted rectally or orally, and navigated to the appropriate regions to deliver anti-inflammatory or other therapeutic doses of UV light. In another embodiment, the UV delivery tube/rod 100 can be configured as a catheter, which is inserted into arteries, urethra, vagina and urinary tract, ear canal, airways etc. In yet another embodiment, the UV delivery tube/rod 100 is configured as an indwelling urinary catheter, which is inserted into a patient's bladder. In some embodiments, an inflatable balloon catheter can include the UV light source 150 to emit UV light inside internal organs with passageways, such as, e.g., the vagina, rectum, gastroesophageal junction, stomach, biliary tract, or other suitable passageways. In some embodiments, the UV light source 150 can be configured as a caregiver's glove. This configuration may assist with emitting UV light into a patient's orifice (e.g., a mouth, a rectum, a vagina, or others) for shorter duration treatments.

In some embodiments, UV light sources 150 are permanently mounted onto the delivery tube/rod 100. In other embodiments, the delivery tube/rod 100 is configured such that the UV light sources 150 are configurable, and able to be mounted and removed at a physician's preference. The delivery tube/rod 100 can include a hollow interior to allow for electrical connections to the UV light sources 150. In alternative embodiments, the UV light sources 150 may be wireless, and able to couple to the delivery tube/rod 100.

Light Sources

Figure 2:
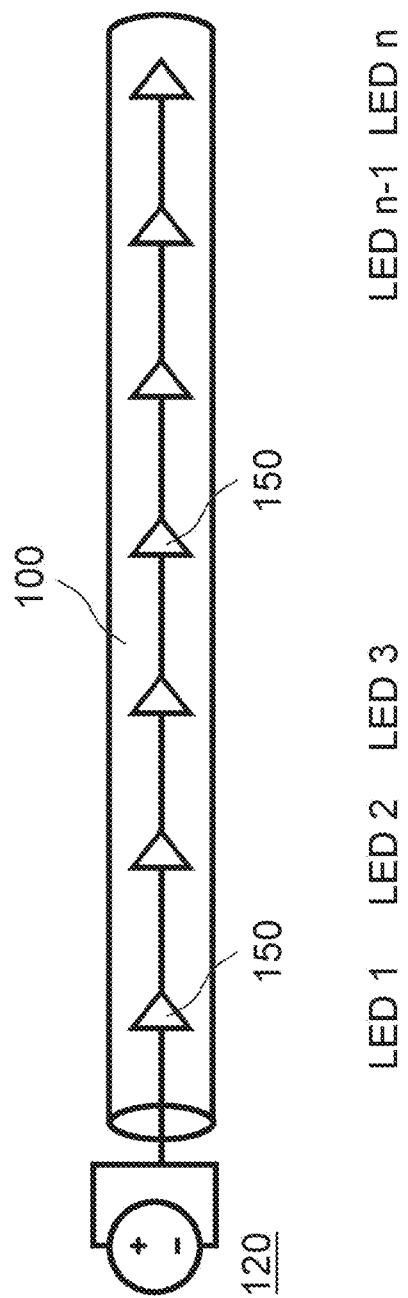
FIG. 2 illustrates a schematic view of an exemplary UV emitting device incorporating LEDs, in accordance with the principles of the present disclosure.

Depending on the delivery tube 100 or other delivery device, various light sources 150 may be utilized that are capable of emitting UV light. For instance, FIG. 2 illustrates an embodiment of a flexible delivery tube 100 (e.g., catheter, endoscope, or the like) that includes a string of LED light sources 150 that are distributed along the tube 100. In other examples, other suitable light sources 150 capable of emitting UV light may be utilized. Each of the light sources 150 are attached together with electrical connections and connected to a power supply 120. LED light sources 150 may be advantageous, since their small size and low power requirements enable them to be placed along the delivery tube 100.

Accordingly, if the light sources 150 are placed along the delivery tube 100, the light sources 150 may deliver a UV light to a large delivery area inside the patient. Accordingly, the therapeutic target area may be relatively large, to treat inflammatory diseases that may affect a large portion of the colon.

Figure 3:
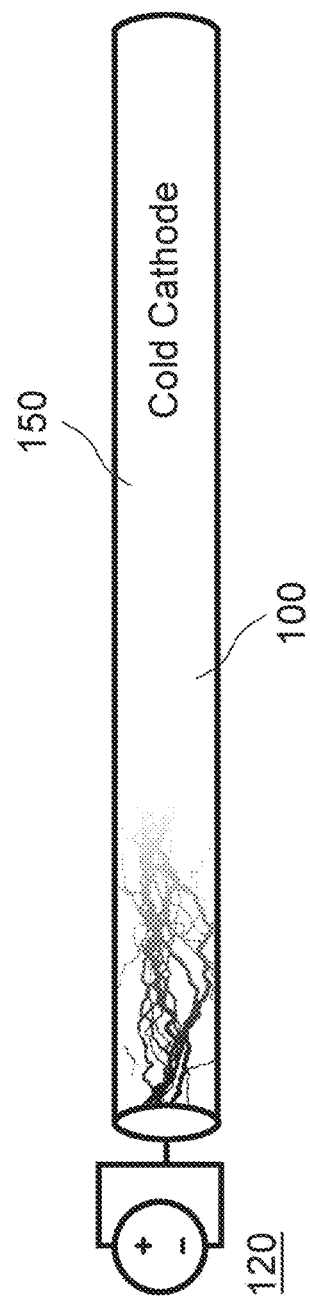
FIG. 3 illustrates a schematic view of an exemplary UV emitting device incorporating a cold cathode, in accordance with the principles of the present disclosure.

FIG. 3 illustrates an example of a delivery tube 100 that utilizes a cold cathode based light source 150 that is connected to a power supply 120. In this embodiment, the cold cathode light source 150 delivers light through a transparent, flexible delivery tube 100. This embodiment may include an inert gas that fills the delivery tube (or a vacuum tube) 100. The delivery tube 100 may include, e.g., a cold cathode tube. The delivery tube 100 may include any cathode light emitter that is not electrically heated by a filament. For instance, a cold cathode fluorescent lamp may utilize a discharge in mercury vapor to emit ultra violet light.

However, in most embodiments, the gases utilized in the tube should be inert for safety. For instance, neon gas vapor may be energized with a 12-volt power supply 120 to generate sufficient UV light. In other examples, other power supplies with various voltages and/or currents will be utilized to develop sufficiently intense light at the current wavelength.

In some embodiments, the light sources 150 may emit x-rays. For these embodiments, the system may include vacuum tubes or x-ray tubes.

The power supply 120 may include an on/off switch or other controls to turn on and off the light sources 150. In some examples, the power supply will include the ability to turn on the UV light source at various intensities, or to modulate the intensity over time depending on the therapeutic application. The power supply may be different for different types of UV light sources 150. For instance, the power requirements for an LED implementation may be less than for a cold cathode implementation.

UV Ranges

Figure 4:
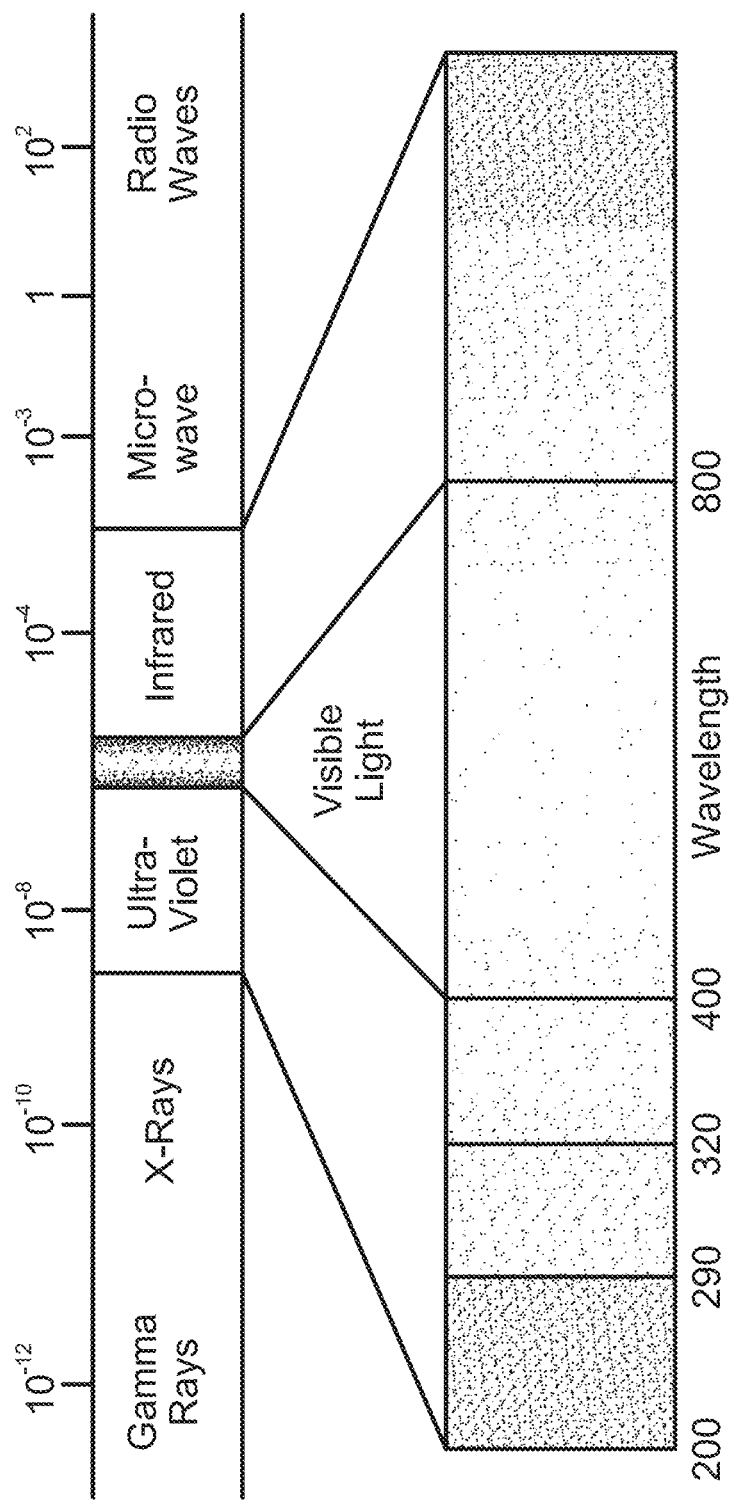
FIG. 4 illustrates an exemplary schematic of the UV spectrum, in accordance with the principles of the present disclosure.

FIG. 4 illustrates UV ranges that may be implemented by the disclosed devices and methods. For instance, the light sources may deliver light only the UV-A and UV-B ranges, and not in the UV-C ranges. In other examples, the systems and methods may deliver light in all three UV ranges, or also deliver light in the visible spectrum. In some examples, only UV-A or only UV-B light may be emitted for certain indications and treatments. As indicated above, a light source may have wavelengths of maximum intensity centered around 335 nm, 340 nm, or 345 nm or nearby ranges. In other embodiments, the light sources 150 may deliver light with wavelengths between 320 nm-410 nm, 250 nm-400 nm or other suitable ranges as discussed herein.

In some examples, the wavelength range applied may be the longest wavelength range that is therapeutically effective for a particular application (given the intensity and duration of treatment application). For instance, the shorter the wavelengths, the more likely treatment will damage body cells or tissues of the patient. Accordingly, the longest wavelength that is effective will be the safest to apply.

In some examples, a light source centered around 345 nm or 340 nm (or surrounding wavelengths), may be optimal, as lower/shorter wavelengths are more harmful as they approach the UV-C range. For instance, the shorter the wavelengths, the more energy they have and more likely they are to damage the tissues and DNA of a patient. In some examples, the longest wavelengths that still provide sufficient antimicrobial impacts, making it the safest wavelength that is still effective, may include one or more of the following: 335, 336, 337, 338, 339, 340, 341, 342, 342, 344, 345, 346, 347, 348, 349, or 350 nm. Accordingly, a light source 150 as disclosed herein may emit light with one or more of the preceding wavelengths at intensities that are therapeutically significant.

In some examples, the light source may be an LED with a peak wavelength of 335 nm, 336 nm, 337 nm, 338 nm, 339 nm, 340 nm, 341 nm, 342 nm, 343 nm, 344 nm, 345 nm, 346 nm, 347 nm, 348 nm, 349 nm, 350 nm, 351 nm, 352 nm, 353 nm 354 nm, 355 nm. In some examples, the peak wavelength of an LED may have a +/−3 nm, 2 nm, or 1 nm error. In some examples, the LEDs may emit light with significant intensity in a range of +/−4, 5, or 6 nm around its peak intensity emission wavelength. Accordingly, in some examples, the wavelength range of the LED or other light source may be from 340-350 nm (for instance, the wavelength range that includes wavelengths with significant intensity of emission).

Treatment Regimens

The procedures herein may be utilized to treat a number of different inflammatory and infectious diseases. Accordingly, different amounts or time period dosages of UV radiation may be administered depending on the following: (1) type of disease, (2) type of light source, (3) light source power, (4) light source UV range, and (5) severity of the infection or inflammation. For instance, in some embodiments, the time of administration will be determined by the capsule digestion rate, and other factors (e.g., light source power, UV range, and the like) can be manipulated to vary the dosage.

In other examples, the light therapy may be delivered by a caregiver for 10 minutes, 15, minutes, 18 minutes, 19 minutes, 20 minutes, 21 minutes, 22 minutes, 23, minutes, 24 minutes, 25 minutes, 26, minutes 27 minutes, 28 minutes, 29 minutes, 30 minutes, 60 minutes, 90 minutes, 120 minutes, or 160 minutes, any range of minutes between 10 and 160 minutes or other suitable times. In addition, methods of the invention can include administering therapy for a threshold duration of at least 10 minutes, 15, minutes, 18 minutes, 19 minutes, 20 minutes, 21 minutes, 22 minutes, 23, minutes, 24 minutes, 25 minutes, 26, minutes 27 minutes, 28 minutes, 29 minutes, 30 minutes, or 60 minutes. The light source intensity may be at least 1,000 microWatt/cm$^2$, 1,100 microWatt/cm$^2$, 2,000 microWatt/cm$^2$, 2,100 microWatt/cm$^2$, 2,200 microWatt/cm$^2$, 2,300 microWatt/cm$^2$, 2,400 microWatt/cm², 2,500 microWatt/cm², 2,600 microWatt/cm², 2,700 microWatt/cm², 2,800 microWatt/cm², 2,900 microWatt/cm², 3,100 microWatt/cm², 3100 microWatt/cm², 3,200 microWatt/cm², 1,000-5,000 microWatt/cm² or other suitable intensities depending on the application and other factors relevant to the treatment effectiveness. The inventors have confirmed that application of UV-A light is safe at intensities of up to 5,000 microWatt/cm². In some examples, the light will be delivered continuously and in other examples it will be incorporated into pulse therapy.

The light source 150 may be various distances from the target based on the intensity and target microbe. For instance, in some examples, the light source 150 may be required to be within 0 to 2 cm from *E. coli* in order to kill the *E. coli* (but not at 2.8 cm or 3.5 cm) using an intensity of 2000 microwatt/cm². In some examples, the intensity may be between 1000-5000 microwatt/cm² and the distance to a target tissue may be between 0-1 cm, 0-1.5 cm, 0-2 cm, 0-2.5 cm, 0-3.0 cm, 0-3.5 cm, 0-4.0 cm, or other similar and suitable ranges based on the intensity of the light and target pathogen. In other examples, the timing, distance, wavelength, and intensity required may be different for viruses and other targets.

EXAMPLES

The following examples are provided to better illustrate the claimed invention and are not intended to be interpreted as limiting the scope of the invention. To the extent that specific materials or steps are mentioned, it is merely for purposes of illustration and is not intended to limit the invention. One skilled in the art may develop equivalent means or reactants without the exercise of inventive capacity and without departing from the scope of the invention.

GI Tract

Figure 5:
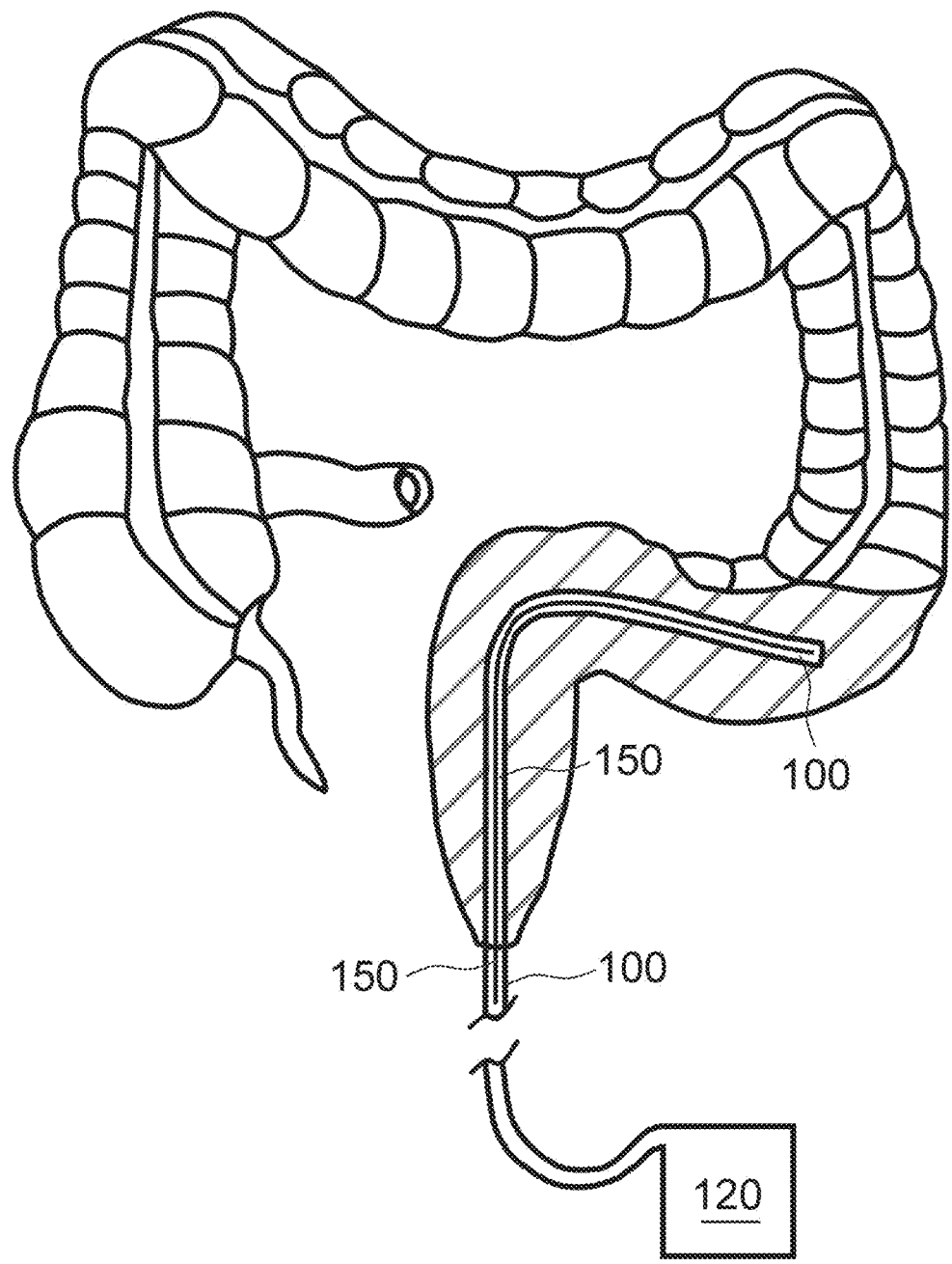
FIG. 5 illustrates a cross sectional view of the exemplary UV emitting device inserted into the rectum and sigmoid of a patient, in accordance with the principles of the present disclosure.
Figure 6:
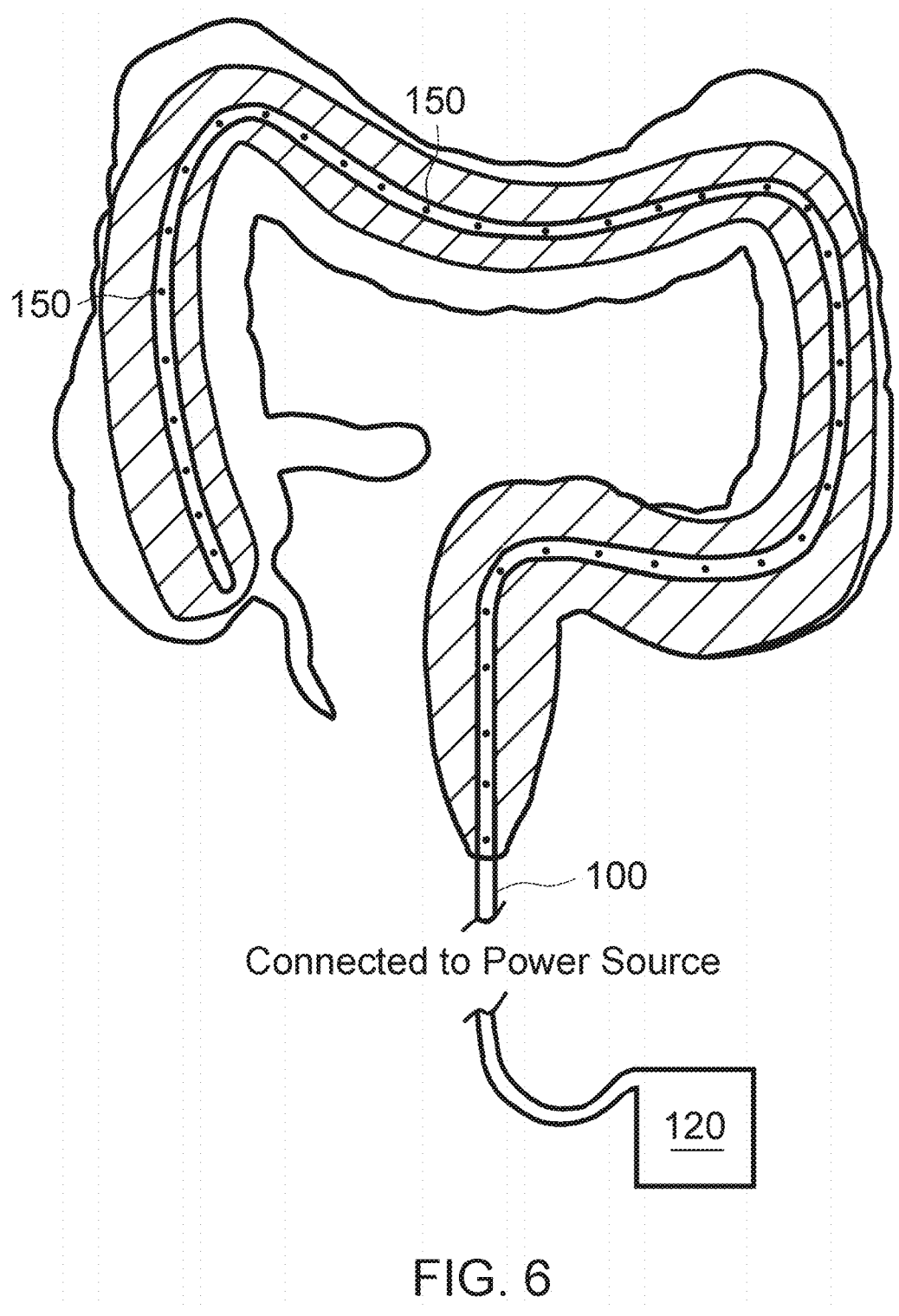
FIG. 6 illustrates a cross sectional view of the exemplary UV emitting device inserted into the colon of a patient, in accordance with the principles of the present disclosure.

FIGS. 5-6 illustrate example applications to treat disorders in the colon and/or rectum. For instance, FIG. 5 illustrates a delivery tube 100 that includes light sources 150 may be inserted by the caregiver into the colon through the anus. Then, the delivery tube 100 may be navigated to the therapeutic site, for instance the colon, a portion or most of the intestines (see, e.g., FIG. 6), or the stomach via mouth (see, e.g., FIG. 7). Then, the power supply (or light source) 120 may be turned on to illuminate the therapeutic site with UV light.

In some examples, this may be utilized to treat various inflammatory diseases including ulcerative and Crohn's colitis, IBD, infectious diseases and others as more fully described herein. As illustrated, depending on the size, location and type of disease, the delivery tube 100 may include varying amounts of light sources 150 that may be embedded or contained in certain portions or lengths of the delivery tube 100.

Figure 7:
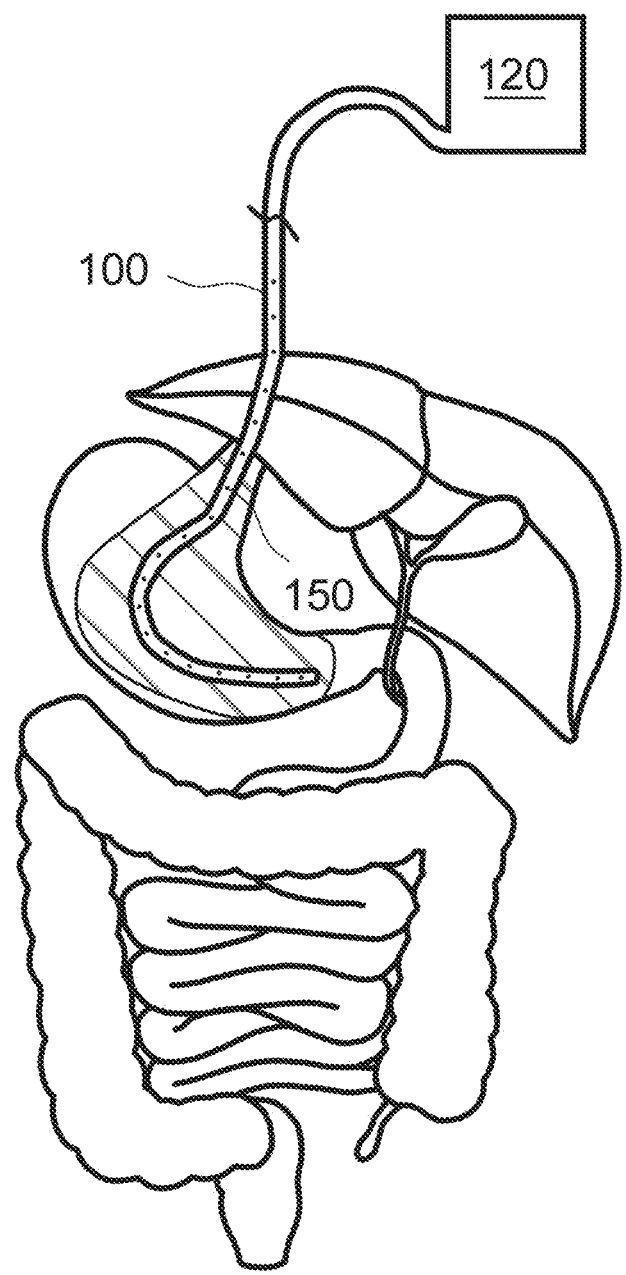
FIG. 7 illustrates a cross sectional view of UV emitting device inserted in the esophagus and stomach of a patient, in accordance with the principles of the present disclosure.

FIG. 7 illustrates an embodiment where an endoscope or other delivery tube 100 is inserted through the oral cavity through the esophagus into the stomach. In this example, an infection or inflammatory disease in the stomach may be treated with the UV light sources 150.

Colonoscopy

FIG. 13 illustrates an example of a UV emitting device being used on a colonoscopy on a mouse. The colonoscopy and UV application was carried out safely. The parameters have included a normal colonoscopy 72 hours after 10 minutes and 30 minutes of UV exposure with 1,100 micoWatt/cm² intensity.

GI treatments may include the following exemplary applications:
1. Treatment of ulcerative colitis and Crohn's disease and acute/chronic pouchitis and other chronic inflammatory bowel diseases (IBD)
2. Treatment of non-IBD related proctitis
3. Treatment of IBD or non-IBD related fistula
4. Treatment of inflammatory strictures
5. Treatment of microscopic colitis
6. Treating infectious diarrhea using UV light emitting capsules
7. Treating refractory *Helicobacter pylori* and MALT lymphoma
8. Treatment of esophageal lichen planus and pemphigus vulgaris
9. Treatment of refractory *Clostridium difficile*
10. Treatment of colonic inertia, tropical sprue, celiac disease, small intestinal bacterial overgrowth, typhlitis post-bone marrow transplant infections, pseudopolyps (similar to nasal polyps) and radiation enteritis
11. Treatment of Barrett's esophagus with or without dysplasia
12. Treatment of hepatic encephalopathy with daily UV light capsule
13. Treatment of blind loop syndrome in Roux-en-Y patients by placing an ILT(Internal light therapy) catheter through a PEG in the remnant stomach
14. Treating perianal fistulas with transparent setons which can emit UV light
15. Decreasing the rate of infection associated with percutaneous feeding or suction tubes
16. Treatment of gastrointestinal cancers limited to mucosa and submucosa
17. Treatment of hepatobiliary infections, inflammation and cancers limited to mucosa and submucosa Capsule In some embodiments, the delivery device is shaped as a capsule instead of a delivery tube/rod 100. In such embodiments, the capsule is inserted into a patient orally or anally. The capsule can emit light for a certain period. For instance, a capsule can include a smooth clear or semi-transparent polymer or other biocompatible coating to allow for passage of the capsule. In some examples, the capsule may include a light source 150 and a power supply 120. The power supply 120 can include, for example, a small battery. In some embodiments, the capsule can be deployed and pinned to an internal organ to provide prolonged light exposure.

In some embodiments, the capsule is configured such that the UV lights 150 are positioned to emit light in all directions from the capsule. Accordingly, as the capsule traverses the digestive system it will emit UV light in all directions until the capsule is excreted.

Figure 8:
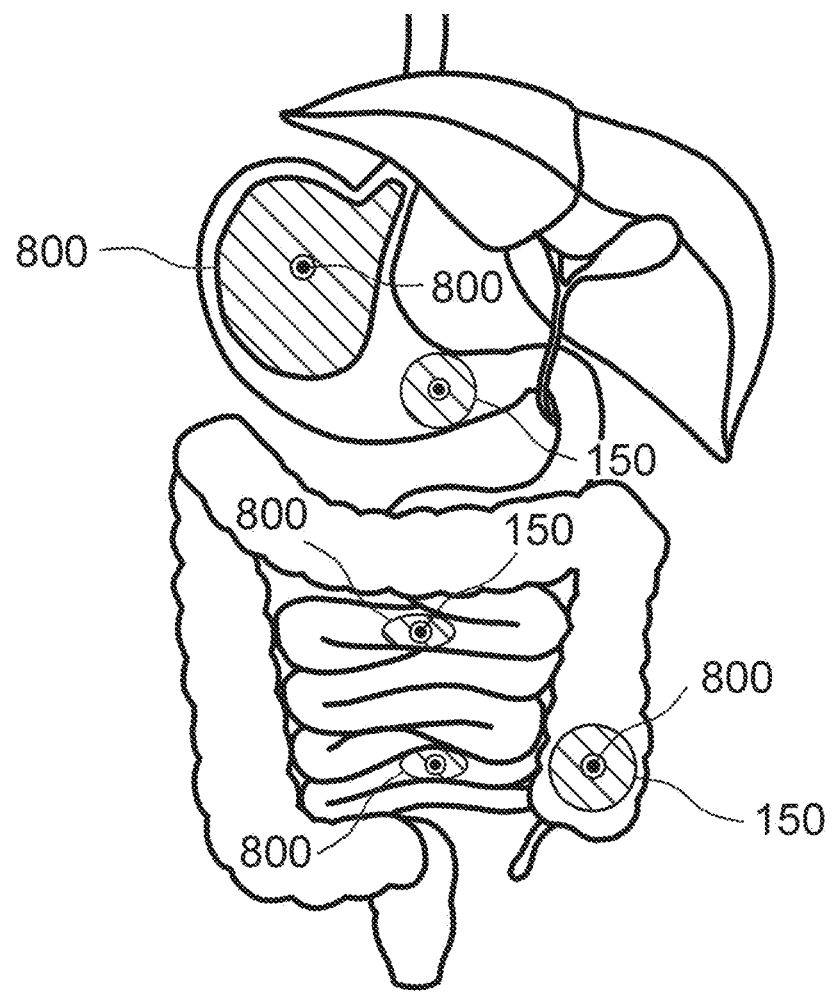
FIG. 8 illustrates a cross sectional view of the exemplary UV emitting devices traversing the digestive system of a patient, in accordance with the principles of the present disclosure.

FIG. 8 illustrates an example of a system that utilized a capsule 800 for a delivery device that may be swallowed by the patient. The capsule 800 may contain a light source 150 and a power supply 120 for powering the light source 150. In some examples the capsule will be made, or portions of it will be made of transparent material to allow the light to radiate through the capsule. A capsule may contain a tracking device to assess the location of the capsule inside the gastrointestinal tract. A capsule delivery system may be clipped in a hollow organ for continuous or intermittent controlled delivery.

In some examples, the capsule may be the size of a pill or smaller, and may be orally ingestible. The capsule may include a timer for turning on and off the UV light source when the capsule reaches or is most likely to reach a certain portion of the digestive tract. For instance, the capsule may contain a simple timer to turn on the capsule after 30 minutes, an hour or two hours. For example, the capsule may not turn on the light source 150 until the capsule has reached the digestive tract to treat IBS or other infectious or inflammatory conditions.

Light Conductive Delivery Tube

In some examples, a light source 150 may be placed inside the delivery tube 100 (e.g. LEDs) and in other examples, a light source 150 may be placed outside or interfacing with a proximal end of a delivery tube 100. Accordingly, in some examples, the delivery tube 100 may be made from fiber optics or other light conductive material to propagate the light from the light source 150 down the delivery tube 100 so that it may be emitted into the treatment site.

Figure 9:
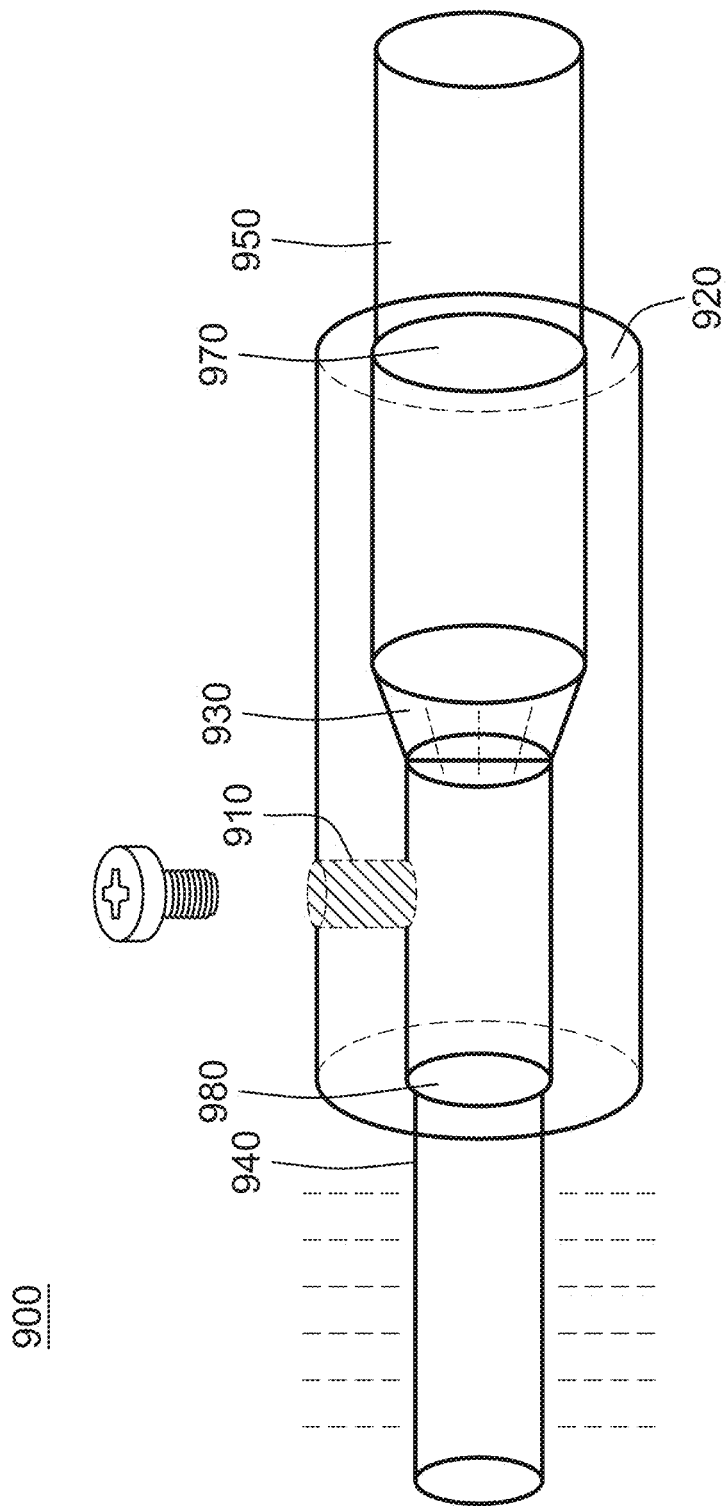
FIG. 9 illustrates a side view of an exemplary light source attachment, in accordance with the principles of the present disclosure.
Figure 10:
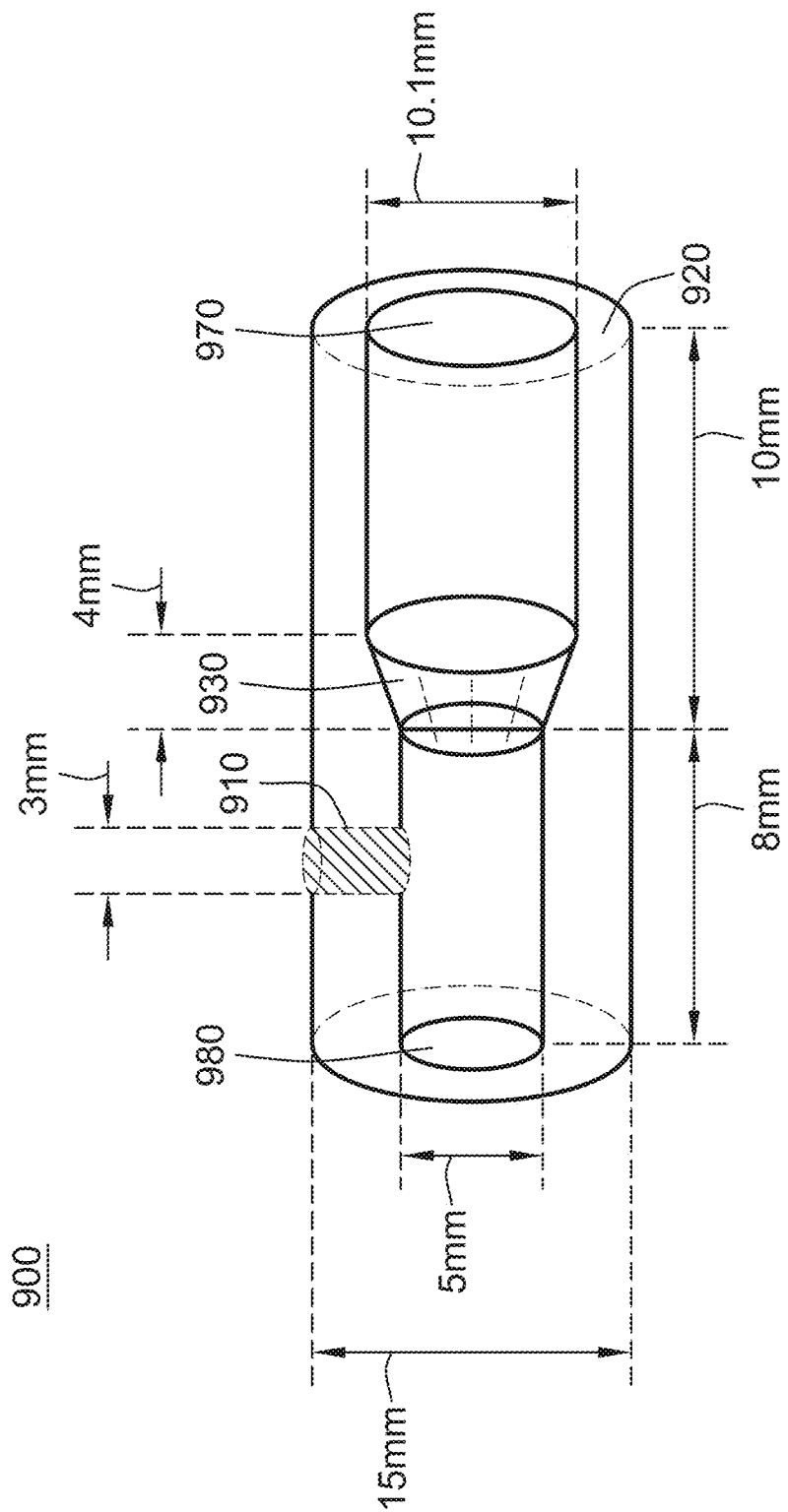
FIG. 10 illustrates a side view of an exemplary light source attachment, in accordance with the principles of the present disclosure.

For instance, as shown in FIGS. 9 and 10, a UV light administrative system may include a delivery rod 940, UV light source 950, and a light source attachment 900, wherein the light source attachment 900 is configured to be attached between the UV light source 950 and the delivery rod 940. The delivery rod 940 may include a borosilicate segment 930 which omits UV-C from the light spectrum followed by a segment made out of pure silica (quartz) 900 to extent transmission distance of UV A/B with minimal loss.

For example, using only a pure quartz segment has shown to result in significant UV-C light emission (e.g., 4,300 microWatt/cm$^2$ UV-C), whereas using pure quartz rod with a short segment of borosilicate in between the UV light source 950 and the delivery rod 940 (e.g., borosilicate filter) results in the same level of detection of UV-A and UV-B without the borosilicate segment and only 10 microwatt/cm$^2$ of UV-C light emitted at the tip of the delivery rod 940, which means that the UV light is reflected back to the body of the delivery rod 940 for a uniform delivery of the UV light throughout the delivery rod 940. The UV light source 950 may be configured to be connected to a power source (not shown) that powers the UV light source 950.

The delivery rod 940 may be a fiber optic rod/catheter. In some example embodiments, the delivery rod 940 is made by scoring using industrial diamond, whereby the glass cutter oil is used and bilateral pressure to snap clearly (rather than opaque) is applied. The tip of the delivery rod 940 may be rounded by a drill (e.g., 500 RPM drill) wherein the drill uses a premium diamond polish pad (e.g., 120-200 grit premium diamond polish pad) and sandpaper (e.g., 400 sandpaper). Afterwards, a body of the delivery rod 940 may be sanded with a 120-200 grit premium diamond polish pad so that the UV-C free light (e.g., UV-A and UV-B) can emit throughout the body of the delivery rod 940. Alternative chemical opacification can be used for custom opacification of the rod.

The light source attachment 900 may include a body 920 and a fastening mechanism 910 (e.g., a screw, a stopper screw, a fastener, a nail, and the like) that attaches the body 920 to an enclosure (e.g., a rod, a catheter, a handle, or the like). The body 920 may include a front-end aperture 970 that is configured to connect to a light source (or power supply) and a back-end aperture 980 that is configured to connect to a rod (or catheter).

The light source attachment 900 may be made of aluminum for heat conduction and for decreasing light intensity deterioration. The diameter of both the front-end aperture 970 and the back-end aperture 980 may vary in order to fit, e.g., a particular catheter, tube, rod, or the like. The light source attachment 900 may also include a convex lens 930 between the front-end aperture 970 and the back-end aperture 980 that is configured to decrease the light loss. The convex lens may include semi-convex heat resistant lens that decreases light loss and focuses the light.

Catheter

In some examples, the delivery device may be a catheter tube 100 that may be insertable into the arteries, urethra or other parts of a patient's body. For instance, the catheter tube 100 may include a hollow portion that allows for a guide wire to pass through. Accordingly, a caregiver may navigate a guide wire to the treatment site and then pass the catheter over the guide wire to navigate the catheter to or beyond the treatment site.

The catheter tube 100, like the endoscope implementation, may then contain any variety of light sources 150 suitable for administering UV treatment to the inside of an artery. In some examples, this implementation may use smaller light sources 150 such as LEDs.

Figure 11:
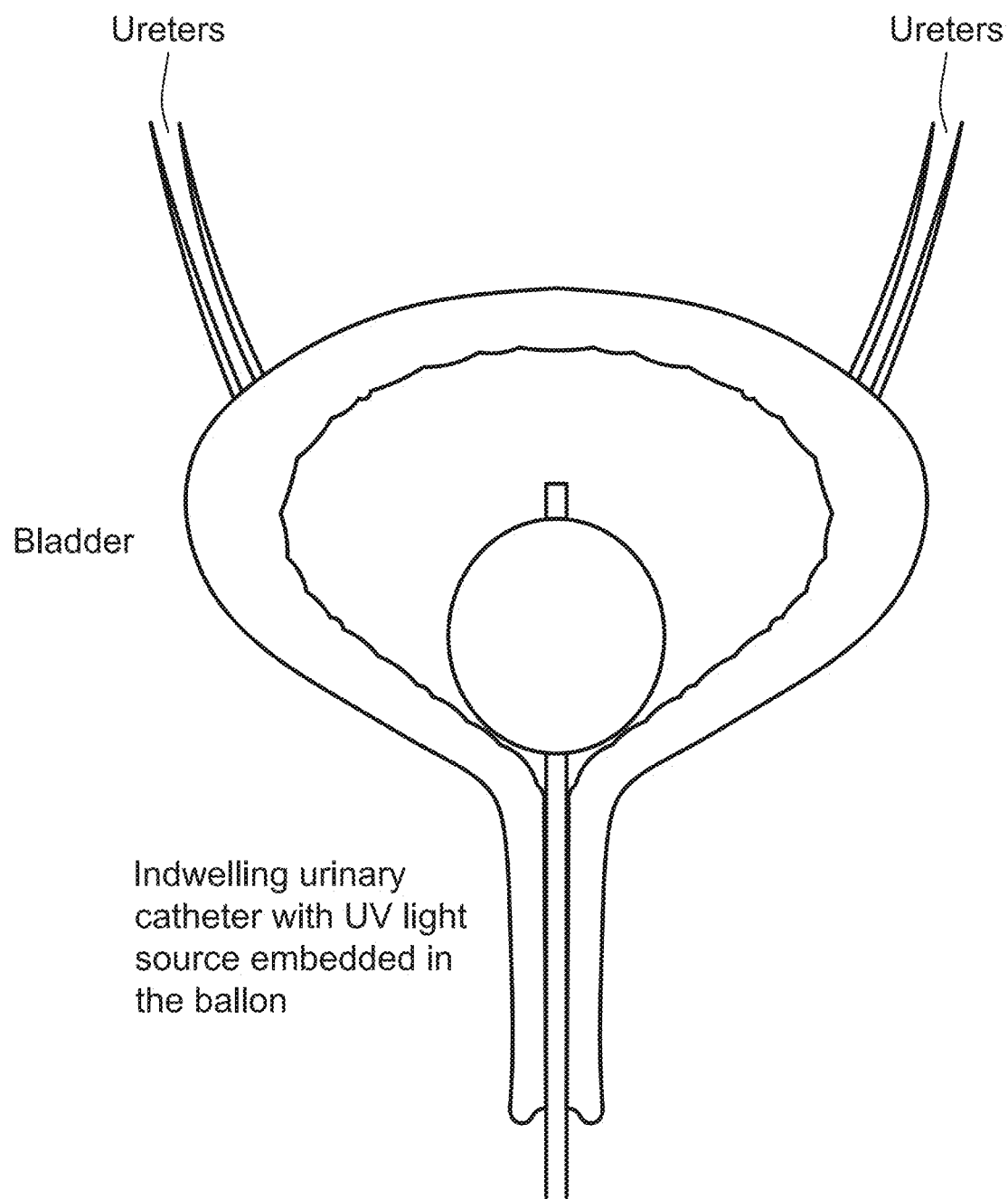
FIG. 11 illustrates an exemplary Foley catheter incorporating the exemplary UV emitting device, in accordance with the principles of the present disclosure.

In another example of the present disclosure, the delivery device may be a catheter tube 100 that may be inserted into a bladder as an indwelling urinary catheter (as shown in, e.g., FIG. 11), so that it disinfects the urinary tract infection with UV lights. In another example, the delivery device may be a part of a balloon inserted into a rectum to treat the rectum with UV lights.

Vaginal

In yet another example, the delivery device may be incorporated into a vaginal rod to treat infection in a patient's vagina.

Figure 22:
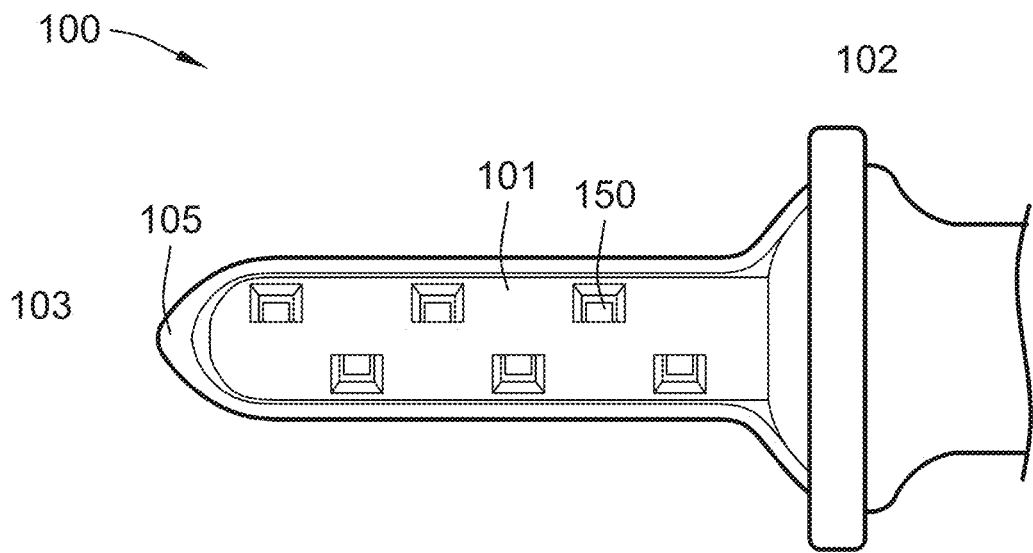
FIG. 22 illustrates an exemplary UV emitting device, in accordance with an embodiment of the present disclosure.

FIG. 22 illustrates an exemplary UV emitting device, in accordance with an embodiment of the present disclosure, that in some examples may be utilized for vaginal delivery of UV light. The UV emitting device can include a delivery tube/rod 100. In some examples, the delivery tube/rod 100 includes a four-sided elongated body 101. The four-sided elongated body 101 can include UV light sources 150 on each of the four sides. The UV light sources 150 can be staggered on each side of the delivery tube/rod 100. The delivery tube/rod 100 can include a proximal end 102 and a distal end 103. The four sides of the elongated body 101 converge into a rounded surface 105 towards the distal end 103. The distal end 103 of the delivery tube/rod 100 is configured for insertion into a patient, as discussed above. In contrast, the opposing proximal end 102 is configured for maneuverability of the delivery tube/rod 100.

Figure 23:
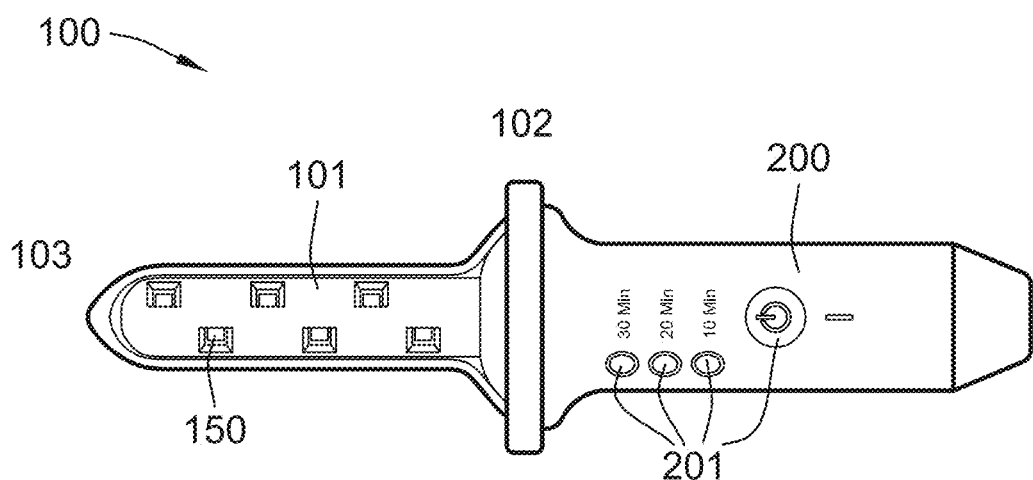
FIG. 23 illustrates the exemplary UV emitting device of FIG. 22 mounted to a gripping element 200, in accordance with an embodiment of the present disclosure.

FIG. 23 illustrates an example of the UV emitting device of FIG. 22 with a gripping element 200. The gripping element 200 can be configured as a handle. The gripping element 200 can be attached to the delivery tube/rod 100 at the proximal end 102. The gripping element 200 can be designed to be ergonomically sufficient for a physician or a medical provider. The gripping element 200 can also include input components 201 configured to receive a user's inputs. The input components 201 can be connected to an internal processor that alters the functionality of the delivery tube/rod 100 and the UV light sources 150. In some embodiments, the delivery tube/rod 100 includes between 2 and 20 UV light sources. The delivery tube/rod 100 illustrated herein includes three UV light sources 150 on each side of the four sides, for a total of twelve (12) UV light sources 150. It should be understood that other configurations are feasible incorporating the features disclosed herein.

Figure 24:
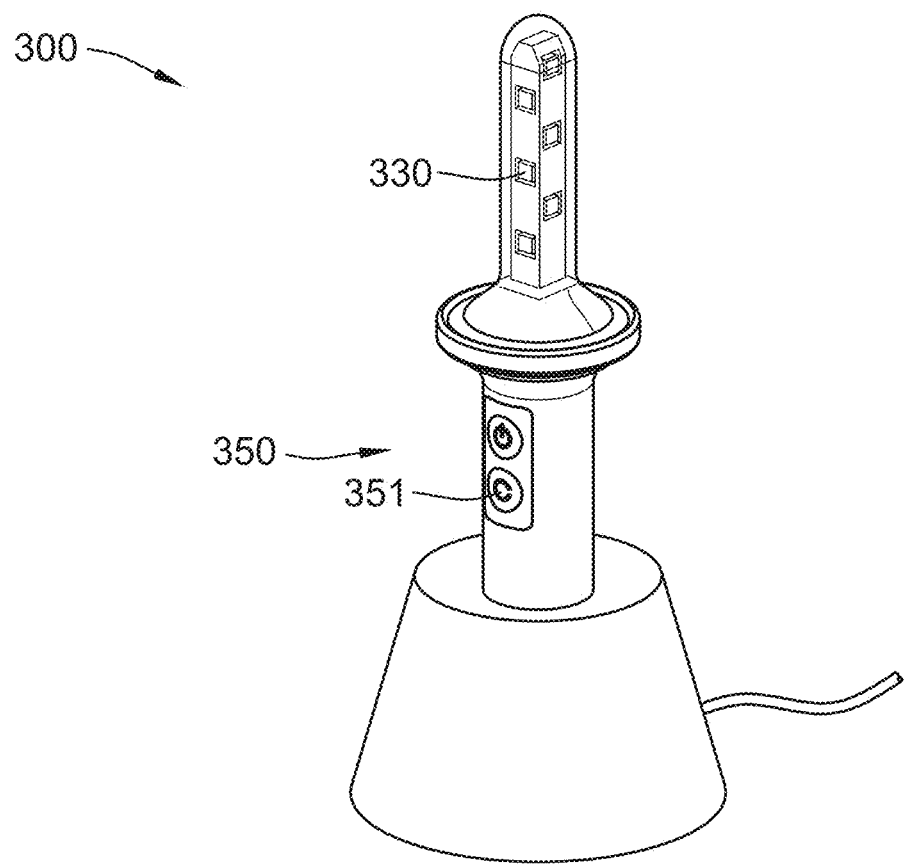
FIG. 24 illustrates an exemplary UV emitting device, in accordance with an embodiment of the present disclosure.

FIG. 24 illustrates an exemplary UV emitting device 300, in accordance with an embodiment of the present disclosure. The UV emitting device 300 can include a gripping element 350. The gripping element 350 can be designed to be ergonomically sufficient for a physician or a medical provider. The gripping element 350 can also include input components 351 configured to receive a user's inputs. The input components 351 can be connected to an internal processor that alters the functionality of the delivery tube/rod 300 and the UV light sources 330. The delivery tube/rod 300 illustrated herein includes two UV light sources 330 on each side of the four sides, for a total of eight (8) UV light sources 330. It should be understood that other configurations are feasible incorporating the features disclosed herein.

In some embodiments, the delivery tube/rod 100 can include a rotating base at its distal end 103. The rotating base can enable rotation of the delivery tube/rod 100 such that light emitted from the UV light sources 150 is uniform. When treating a patient with a rotating delivery tube/rod 100 the uniform UV emittance is likely to assist in treating microbial growth. In some examples, the delivery tube/rod 100 also includes a stepper motor. The stepper motor is able to enable the rotation of the rotating base.

In some embodiments, the UV light sources 150 are distributed along the entire length of the delivery tube/rod 100, and at the distal end 103 to achieve a broader application of the UV light source 150.

In some embodiments, the delivery tube/rod 100 is configured such that the entire delivery tube/rod 100 glows and transmits UV light homogenously. In some embodiments, the delivery tube/rod 100 is configured to emit light waves in the UV-A and/or UV-B ranges only, and not in the UV-C range. For example, a peak wavelength of the UV light sources 150 can include 340 nm. In other broader embodiments, the delivery tube/rod 100 (and the light sources 150) can deliver wavelengths between 320 nm-410 nm. It should be understood that various wavelengths and various combination of wavelengths can be provided using the disclosed delivery tube/rod 100. Other range wavelengths can include, for example, 250 nm-400 nm. In some embodiments, the vertical illuminated length extends between 8-10 cm around the delivery tube/rod 100.

Figure 25:
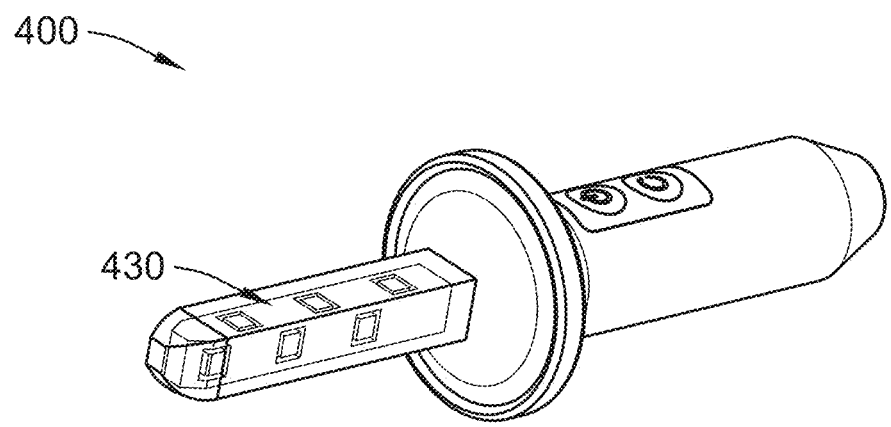
FIG. 25 illustrates an exemplary UV emitting device, in accordance with an embodiment of the present disclosure.
Figure 26:
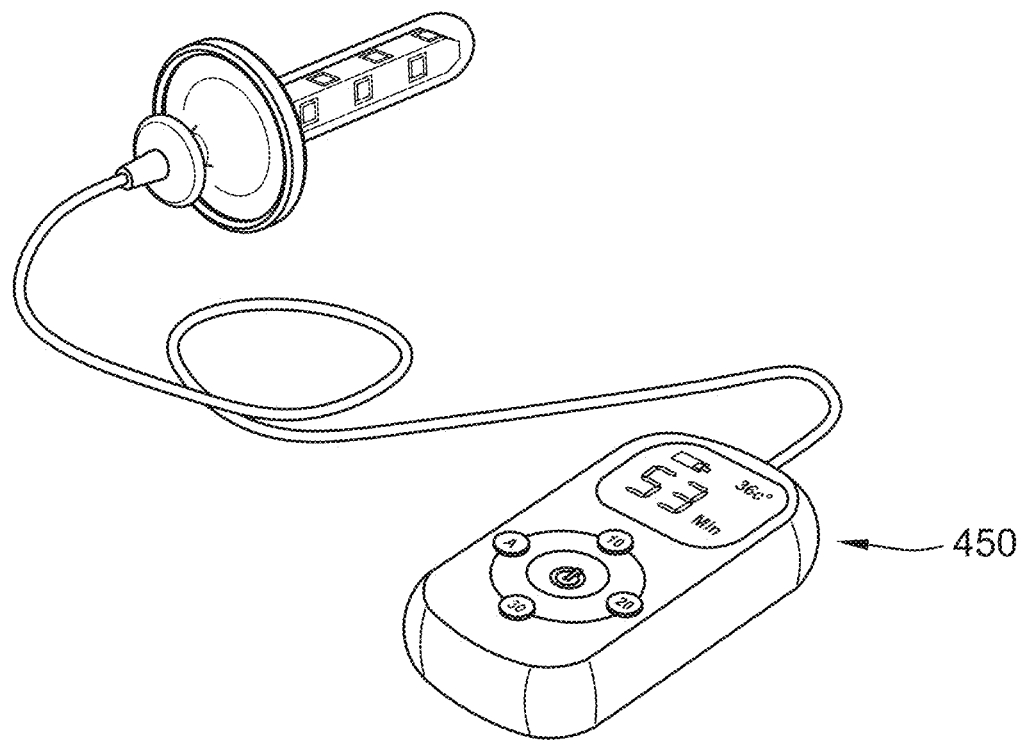
FIG. 26 illustrates an exemplary UV emitting device in accordance with an embodiment of the present disclosure.
Figure 27:
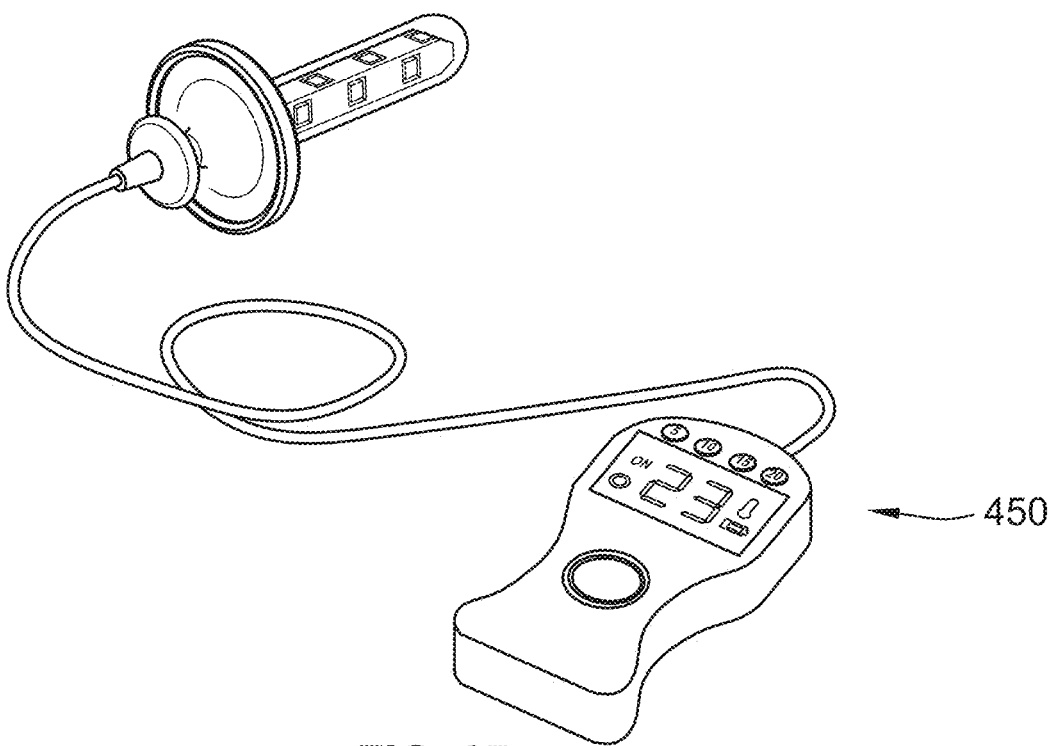
FIG. 27 illustrates an exemplary UV emitting device, in accordance with an embodiment of the present disclosure.
Figure 28:
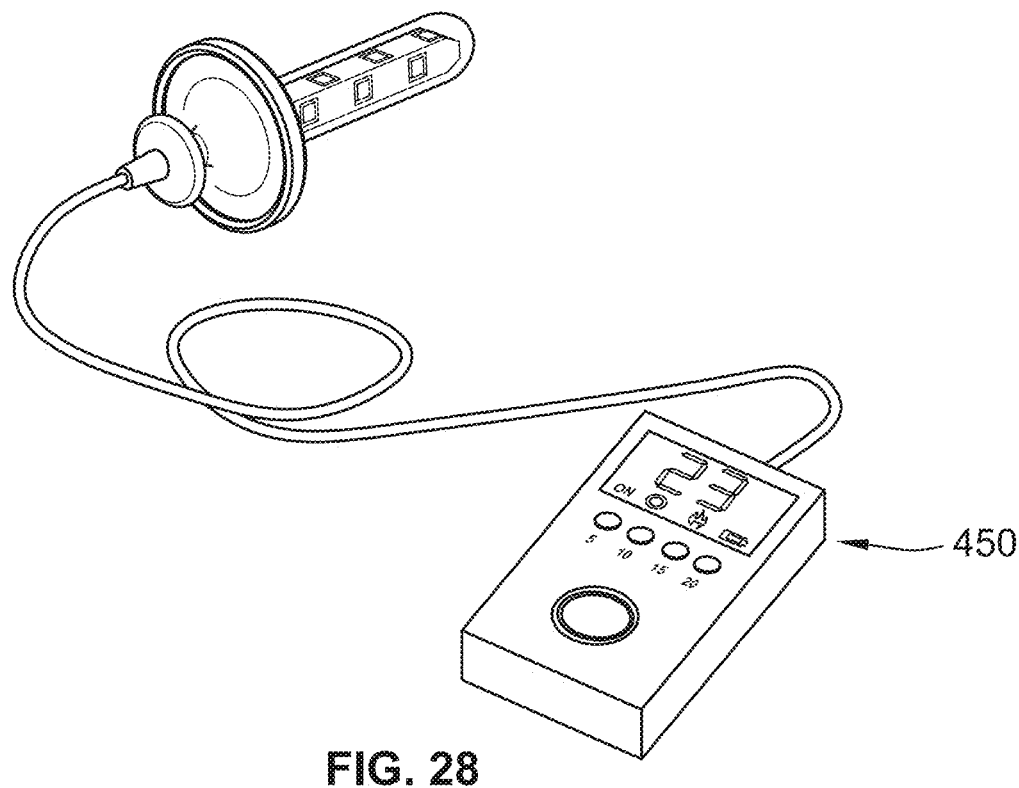
FIG. 28 illustrates an exemplary UV emitting device in accordance with an embodiment of the present disclosure.
Figure 29:
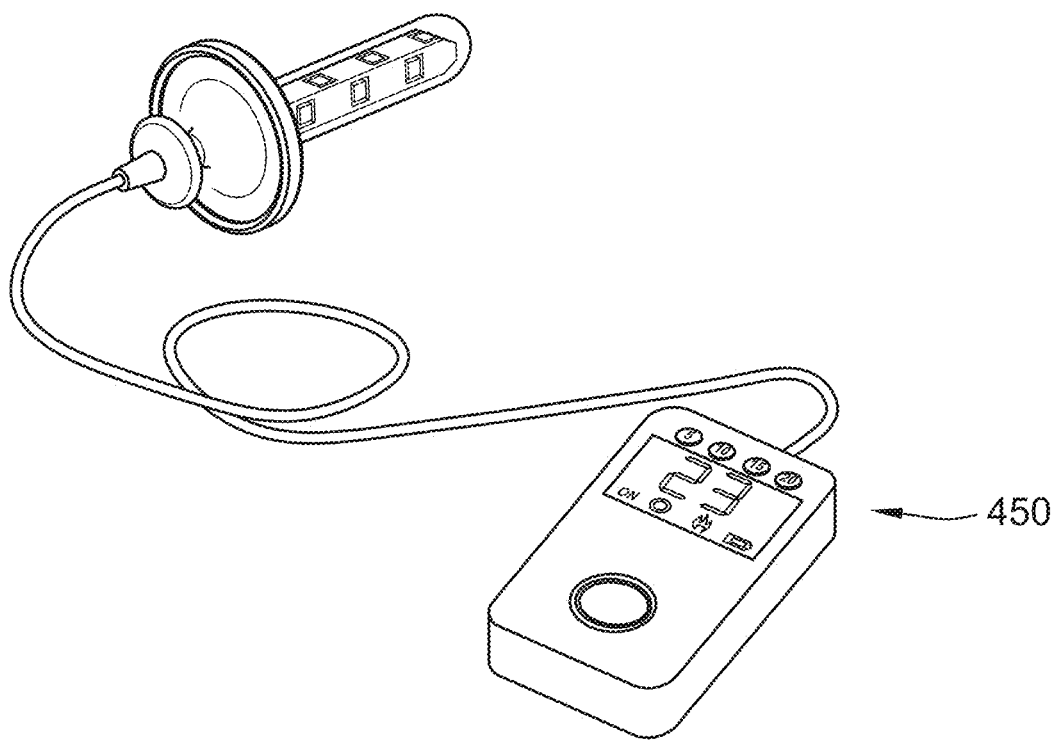
FIG. 29 illustrates an exemplary UV emitting device in accordance with an embodiment of the present disclosure.

The delivery tube/rod 100 may be made of any suitable construction (e.g., rigid or flexible), including various polymers that are biocompatible or have a biocompatible coating. FIG. 25 illustrates an exemplary UV emitting device 400, in accordance with an embodiment of the present disclosure. In some embodiments, the delivery tube/rod 100 can include an outer layer of transparent material to allow the UV light from the light sources 430 to radiate outward from the delivery tube/rod 100. In some embodiments, the delivery tube/rod 100 may include an outer surface made from, e.g., silicon, silica, polyurethane, polyethylene, Teflon/PTFE, borosilicate, or other suitable materials. In some embodiments, the delivery tube/rod 100 is constructed using copper with a borosilicate outer layer. For optimal cooling, area of exposure, and uniformity, the delivery tube/rod 100 can include multiple light emitting diodes (LEDs) staggered on a copper bar. In some examples, eight (8) LEDs can be provided on the delivery tube/rod. The spacing of the light sources 430 enables an optimal vertical illuminated length. In some embodiments, the vertical illuminated length extends between 8-10 cm around the delivery tube/rod 100.

By manufacturing the body of the delivery tube/rod 100 using copper, the delivery tube/rod 100 is able to withstand reaching elevated levels in temperature. The copper serves as a heat sink, preventing the delivery tube/rod 100 from reaching uncomfortable temperatures. Applicant also proposes operating the light sources 150 at specific currents to optimize the temperature of the delivery tube/rod 100. In some examples, the light sources 150 are operated within the range of 60-100 mA. Within the proposed range, the temperature of the delivery tube/rod 100 doesn't raise above 40° C., therefore achieving the goal of implementing a proper cooling solution.

FIGS. 26-29 illustrate various examples of a UV light delivery system with a controller 450. The controller 450 may include one or more processors, memory, and a battery or other power source. The memory may contain instructions with various therapy regimens that may be applied using various intensities and/or durations as disclosed herein. For instance, the memory may contain data structures that when executed by a processor, provide power to the light sources 150 with a given intensity or timing. The controller may be utilized for any of the embodiments disclosed herein, including the vaginal, GI, and ETT based UV light delivery device.

Figure 30:
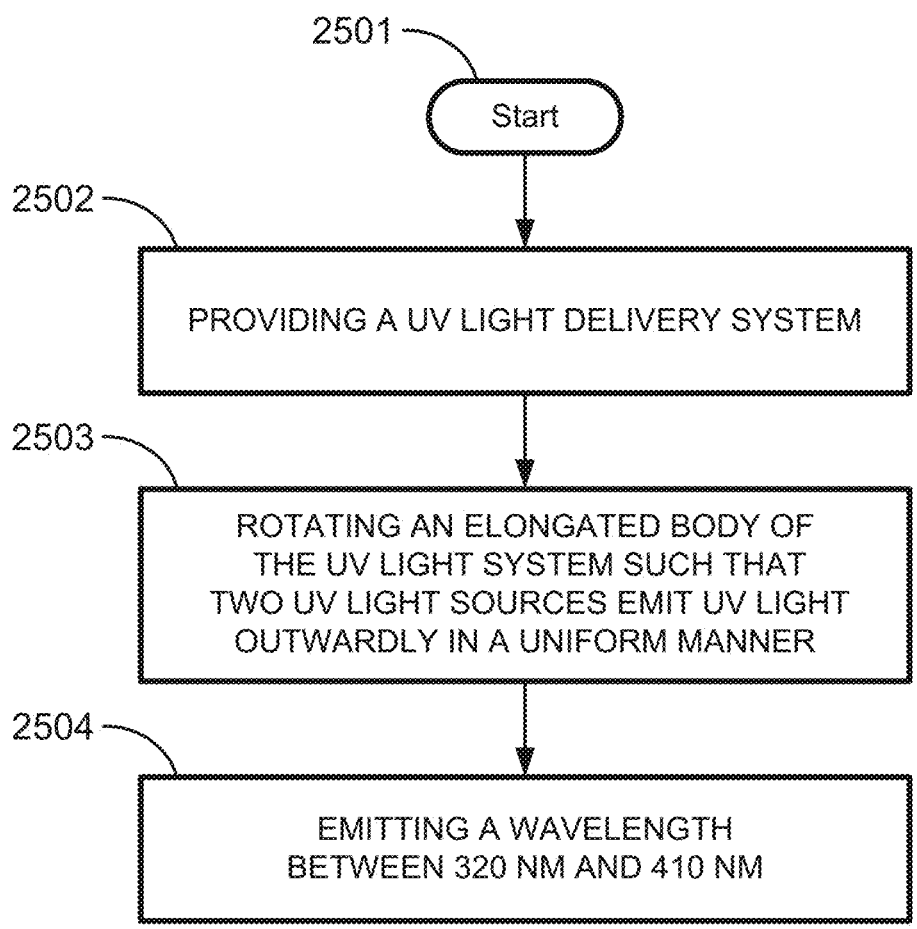
FIG. 30 illustrates an exemplary process for performing intra-corporeal ultraviolet therapy, in accordance with an embodiment of the present disclosure.

Referring to FIG. 30, a process for performing intracorporeal ultraviolet therapy is provided. The process includes providing a UV light delivery device, in step 2501. The UV light delivery device includes an elongated body including a proximal end and a distal end. The elongated body includes receiving spaces. The UV light delivery device can also include UV light sources configured to be connected to the receiving spaces. In some examples, the method also includes rotating the elongated body such that the two UV light sources are configured to emit UV light outwardly in a uniform manner, at step 2503.

The process can also include emitting, from the two UV light sources, wavelengths between 320 nm and 410 with a peak wavelength of 340, 341, 342, 343, 344, 345, 346 nm, at step 2504. In some examples, the process also includes emitting, from the two UV light sources, radiation outwardly from the elongated body. In some examples, the elongated body includes four sides. Each of the four sides of the elongated body includes a receiving space, such that corresponding UV light sources 150 are staggered on the elongated body.

The elongated body includes a receiving space and a corresponding UV light source at the proximal end. The elongated body is partially coated with borosilicate glass. In some examples, the elongated body is made up of copper. Respiratory In some examples, the systems and methods disclosed herein may be utilized to delivery UV light to the internal passageways of the respiratory system of a patient. For instance, in some examples, a delivery tube 150 may be navigated into an endotracheal tube (ETT) while a patient is being ventilated. Alternatively, a delivery tube 150 can be navigated into a nasopharyngeal airway (NPA) of a patient. These applications may be utilized to treat or prevent infections, including viral, bacterial, pneumonia, and other infections.

In some examples, the delivery tube 100 may be inserted into the ETT during suctioning of the ETT. In other examples, the systems and methods here may be utilized for improving the treatment of empyema by equipping chest tubes with a delivery tube to deliver internal light therapy.

For instance, systems and methods have been developed to provide internal ultraviolet therapy in conjunction with an endotracheal tube (ETT) as disclosed herein. Accordingly, the delivery tube 100 may be navigated inside an ETT during ventilation of a patient. In other examples the delivery tube 100 may be connected to or built into an ETT, or an ETT may have light sources 150 incorporated into the ETT. Accordingly, the light sources 150 may be positioned within the tube 150 and/or ETT so that the UV light sources 150 radiate the respiratory tissue in the tracheal airways surrounding the ETT.

For instance, systems and methods have been developed to provide internal ultraviolet therapy in conjunction with a nasopharyngeal airway (NPA) as disclosed herein. Accordingly, the delivery tube 100 may be navigated inside an NPA of a patient. In other examples the delivery tube 100 may be connected to or built into an NPA, or an NPA may have light sources 150 incorporated into the NPA. Accordingly, the light sources 150 may be positioned within the tube 150 and/or NPA so that the UV light sources 150 radiate the respiratory tissue in the nasopharyngeal airways surrounding the NPA.

In some examples, the UV light sources 150 in the delivery tube 100 may be a string of LEDs. For instance, the delivery tube 100 may be a flexible catheter that connects to an ETT or an NPA, and may have LEDs positioned on or inside the catheter to emit UV light outward from the delivery tube 100 to treat the respiratory canals of the patient and/or treat the inside of the ETT or NPA. The LEDs may be connected with a wired connection to a power supply. In other examples, the light sources 150 may be other suitable light sources 150 other than LEDs.

In this example, the LEDs may have a maximum emission intensity wavelength, of 335, 336, 337, 338, 339 340, 341, 342, 342, 344, 345, 346, 347, 348, 349, 350 nm, or any range of wavelengths between 335 and 350 nm. In other embodiments, the LEDs may deliver wavelengths between 320 nm-410 nm, 250 nm-400 nm or other suitable ranges as discussed herein.

Figure 31:
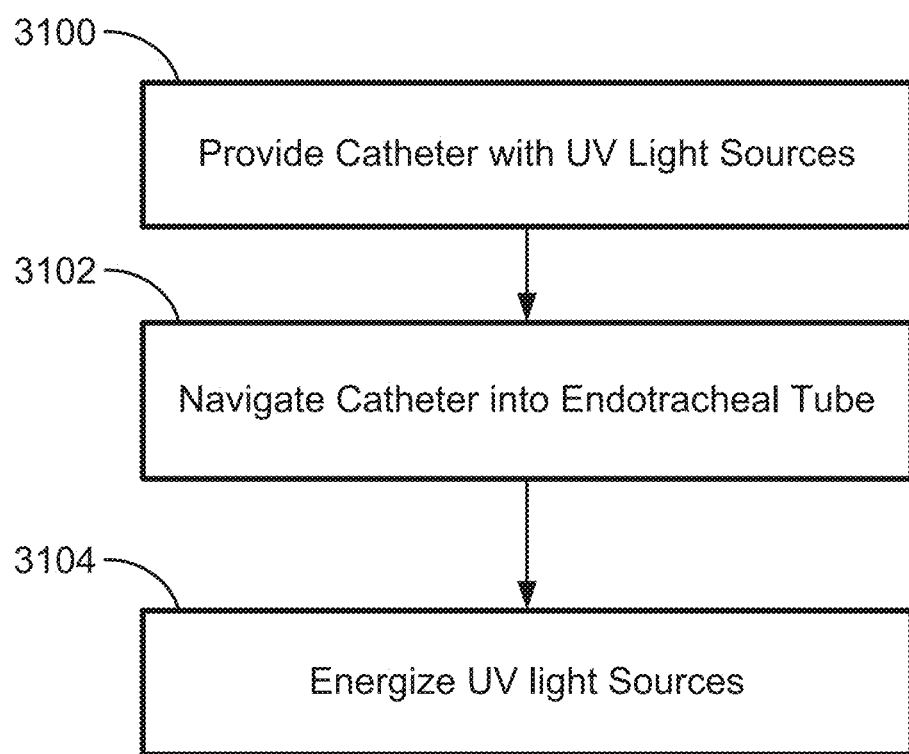
FIG. 31 illustrates an exemplary process for performing intra-corporeal ultraviolet therapy in connection with an ETT, in accordance with an embodiment of the present disclosure.

FIG. 31 illustrates a flowchart showing an example of a treatment regimen for treating a respiratory canal and surrounding tissue of a patient with UV light. For instance, a catheter or other delivery tube 150 with UV light sources may be provided 3100 and navigated into an ETT 3102. Then, the UV light sources may be energized for various treatments 3104.

In some examples, a delivery catheter with LEDs with wavelengths of maximum emission intensity centered around 339, 340, 341, 342, 343, 344, 345, or 346 nm may be energized for at least 15, 16, 17, 18, 19, 20, 21, 22, 23, 24, 25, 26, 27, 28 29, 30, 40, 60, 80, or 90 minutes (or other suitable time frames in between or outside these ranges) once, twice, or three times daily. The intensity applied may be 1500, 1600, 1700, 1800, 1900, 2000, 2100, 2200, 2300, 2400, 2500, 2600, 2700, 2800, 2900, 3000, 3100, 3200, 3300 uW/cm$^2$, or other suitable intensities between or outside these ranges based on the power of the LEDs and the distance to the tracheal or other respiratory canal tissue from the LED light sources.

Additional Treatment Applications and Regimens

The procedures herein may be utilized to treat a number of different inflammatory and infectious diseases. Accordingly, different amounts or time period dosages of UV radiation may be administered depending on the following: (1) type of disease, (2) type of light source, (3) light source power, (4) light source UV range, and (5) severity of the infection or inflammation. For instance, in some embodiments, the time of administration will be determined by the capsule digestion rate, and other factors (e.g., light source power, UV range, and the like) can be manipulated to vary the dosage. In other examples, the endoscope may be delivered by the physician/surgeon for an hour, 30 minutes, two hours, or other suitable times.

Following are examples of treatment regimens and their applications. Accordingly, the devices and methods disclosed herein may be adapted to treat these different conditions.

Urology and Nephrology:
1. Sterilizing blood in patients with known bacteremia, fungemia or viremia during dialysis to eradicated or to decrease the microorganism load. Alternative a light needle can be placed in fistula to be turned on even outside of dialysis window. Ex vivo sensitivity analysis will be done for narrower wavelength but more intense ILT.
2. Sterilizing indwelling urinary catheters in catheter dependent patients
3. Treatment of bladder and urethral cancer limited to mucosa and submucosa
4. Treatment of refractory cystitis/urinary tract infection
5. Adding UV phototherapy to peritoneal dialysis catheter to decrease the risk of peritonitis and even long term peritoneal sclerosis.

Cardiology
1. Sterilizing blood in patients with known bacteremia, fungemia or viremia with LVAD to eradicated or to decrease the microorganism load. Alternative a light needle can be placed in fistula to be turned on even outside of dialysis window. Ex vivo sensitivity analysis can be done for narrower wavelength but more intense UV therapy.
2. Refractory bacterial and fungal endocarditis being treated with direct UV light exposure of valves. A photosensitizer may be given intravenously in this case.

Dentistry
1. Treatment of gingivitis.
2. Treatment leukoplakia and oral lichen planus.
3. Treatment of cancers limited to mucosa and submucosa Hematology/Oncology
1. Treatment of intestinal Graft-versus-host disease. X-ray wavelength will be emitted in this case, leading to death of lymphocytes. This can be used in patients with endstage Crohn's disease awaiting small bowel transplant or palliative care.

ENT
1. Treatment of chronic sinusitis.
2. Treatment of chronic otitis.
3. Treatment of acute otitis media in patients requiring tympanostomy.
4. Treatment of nasal polyps (evidence suggests that UV light shrinks them).
5. Treatment of halitosis.
6. Treatment of recurrent tonsillitis/pharyngitis.
7. Treatment of cancers limited to mucosa and submucosa Surgery
1. Improving the treatment of abscesses by equipping the drains with UV light technology.
2. Use with surgical drains to avoid superimposed infection.
3. Accelerating anastomosis healing process.
4. Aid in preventing adhesions.

Neurosurgery
1. Intrathecal fibro-optic delivery of UV light in treatment of refractory meningitis.
2. Treatment of refractory shunt infections.
3. Treatment of prion diseases with intrathecal or subarachnoid UV therapy. 4—Treating JC virus related Progressive multifocal leukoencephalopathy by decreasing viral load.

Gynecology
1. Treatment of bacterial or fungal vaginosis.
2. Treatment of rectovaginal/colovesical fistula.
3. Treatment of cancers limited to mucosa and submucosa Rheumatology 1. Intra-articular ILT for treatment of inflammatory and infectious large joint arthritis.

Vaginal Therapy

1. FIGS. 14A, 14B illustrate an example of a UV emitting device being used on a vaginal treatment of a mouse.

EXPERIMENTAL DATA

The following set of experimental data is provided to better illustrate the claimed invention and is not intended to be interpreted as limiting the scope.

Example 1: *E. coli*

Figure 12A:
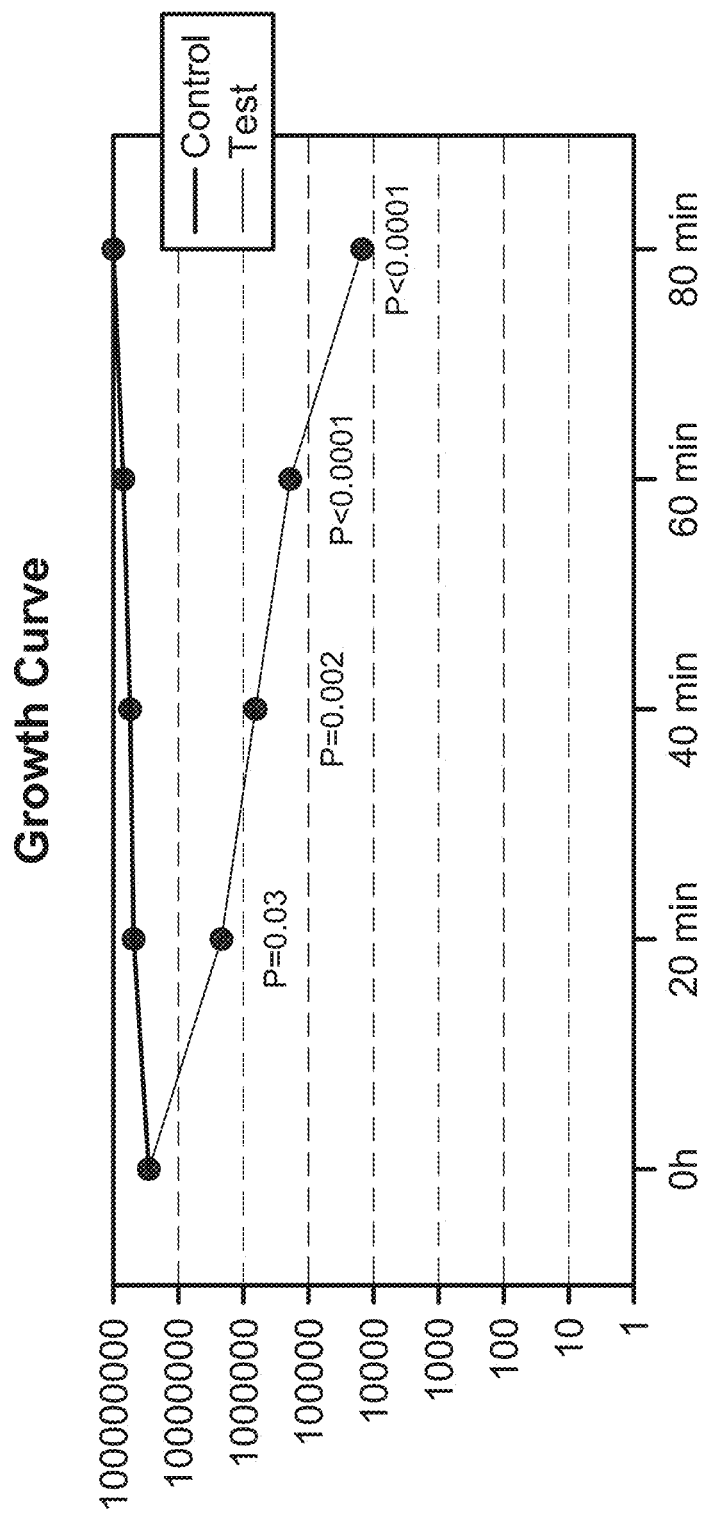
FIG. 12A illustrates a growth curve of *E. coli* when implementing the exemplary UV emitting device of the present disclosure.
Figure 12B:
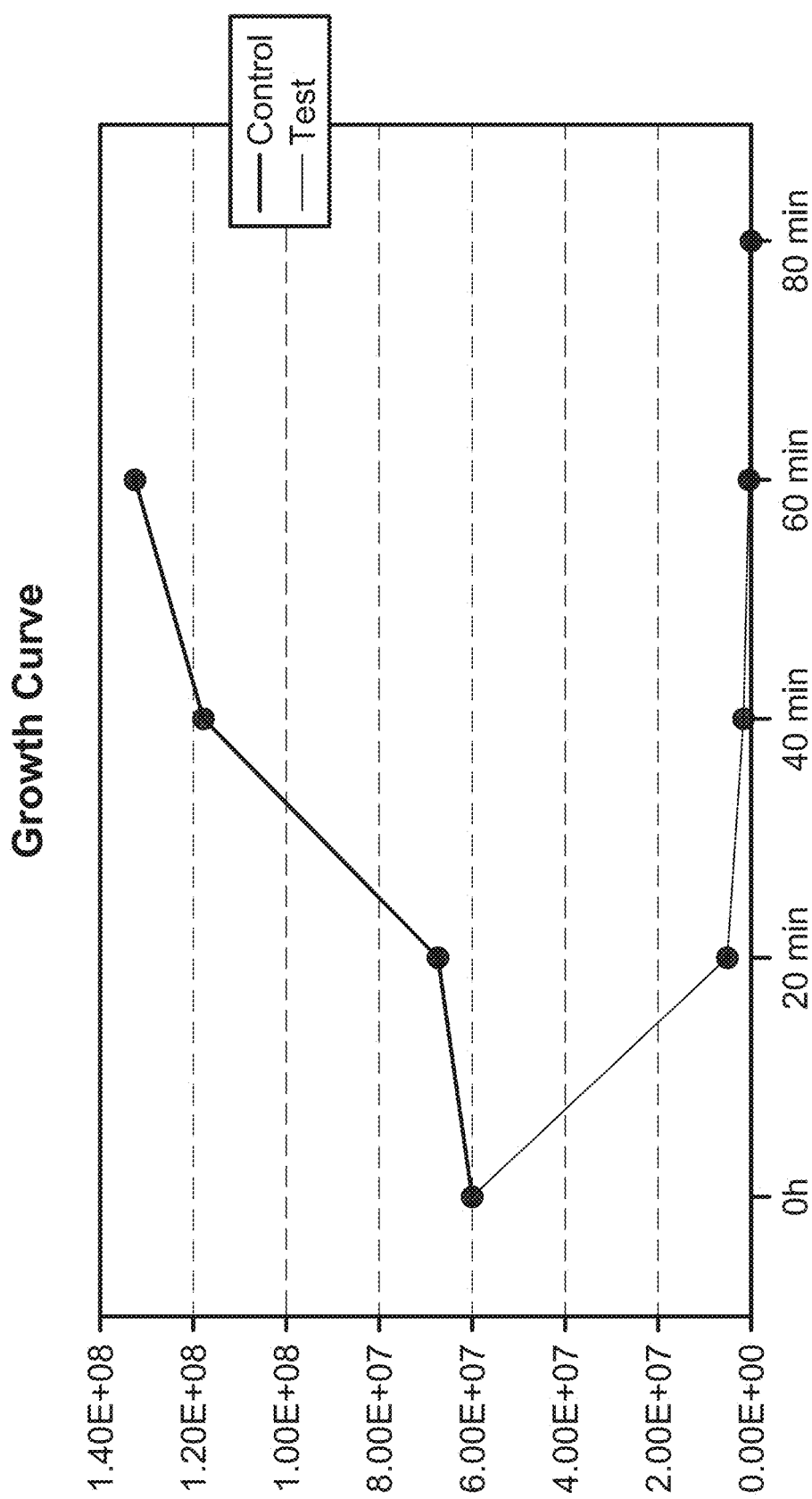
FIG. 12B illustrates a growth curve of *E. coli* when implementing the exemplary UV emitting device of the present disclosure.

FIGS. 12A and 12B illustrate experimental data showing an example of a UV emitting device of the present disclosure being used to prevent *E. coli* from proliferating. As shown, the control group where the UV light was not applied continued to grow, whereas the test group that had UV light applied through the UV emitting device showed continuous decrease in *E. coli* count over time. The UV light is shown to both prevent *E. coli* from proliferating and also kill the bacteria over time.

Figure 15A:
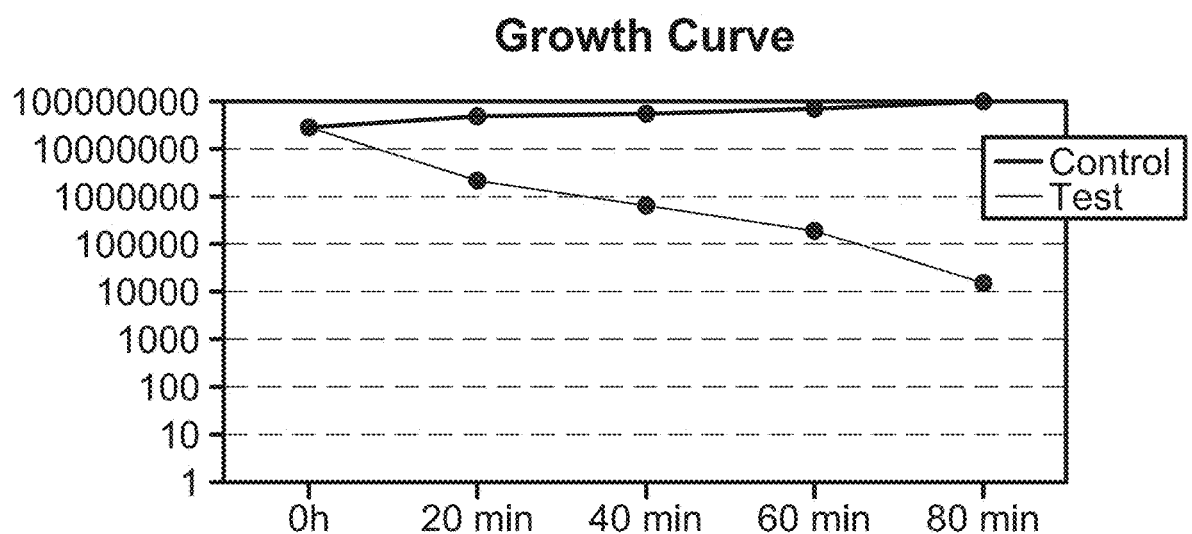
FIG. 15A illustrates a growth curve of liquid culture containing *E. coli* when implementing the exemplary UV emitting device of the present disclosure.
Figure 15B:
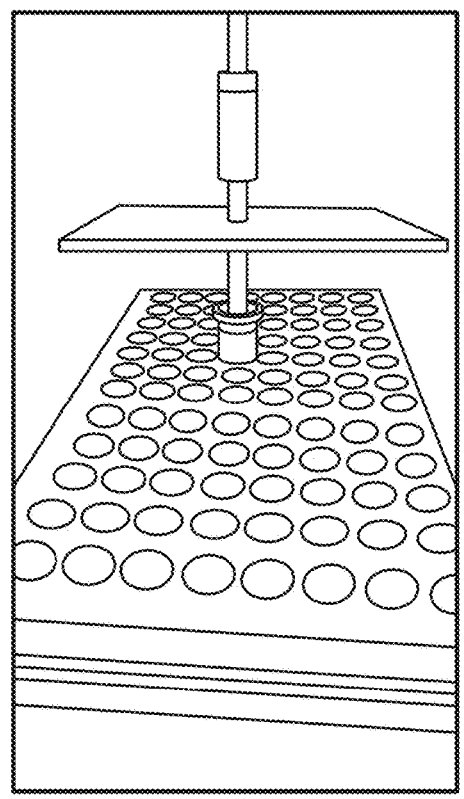
FIG. 15B illustrates an exemplary UV emitting device of the present disclosure implemented on a liquid culture containing *E. coli;*
Figure 16:
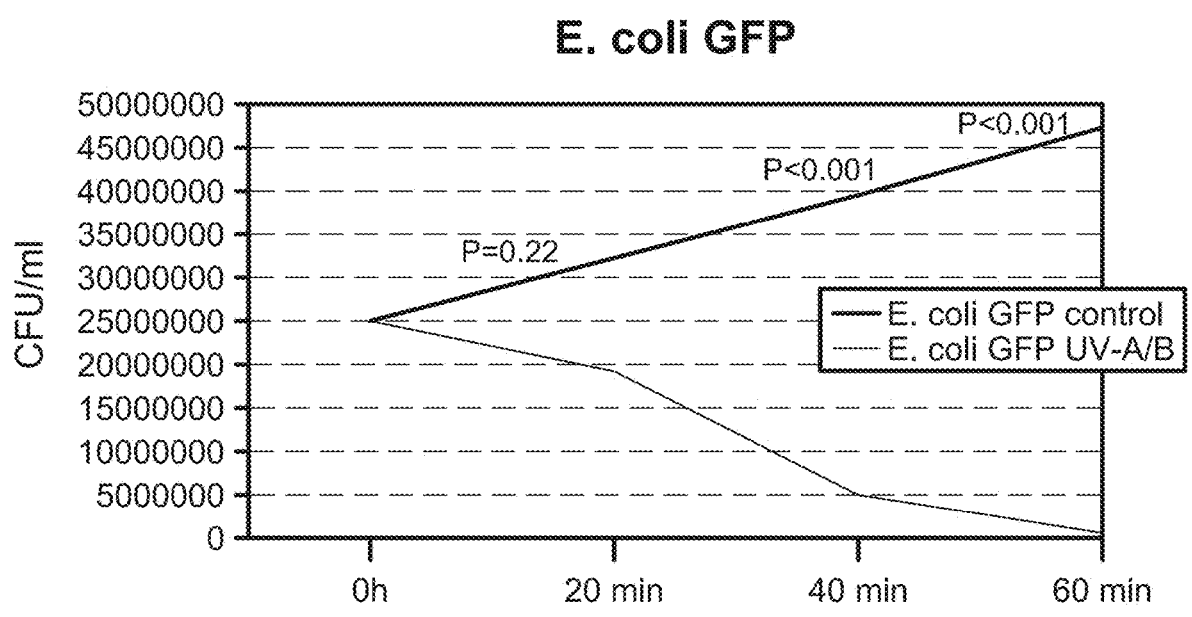
FIG. 16 illustrates a growth curve of liquid culture containing *E. coli* when implementing an exemplary UV emitting device of the present disclosure.
Figure 17A:
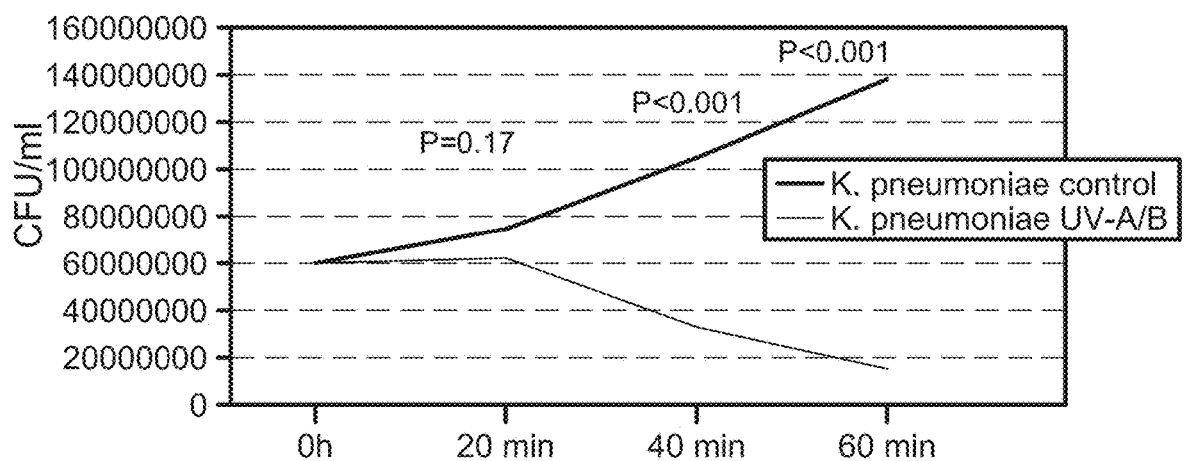
FIGS. 17A and 17B illustrate growth curves of liquid culture containing *E. coli* when implementing an exemplary UV emitting device of the present disclosure.
Figure 17B:
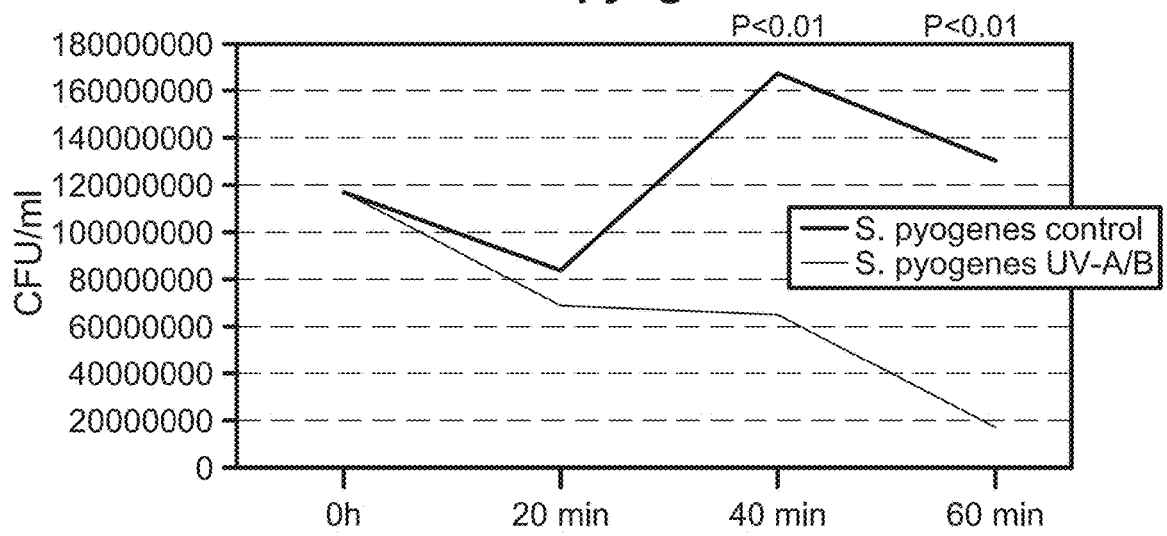
Figure 18:
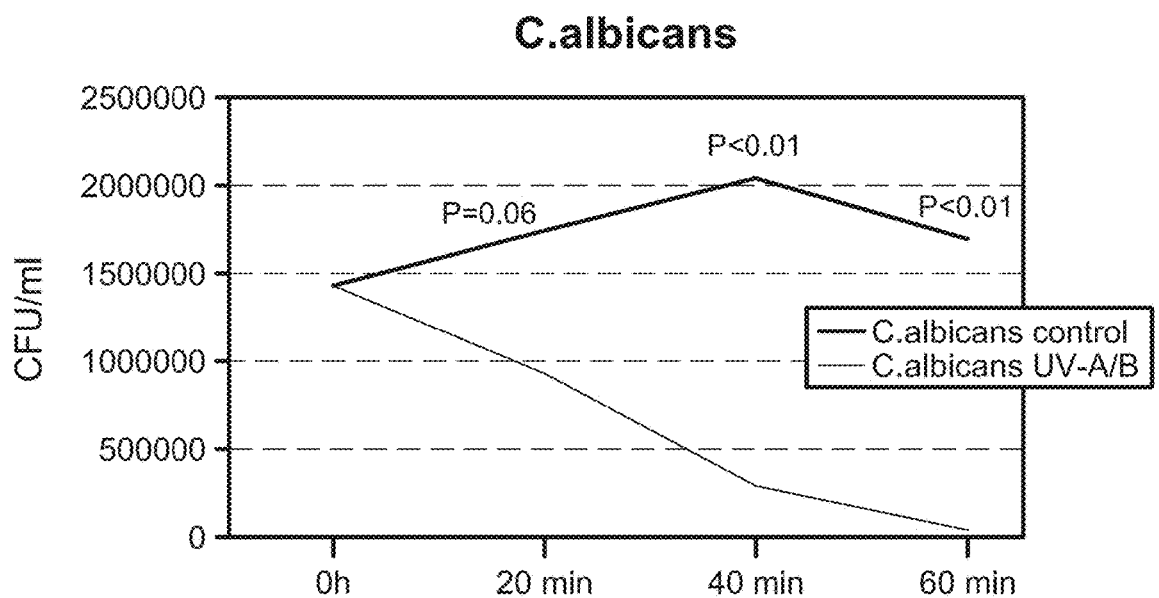
FIG. 18 illustrates a growth curve of liquid culture containing *E. coli* when implementing an exemplary UV emitting device of the present disclosure.
Figure 19:
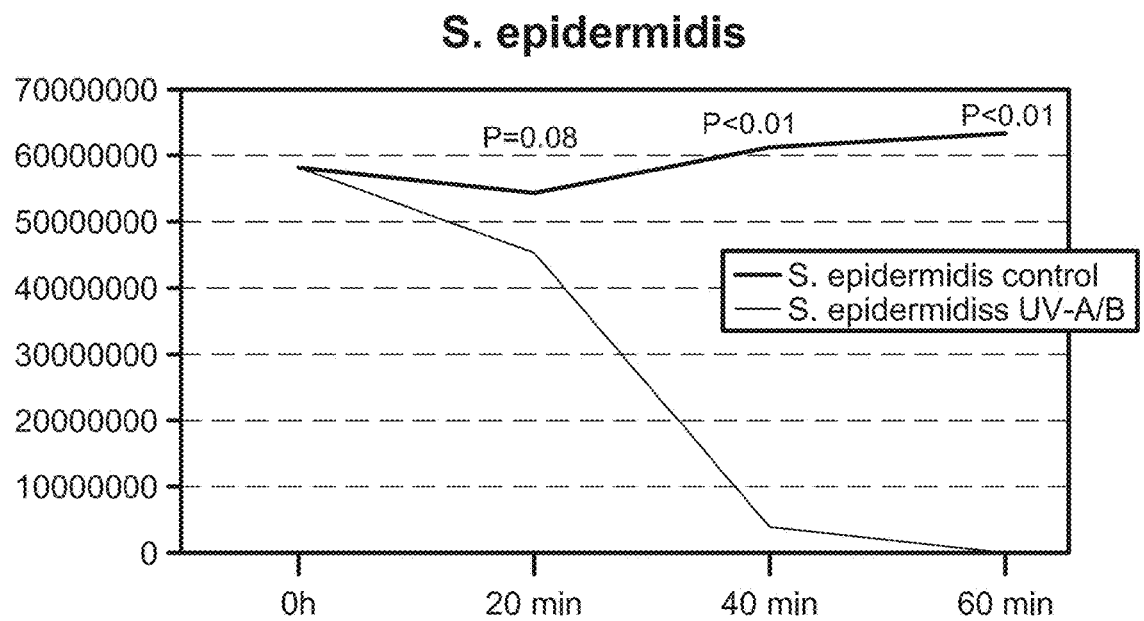
FIG. 19 illustrates a growth curve of liquid culture containing *E. coli* when implementing an exemplary UV emitting device of the present disclosure.
Figure 20:
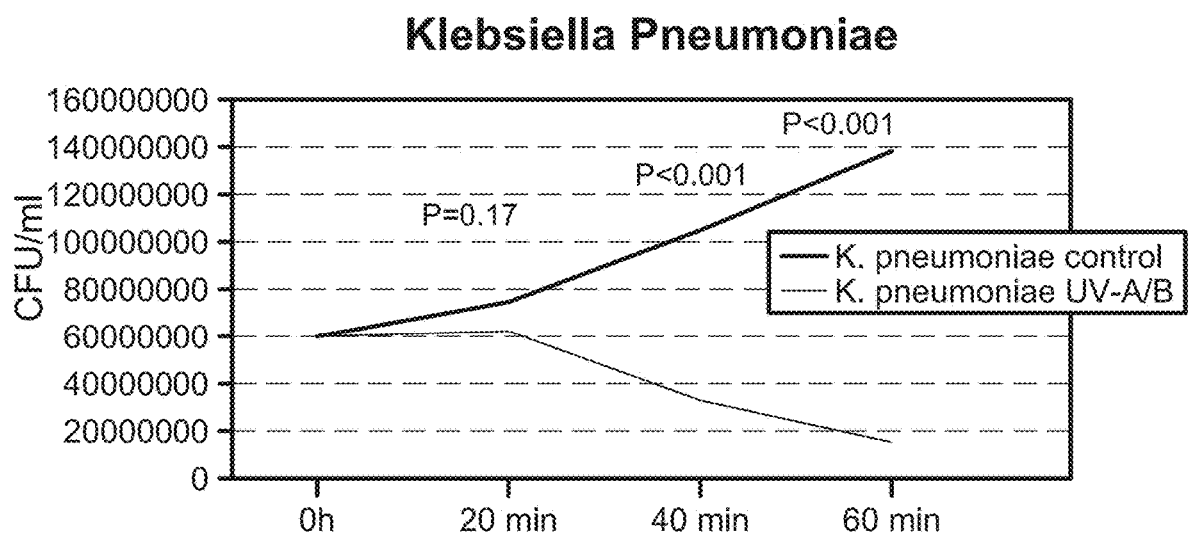
FIG. 20 illustrates a growth curve of liquid culture containing *E. coli* when implementing an exemplary UV emitting device of the present disclosure.
Figure 21A:
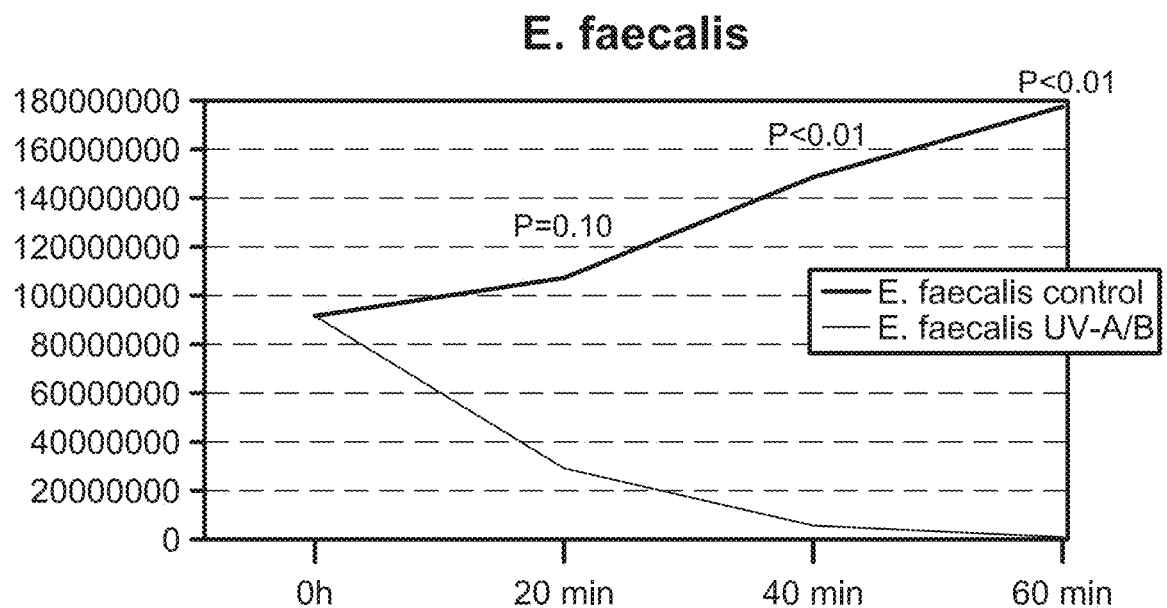
FIGS. 21A and 21B illustrate a growth curve of liquid culture containing *E. coli* when implementing an exemplary UV emitting device of the present disclosure.
Figure 21B:
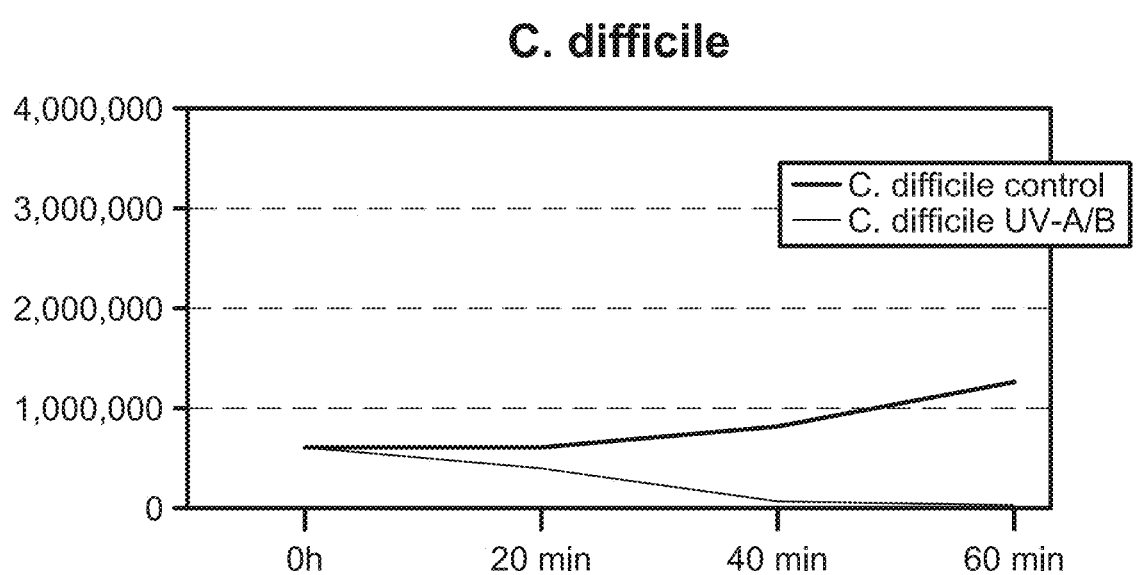

FIG. 15B illustrates an example of a UV emitting device of the present disclosure being used on a liquid culture containing *E. coli*. The results of this experiment and similar experiments with other bacteria and a fungus, *C. albicans* are shown in, e.g., FIGS. 15A, and 16, 17A-17B, 18-20, 21A, and 21B. All of the results illustrate a significant reduction in the growth of *E. coli* and other infectious agents in liquid samples where UV-A and UV-B lights were emitted by the UV emitting device of the present disclosure onto the liquid samples.

Example 2: bacteria

In another example, two exemplary devices according to the present disclosure were used in UVA experiments to treat bacteria. The first device was a borosilicate rod (outer diameter 3 mm) repeatedly etched with a mixture of diluted sulfuric acid, sodium bifluoride, barium sulfate and ammonium bifluoride, with a reflective coating added to the end of the rod through which UVA was side-emitted. This process resulted in a side glowing rod of UVA (peak wavelength of 345 nm) as confirmed by spectrometer (Ocean Optics; Extech). The second device incorporated narrow band LEDs with a peak wavelength of (345 nm).

The UVA rod was inserted into liquid media. A mercury vapor lamp served as light source (Asahi Max 303, Asahi Spectra Co., Tokyo, Japan). The second UVA light-emitting device was a miniature light-emitting diode (LED) array (peak wavelength 345 nm) mounted on a heatsink (Seoul Viosys, Gyeonggi-Do, Korea). This device was used for the plated experiments noted below.

Stock cultures of *Escherichia coli*, *Escherichia coli* GFP, *Pseudomonas aeruginosa*, *Streptococcus pyogenes*, *Staphylococcus epidermis*, *Klebsiella pneumoniae*, *Enterococcus faecalis*, *Proteus mirabilis*, *Clostridioides difficile* and *Candida albicans* were grown in appropriate liquid culture media and conditions as illustrated in the table shown in FIG. 32. The American Type Culture Collection (ATCC) strains and one clinical isolate were grown in appropriate solid and liquid media following instructions suggested by the ATCC for each microorganism (Manassas, VA, USA). Using sterile techniques, the vial containing the microbial strain was opened and the entire pellet was rehydrated with approximately 500 of liquid broth.

Aseptically, the resuspended pellet was transferred to a tube containing 5-6 mL of the same liquid broth used to resuspend the cells. Several drops of the primary broth tube were used to inoculate a solid microbial agar and isolate single colony forming units (CFU). The liquid and solid cultures were incubated at specific temperatures, atmospheric conditions and times described in FIG. 32.

Initially, a liquid culture was prepared from a single CFU of each microbe to guarantee the purity of the strain during the UVA therapy. Only new pure liquid cultures were used during the experiments. One single colony was added to a 10 mL sterile tube containing 5 mL of liquid medium followed by thorough vortexing to homogenize the microbial cells. The liquid cultures shown in FIG. 32 were incubated until they reached the McFarland standard of 0.5. After meeting the standard turbidity, microbial cultures were mixed thoroughly for one minute and 1000 µL of the liquid culture were transferred into two 1.7 mL micro-centrifuge sterile tubes to be used as the treatment and control. An aliquot of 100 µL of each tube was serially diluted and plated on solid microbial medium to determine the number of CFU/mL at baseline as shown in FIG. 33.

Prior to UVA light therapy, several sterile 1.7 mL tube caps were prepared by creating a small hole through the top using a heated glass rod. The hole had the shape and size of the rod used to transmit UVA light.

Aseptically, the original caps from the liquid cultures in 1.7 mL tubes were replaced with the sterile caps with the hole. The UV light transmitter rod (sterilized with 70% ethanol) was placed into the hole created on the top of each cap. An identical rod was also placed into control-tubes. The light was transmitted through the glass rod inserted into the tube using the MAX-303 Xenon Light Source (Asahi Spectra USA, Inc., Torrance, CA). UV band width and irradiance peaks were assessed (Flame UV-VIS Fiber Optic Spectrometer, Ocean Optics). UV intensity was measured with SDL470 and UV510 UV light meters (Extech, NH, USA) Extech). Absence of UVC was confirmed using SDL470 UV light meter (Extech NH, USA). FIG. 32 describes the intensities and exposure durations of UVA light applied to the bacterial cultures.

After the end of the treatment time, the rods were removed from the treated and control tubes and a new sterile cap without a hole was used to close the liquid cultures. Both the treated and control groups were homogenized by vortexing. An aliquot of 100 µL of each tube was then serially diluted and plated on solid microbial medium to determine the number of CFU/mL after UVA treatment as shown in the table depicted in FIG. 33. This process was repeated until all time-points described in FIG. 33 were accomplished.

After each time point (baseline and post UVA treatment), 100 µL of the liquid microbial cultures (treated and controls) were serially diluted into sterile 1×PBS (EMD Millipore, Billerica, MA). The final serial dilution factors were 1:10 (100 µL of microbial culture and 900 µL of sterile 1×PBS), 1:100, 1:1000, 1:10,000 and 1:100,000. 100 µL of each dilution were plated in duplicates onto solid agar plates and incubated at time, temperature and atmospheric conditions described in FIG. 32. After incubation, the colonies were counted using a Scan 300 automatic colony counter (Interscience, Woburn, MA, USA), and the numbers of CFU/mL were defined after correcting for volume and the dilution factor.

The second device utilized in these experiments incorporated a miniature light-emitting diode (LED) array (peak wavelength 345 nm, bandwidth 10 nm) mounted on an aluminum heatsink (Seoul Viosys, Gyeonggi-Do, Korea). In the first experiment, this system was placed at 1 cm from the surface of a culture plate with a thick lawn of E. coli at approximately 2000 µW/cm² for 20 minutes. Subsequently, this light source was applied to liquid culture of 10 2 CFU/mL of E. coli and P. Aeruginosa in separate experiments.

For both conditions, UVA was tested in separate sets of experiments at intensities of 500, 1000, 2000 and 3000 µW/cm² for 20 and 40 minutes at 1 cm to produce a dose response curve. After incubation, the colonies were counted and colony sizes were measured using a Scan 300 automatic colony counter (Interscience), and the numbers of CFU/mL were defined after correcting for volume and the dilution factor.

Results

Exposure to UVA was associated with a significant reduction of various pathogenic microbes, including *Candida albicans* ($P=0.007$) and *Clostridium difficile* ($P=0.01$) as illustrated in the table depicted in FIG. 33. A UVA light exposure time of 20 min (intensity ranging 1300 to 3500 µW/cm²) was the minimum effective duration to observe reductions for most microorganisms tested when compared to controls ($P<0.05$), except *Klebsiella pneumoniae* ($P=0.17$), *Enterococcus faecalis* ($P=0.1$), and *Streptococcus pyogenes* ($P=0.64$). The UVA light exposure times of 40 and 60 min were effective against all microorganisms tested when compared to untreated controls ($P<0.05$, FIG. 33). Notably, the bactericidal and fungicidal effects exhibited a dose-dependent response to UVA light, with greater microbial reductions associated with longer exposure times as illustrated in FIG. 33.

Figure 34:
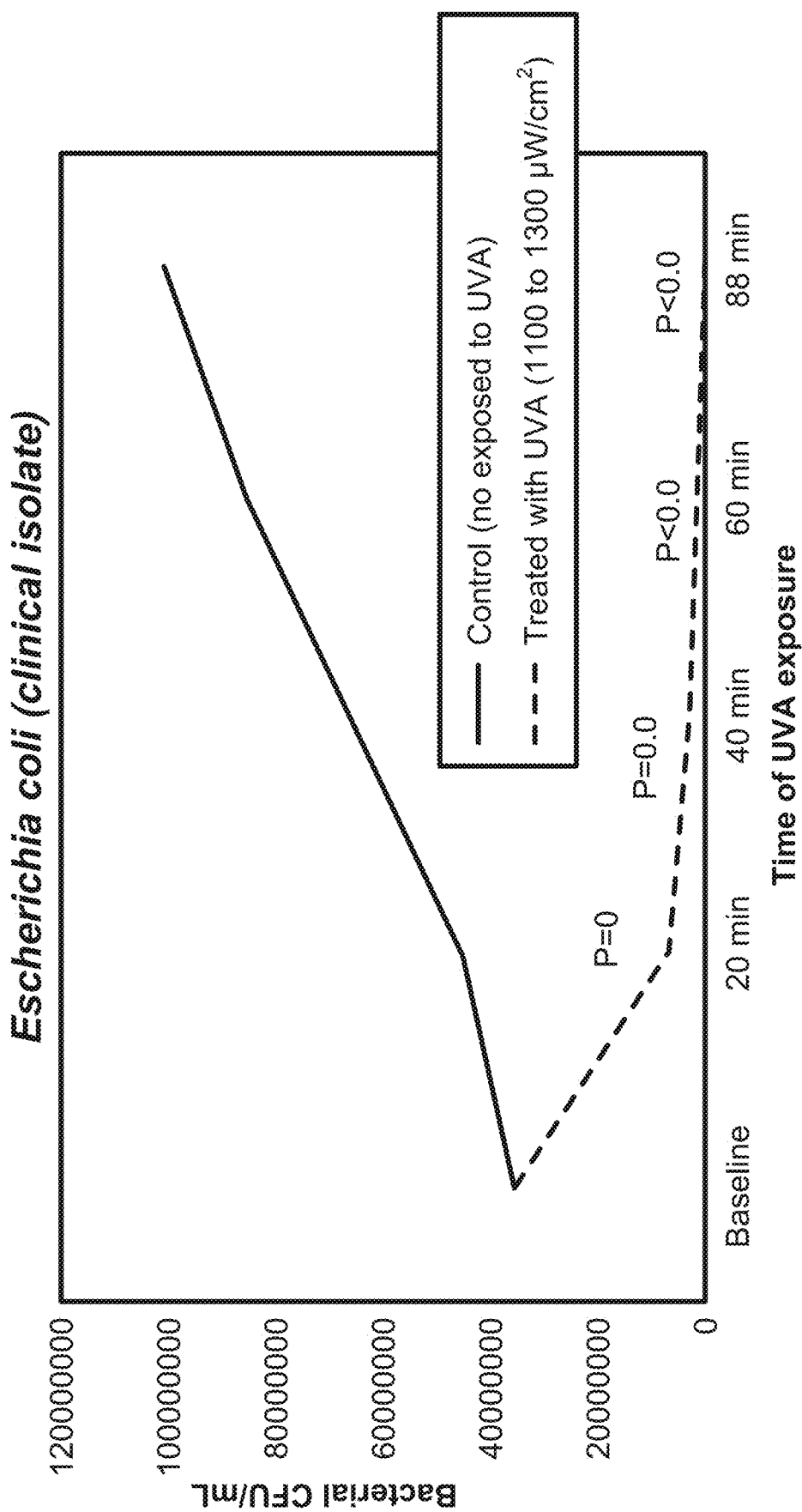
FIG. 34 illustrates growth curve showing bacterial counts over time during UV light exposure using an exemplary system according to the present disclosure.

UVA light treatment was also applied to a clinically isolated *Escherichia coli* strain obtained from a human urinary tract. UVA light was tested in a set of five consecutive experiments, exposing this bacterial culture to 20, 40, 60 and 80 minutes of UVA, 1100 to 1300 µW/cm². Compared to baseline, the number of CFU/mL observed in bacterial cultures exposed to UVA light decreased at all-time points evaluated, including 20 min ($P=0.03$), 40 min ($P=0.0002$), 60 min ($P<0.0001$) and 80 min ($P<0.0001$) as shown in FIG. 34.

Figure 35A:
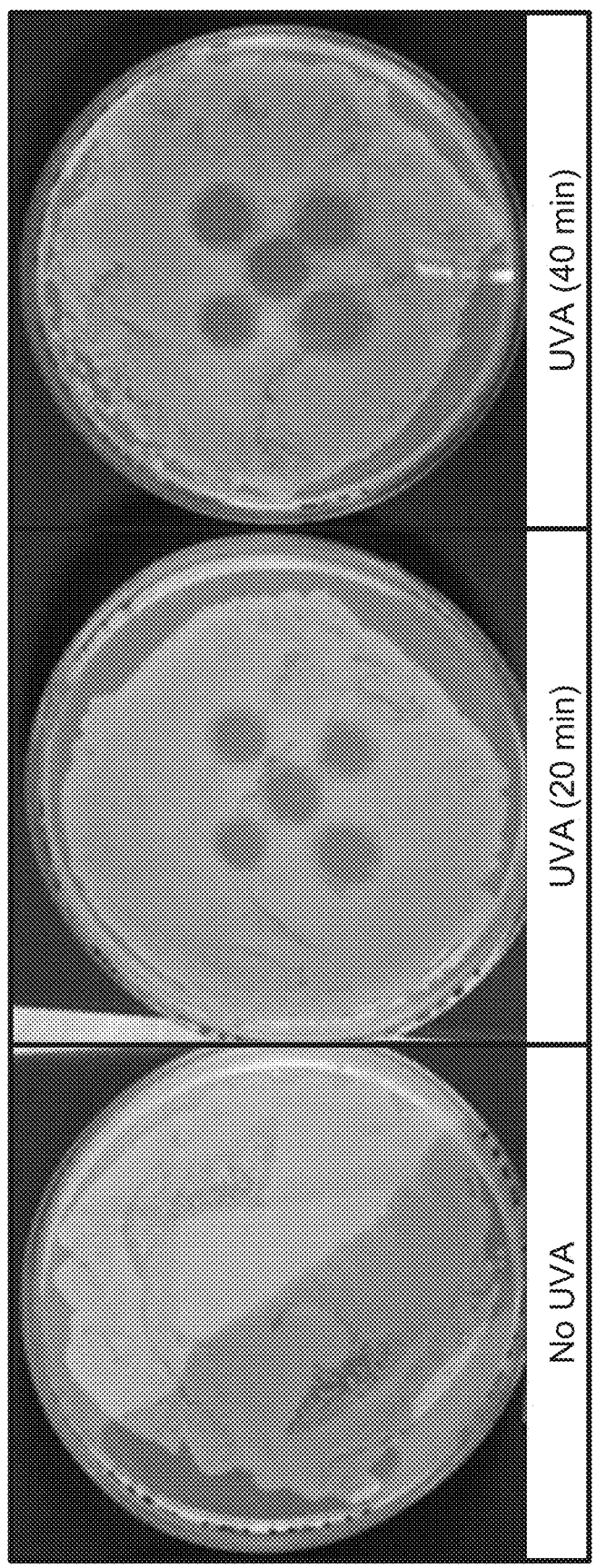
FIG. 35A illustrates images of petri dishes containing bacteria exposed to UV light over time compared to control.

Finally, experiments were conducted to test the effects of LED narrowband UVA (345 nm peak wavelength) on *E. coli* and *Pseudomonas aeruginosa*. In these experiments, this specific wavelength of UVA resulted in a significant reduction in bacterial cells as shown in FIGS. 35A-35N. For instance, FIG. 35A illustrates a picture of a bacterial colonies in petri dishes, and the pattern of disappearance of the colony around the site of application of the LED light at 20 and 40 minutes.

Figure 35B:
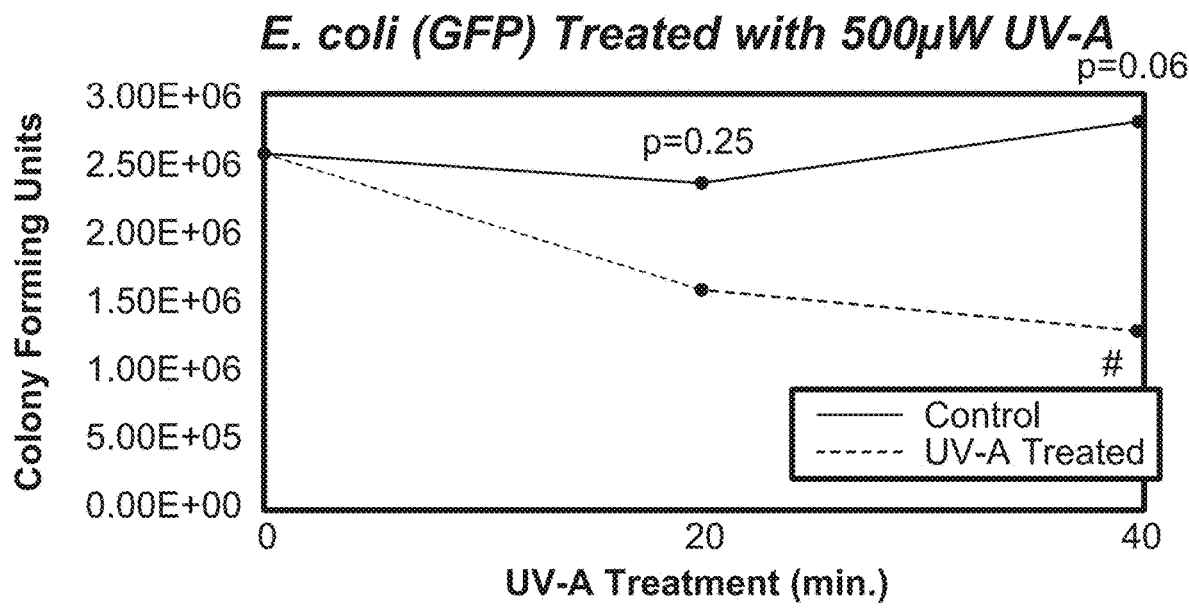
FIGS. 35B-35E illustrate growth curves showing *E. coli* bacterial counts over time exposed to various intensities of UV light using an exemplary system according to the present disclosure.
Figure 35C:
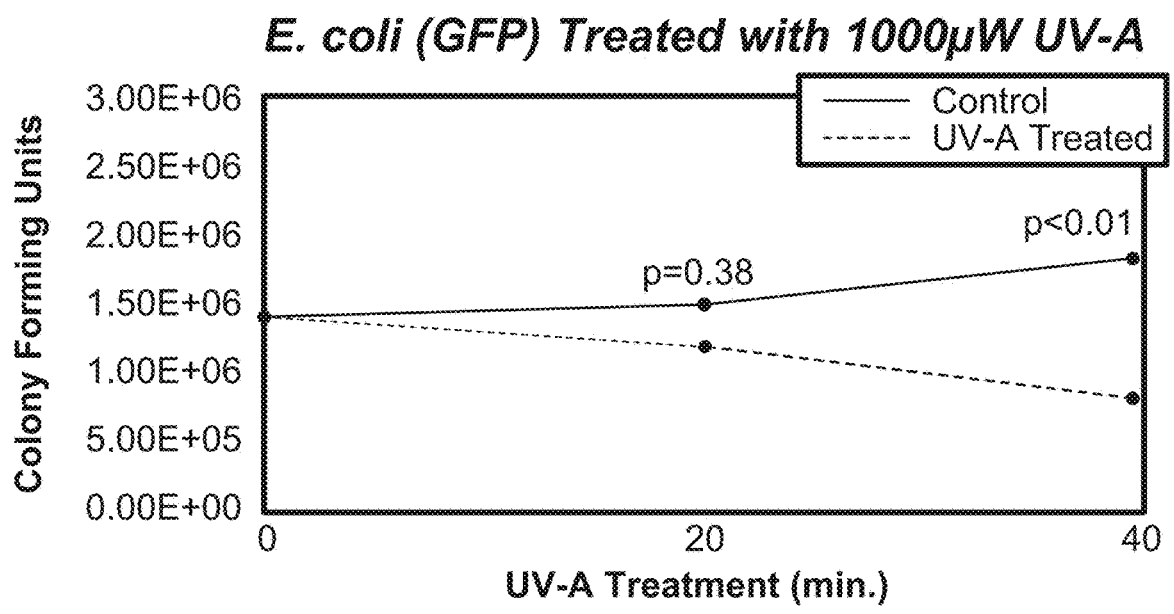
Figure 35D:
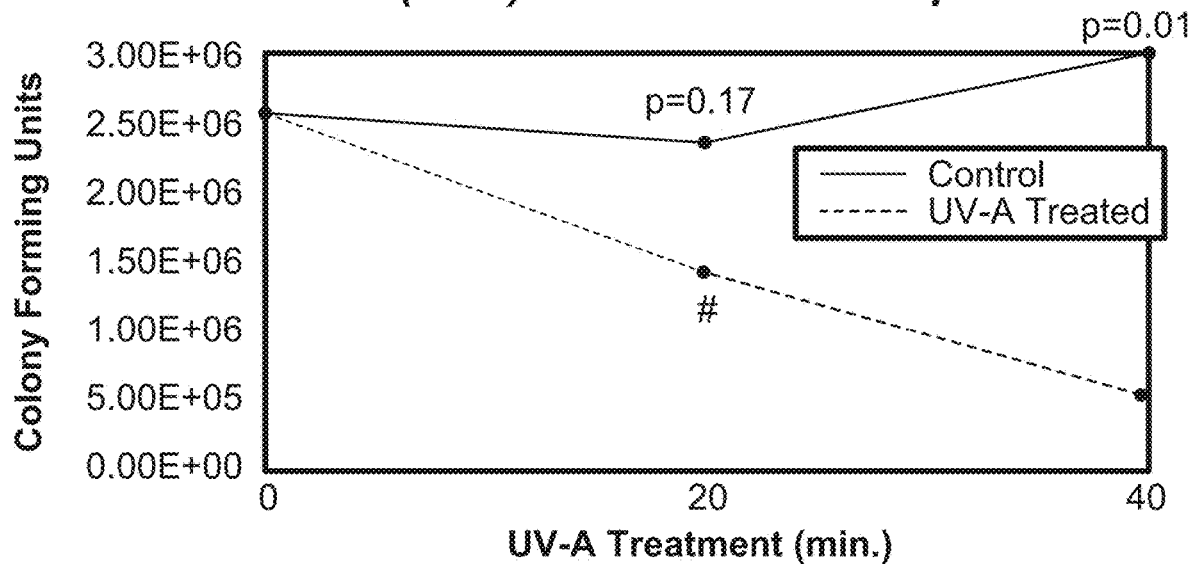
Figure 35E:
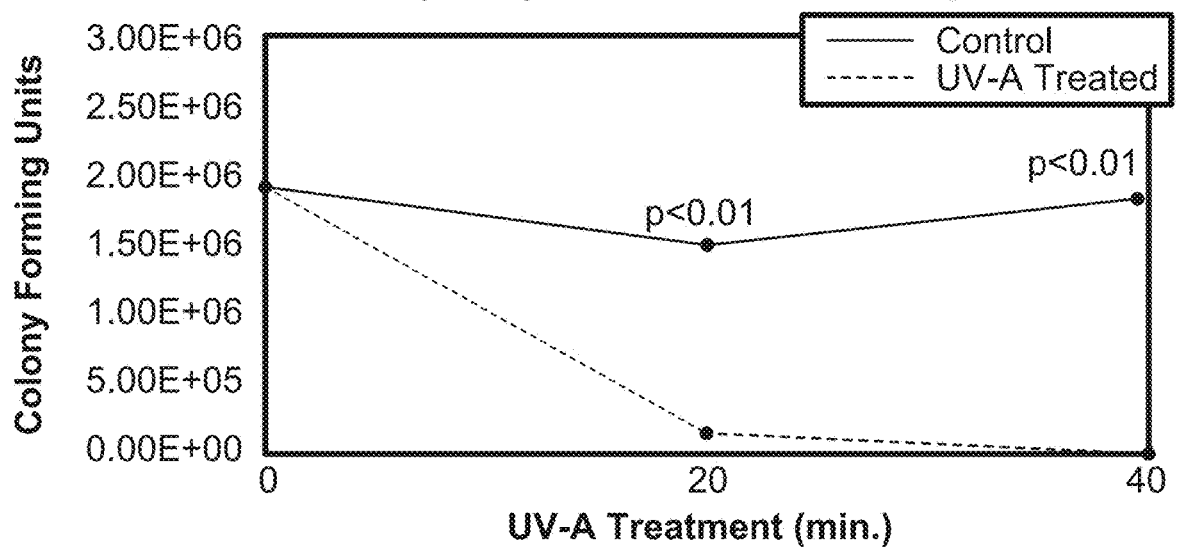
Figure 35G:
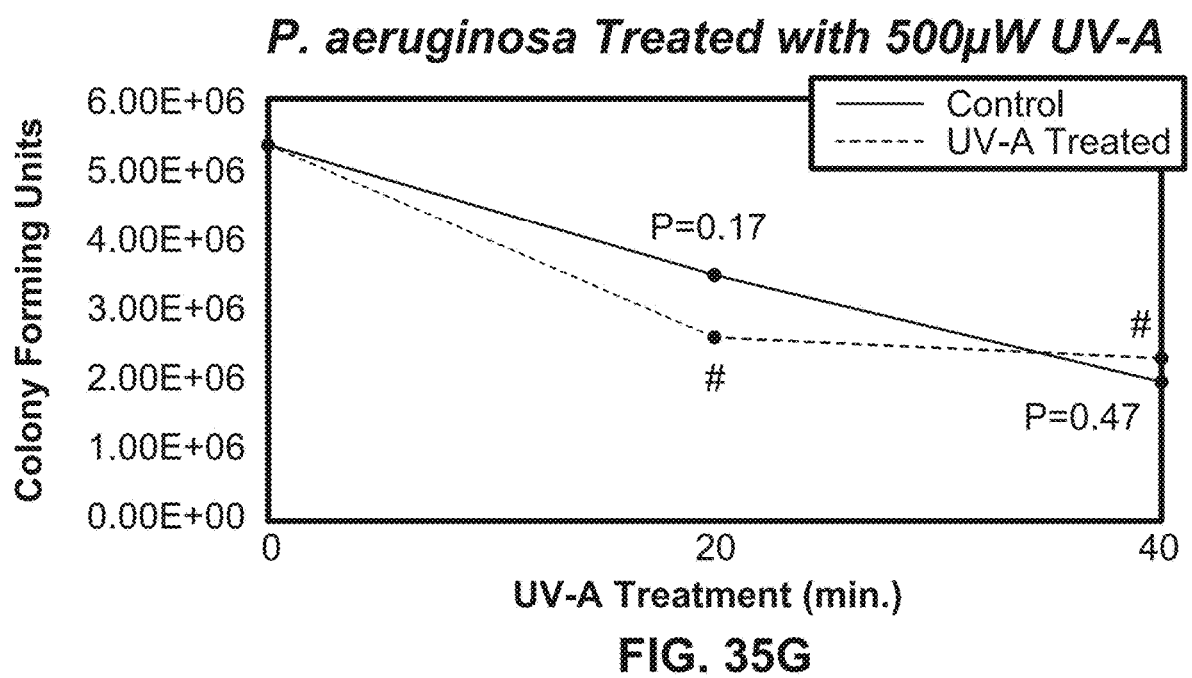
FIGS. 35G-35J illustrate growth curves showing *P. aeruginosa* bacterial counts over time exposed to various intensities of UV light using exemplary systems according to the present disclosure.
Figure 35H:
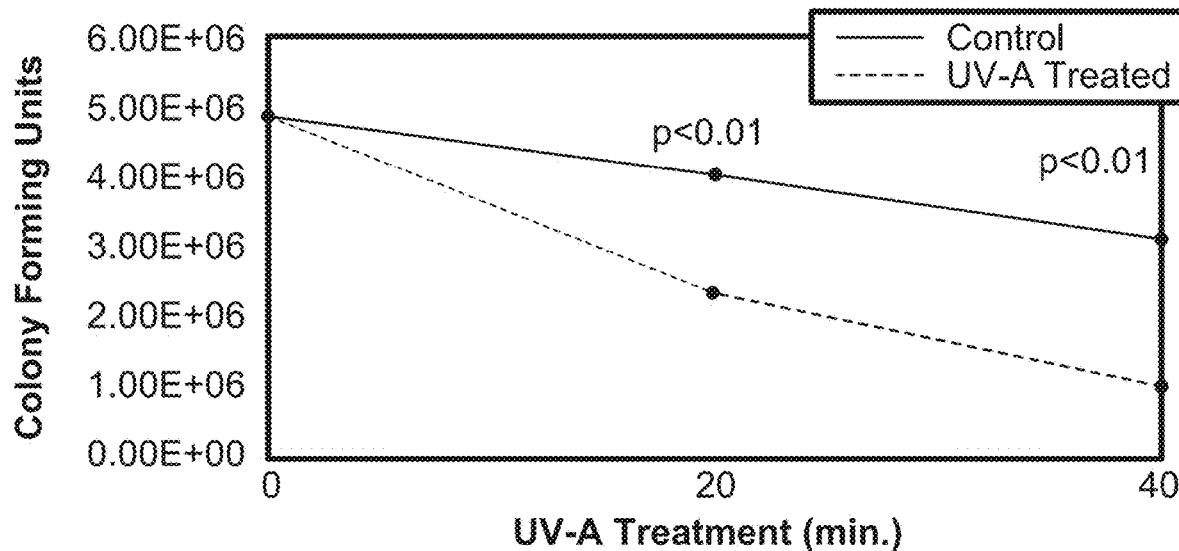

FIGS. 35B-35E illustrate graphs showing the change in colony forming units (CFUs) of *E. coli* over time when UV-A light with a peak wavelength of 345 nm is applied at various intensities. As illustrated most of the bacteria were eliminated by 40 minutes with an intensity of 2000 uW (FIG. 35D) and most of the bacteria were eliminated by 20 minutes with an intensity of 3000 uW (FIG. 35E). When the same light was applied at 500 uW and 1000 uW of intensity, there was significant reduction of CFUs by 40 minutes, but only by about half (FIG. 35C and FIG. 35B).

Figure 35I:
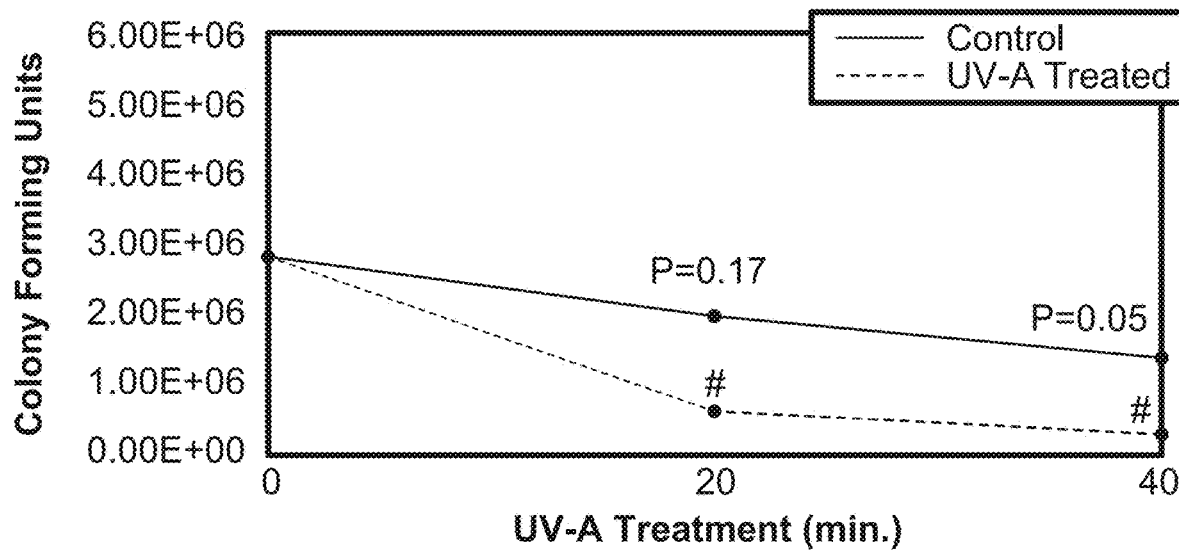
Figure 35J:
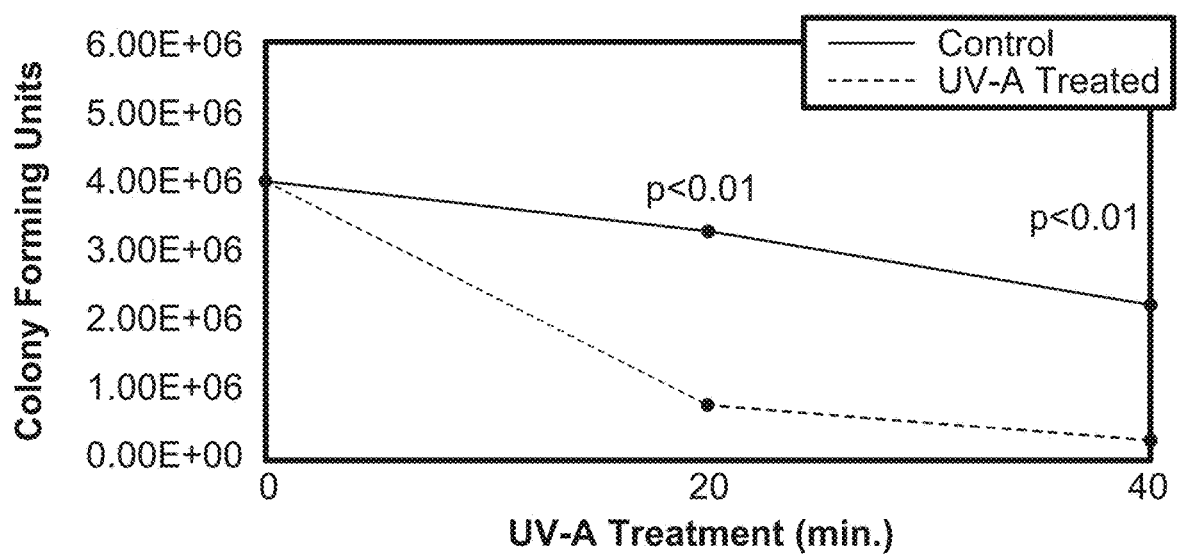

FIGS. 35G-35J illustrate graphs showing the change in colony forming units (CFUs) of *P. aeruginosa* over time when UV-A light with a peak wavelength of 345 nm is applied at various intensities. As illustrated, treatment with an intensity of 1000 uW, 2000 uW and 3000 uW showed significantly greater reduction in CFUs compared to control (FIG. 35H, FIG. 35I and FIG. 35J), and most of the bacteria were eliminated by 20 minutes with an intensity of 2000 uW and 3000 uW (FIG. 35I and FIG. 35J).

Figure 35K:
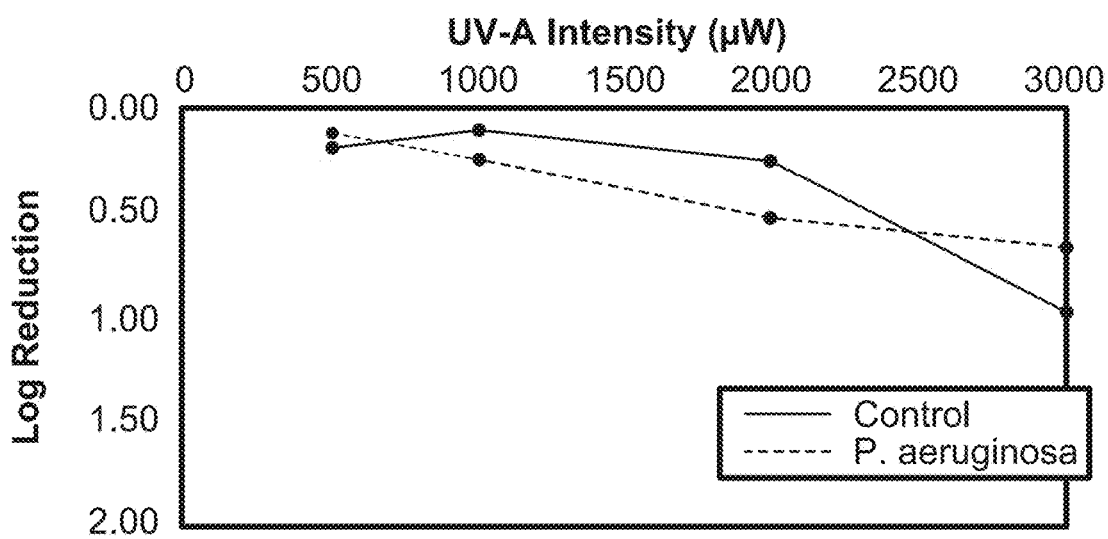
FIGS. 35K-35L illustrate growth curves comparing the logarithmic reduction at various intensities at 20 minutes and 40 minutes respectively using exemplary systems according to the present disclosure.
Figure 35L:
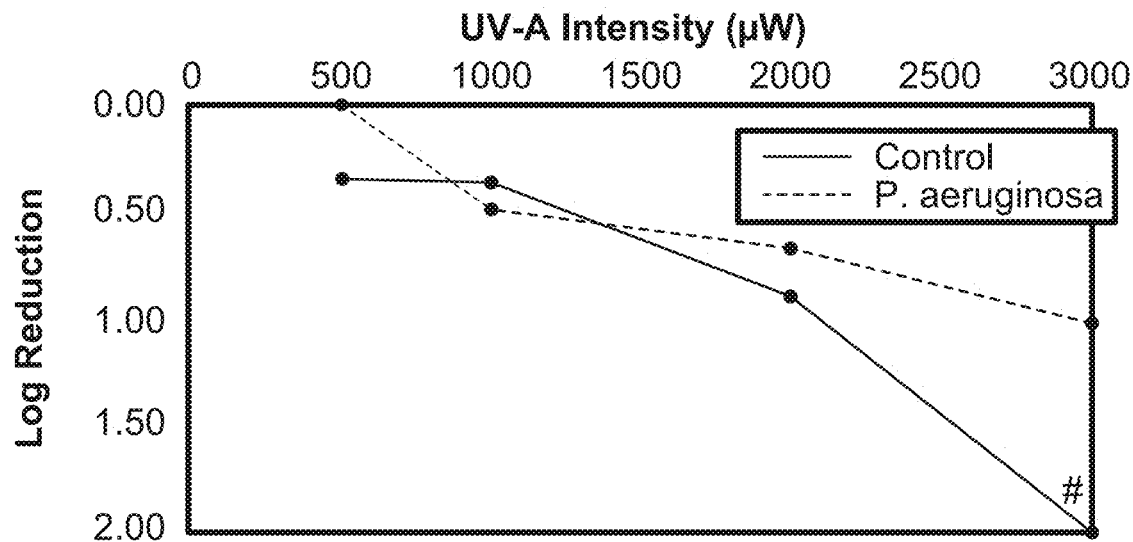
Figure 35M:
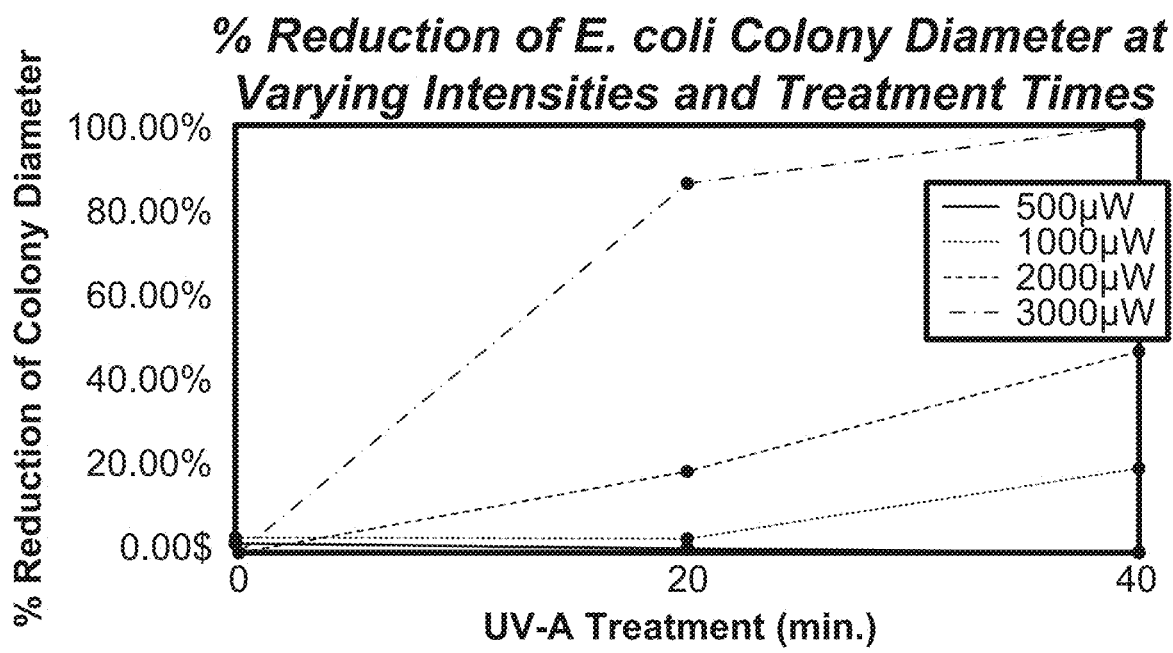
FIG. 35M illustrates growth curves showing the reduction of a *E. coli* colony diameter at various intensities and treatment times using an exemplary system according to the present disclosure.
Figure 35N:
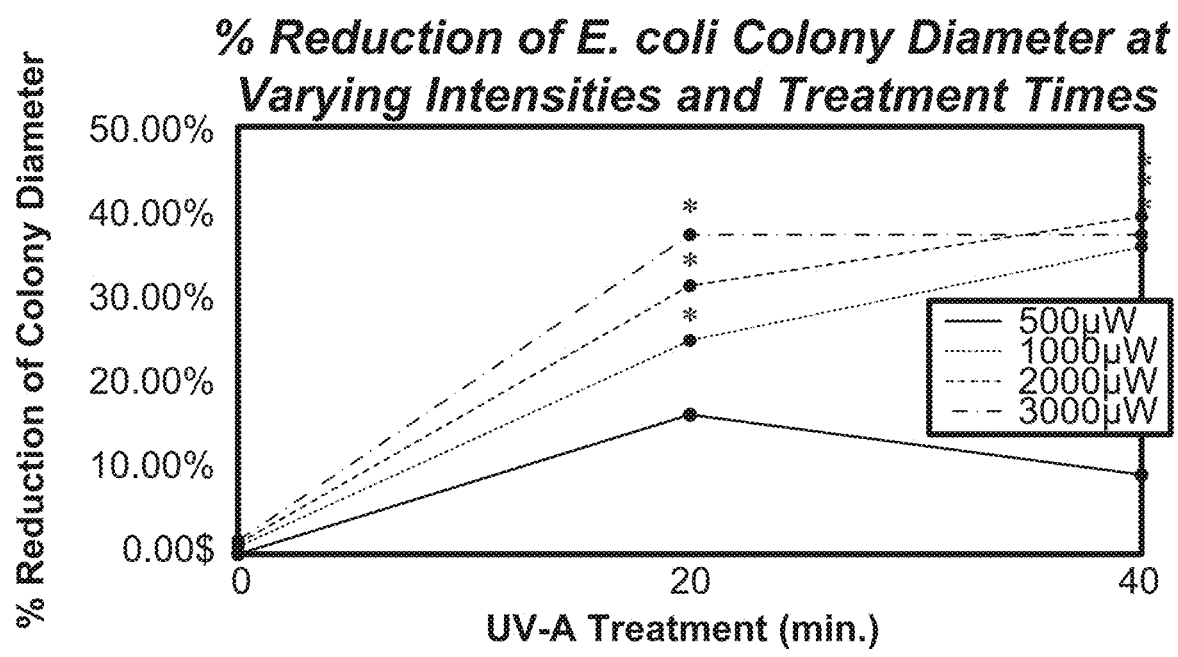
FIG. 35N illustrates growth curves showing the reduction of a *P. aeruginosa* colony diameter at various intensities and treatment times using an exemplary system according to the present disclosure.

FIGS. 35K-35L illustrate growth curves comparing the logarithmic reduction of *P. aeruginosa* at various intensities at 20 minutes and 40 minutes respectively. FIG. 35M illustrates growth curves showing the reduction of a *E. coli* colony diameter at various intensities and treatment times. FIG. 35N illustrates growth curves showing the reduction of a *P. aeruginosa* colony diameter at various intensities and treatment times.

Examining the effect of light intensity on the reduction of *E. coli* and *P. aeruginosa*, there was a dose response effect on both bacterial levels and colony size (FIGS. 35B-35N). The ideal UVA intensity to impact bacteria appeared to be between 2000 and 3000 µW/cm² when using a narrowband LED with a peak wavelength of 345 nm, and in some examples may depend on the bacteria or pathogen type and species, and other factors as disclosed herein.

Example 3: Safety Data

For the assessment of the safety of UVA on mammalian cells, three experiments were conducted. The first was the exposure of UVA to HeLa cells in culture. HeLa cells were added to DMEM cell culture medium (Gibco, Waltham, MA) plus 10% Bovine serum (Omega Scientific, Tarzana, CA) and 1× Antibiotic-Antimycotic (100× Gibco) in 60×15 mm cell culture dishes (Falcon) and incubated at 37° C. (5% CO2) for 24 hours to achieve 1,000,000 to 1,800,000 cells per plate. At this point cells were exposed to UVA LED light (1800 µW/cm²) for 0 (control), 10, or 20 minutes. After 24 hours, cells were removed by 0.05% Trypsin-EDTA (lx) (Gibco), stained with Trypan blue (Trypan Blue 0.4% ready to use (1:1) (Gibco)) and quantitated by automated cell counter (Biorad T20, Hercules, CA). In a similar experiment, the LED UVA light was used at a higher intensity (5000 µW/cm²) for 20 minutes. Once again, HeLa cells were quantitated at 24 hours following UVA exposure.

The safety of UVA was also studied in two human respiratory cell types. These included alveolar (ATCC A549) and primary ciliated tracheal epithelial cells (HTEpC) (PromoCell, Heidelberg, Germany). For each cell line, 250,000 cells were plated and grown for 48 hours in DMEM until the cell count per plate was approximately 750,000. At this point, cells were exposed to UVA (2000 µW/cm²) for 0 (control) or 20 minutes (treated), and cell counts were obtained at 24 hours later.

The levels of 8-hydroxy-2'-deoxyguanosineis (8-OHdG) was also analyzed in the DNA of cells treated with UVA. 8-OHdG is widely accepted as a sensitive marker of oxidative DNA damage and oxidative stress. DNA was extracted with the AllPrep DNA/RNA/Protein Mini Kit (Qiagen) following manufacturer's instructions. The levels of 8-OHdG was detected using the EpiQuik™ 8-OHdG DNA Damage Quantification Direct Kit following manufacturer's instructions (Epigentek, Farmingdale, NY). For optimal quantification, the input DNA amount was 300 ng, as the basal 8-OHdG is generally less than 0.01% of total DNA (Epigentek, Farmingdale, NY).

Wild type 129S6/SvEv mice (n=20, female=10) and BALB/cJ mice (n=10, female=5) were used for UVA light safety tests. All animals were anesthetized prior the procedure. Prior to the UVA light treatment, animals were placed in an induction chamber containing isoflurane anesthetic gas (1-5%). The carrier gas for isoflurane was compressed oxygen (100% oxygen). Once the respiratory rate had slowed (approximately one breath per second), the animals were removed from the induction chamber and maintained under sedation using a nose cone anesthesia (1-2% isoflurane). The depth of anesthesia was confirmed by lack of response to toe pinch.

Under anesthesia, customized rods (D=4 mm, L=40 mm) were introduced anally up to the splenic flexure. The same procedure was applied to the control group using an identical but unlit rod. Same light source and measurement equipment were used as described for liquid culture experiments.

In the first experiment, 5 BALB/cJ mice underwent colonic UVA exposure (2,000 $\mu W/cm^2$) for 30 minutes as compared to 5 mice treated with the same technique with an unlit optic rod.

In the second experiment, 10 129S6/SvEv mice underwent 20 minutes per day of colonic UVA exposure (3,000-3,500 $\mu W/cm^2$) for 2 two consecutive days as compared to 10 mice (male=5) treated with an unlit rod.

Colon Endoscopic Examination Before and After UVA Light Therapy

A rigid pediatric cystoscope (Olympus A37027A) was used to assess the intestinal mucosa before and after 7 days of UVA exposure. Endoscopy was performed in anesthetized animals. The method of sedation is described above.

The anus was first lubricated with a water-based gel (Astroglide®, BioFilm, Inc., Vista, CA, USA). The endoscope was then inserted to the splenic flexure, and the colon was insufflated using room air instilled via an endoscopic port. All endoscopies were recorded and blindly interpreted by two gastroenterologists with expertise in animal model endoscopies. Endoscopic appearances were analyzed based on perianal examination, transparency of the intestinal wall, mucosal bleeding, and focal lesions.

At day 14, control and treated mice were euthanized, and swiss-roll preparations of the entire colon were performed. Briefly, the entire colon was removed and rinsed in a modified Bouin's fixative solution (50% ethanol/5% acetic acid in dH2O). Using scissors, the colon was opened longitudinally along the mesenteric line and rinsed briefly in a Petri dish containing 1×PBS. The luminal side was identified and Swiss rolling of the opened tissue was performed. Once the entire colon length was rolled, the colon was carefully transferred to a tissue-processing/-embedding cassette. The cassette was placed in 10% buffered formalin overnight at room temperature, after which paraffin sections of the colon were cut, stained with hematoxylin and eosin (H&E), and assessed by a blinded pathologist (SS).

Data for bacterial counts between groups were not normally distributed and were therefore compared using non-parametric tests (Mann Whitney U test). Other quantitative data were compared by t-test using GraphPad Prism 7 (GraphPad, San Diego, CA).

Results

Figure 36A:
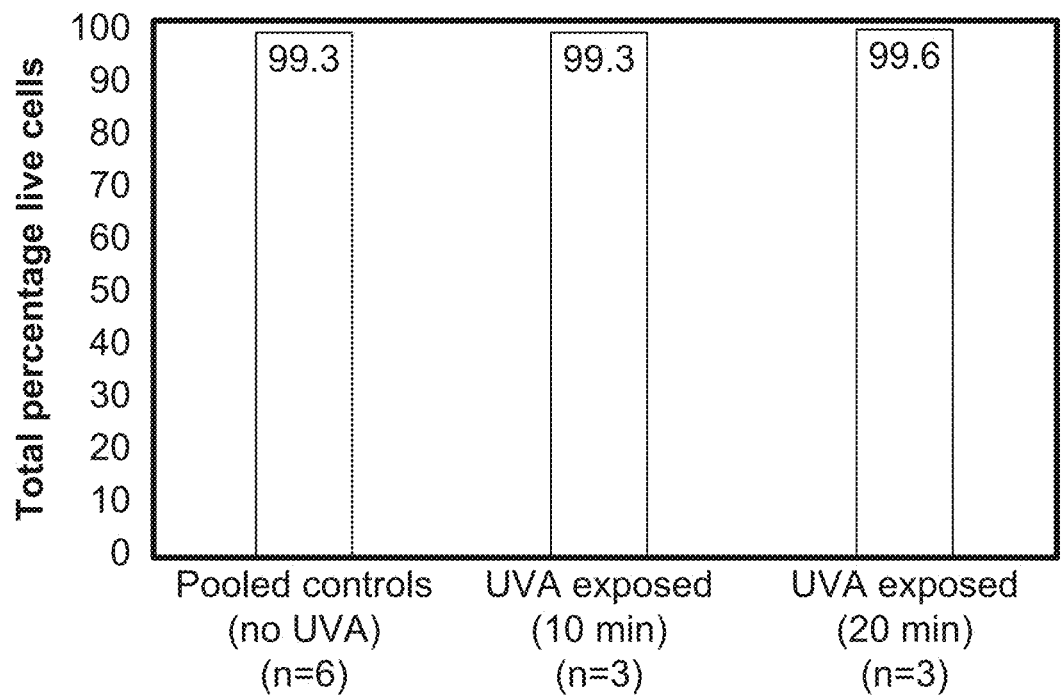
FIG. 36A illustrates a bar graph showing cell growth during exposure to UV-A light using an exemplary system according to the present disclosure.
Figure 36B:
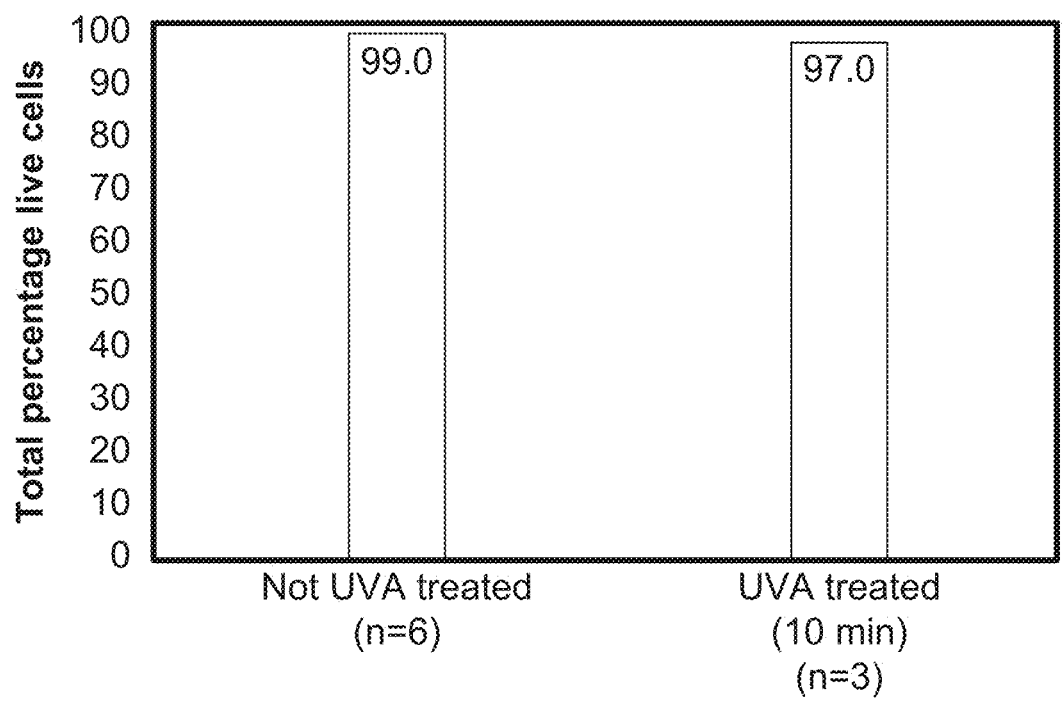
FIG. 36B illustrates a bar graph showing cell growth during exposure to UV-A light using an exemplary system according to the present disclosure.
Figure 36C:
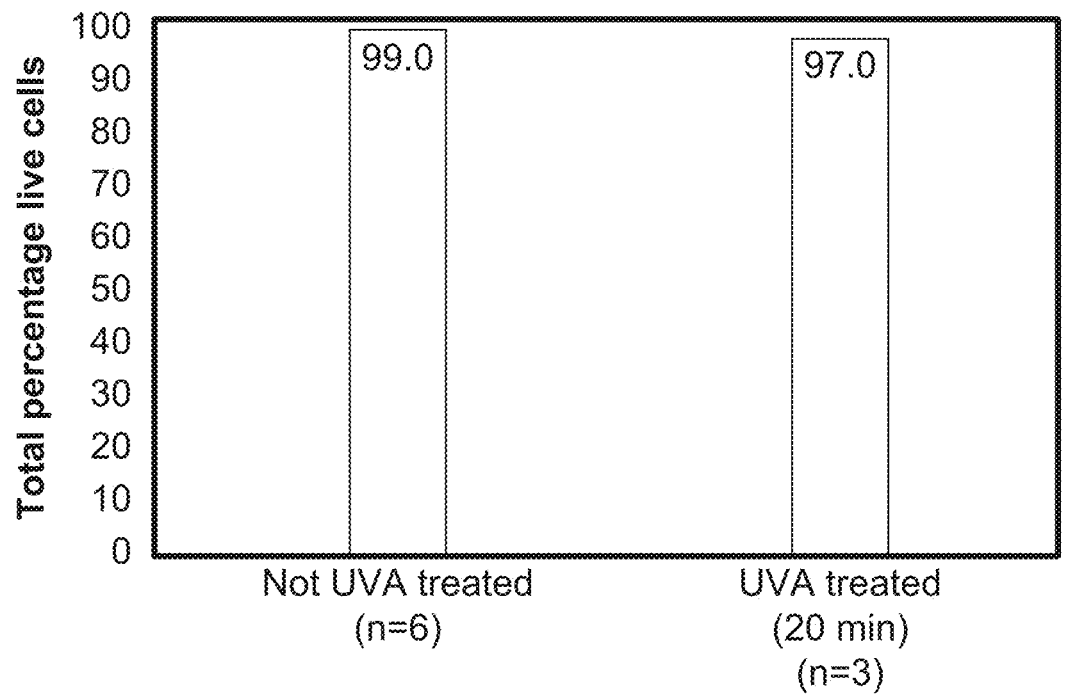
FIG. 36C illustrates a bar graph showing cell growth during exposure to UV-A light using an exemplary system according to the present disclosure.

Overall, based on cell growth over time, LED UVA appeared safe in the mammalian cells tested (HeLa, alveolar A549 and primary tracheal cells). All plates demonstrated continued cell growth, regardless of UVA exposure, with 1.5 to 2 times the number of cells per plate compared to controls, indicating robust ongoing replication. In the case of HeLa cells, UVA did not affect the number of live cells at 24 hours when compared to unexposed controls (P=0.99 and P=0.55 for 10 min and 20 min of ~2000 $\mu W/cm^2$ UVA, respectively) as shown in FIG. 36A. Higher intensity UVA (5000 $\mu W/cm^2$) did not affect the growth of HeLa cells as shown in the bar graph depicted in FIG. 36B. Similar findings were also seen with alveolar cells at 2000 $\mu W/cm^2$ for 20 min (P=0.99) as shown in FIG. 36C. Finally, ciliated epithelial cell growth was also unaffected by UVA after 20 minutes of exposure to ~1000 $\mu W/cm^2$ and to 2000 $\mu W/cm^2$.

Figure 36D:
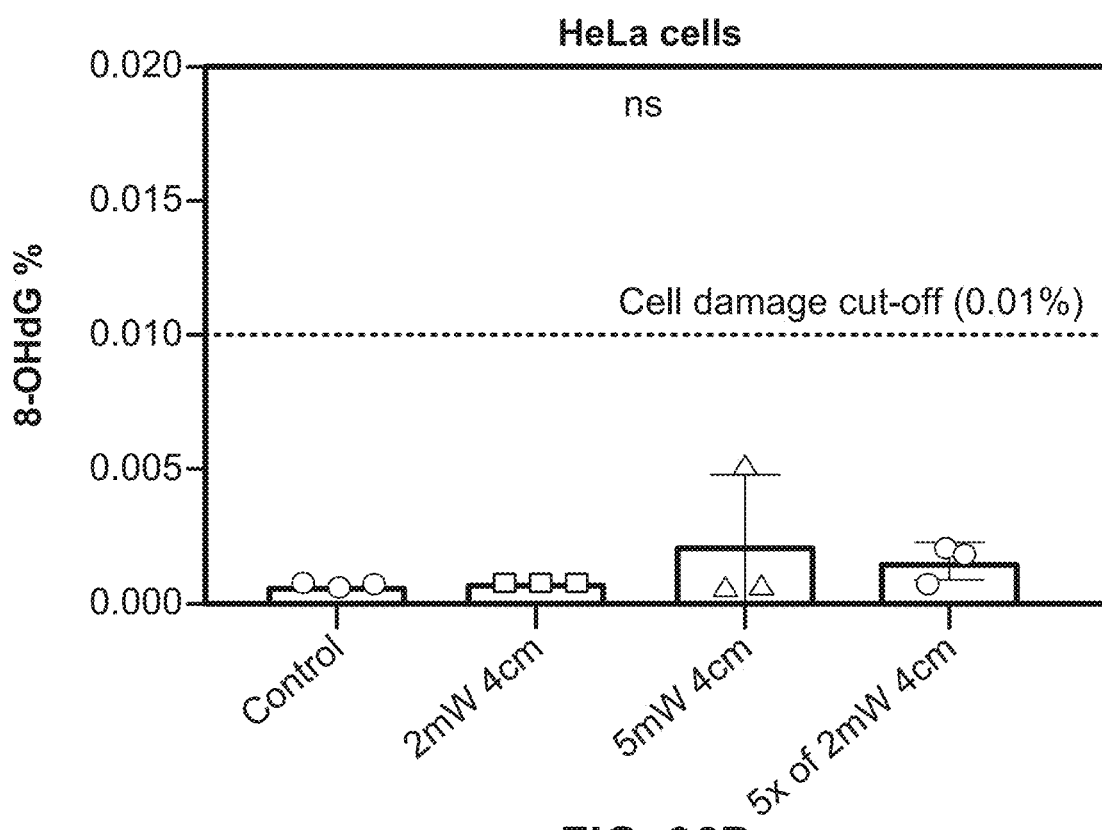
FIG. 36D illustrates a bar graph showing the absence of DNA damage to cells during exposure to UV-A light using an exemplary system according to the present disclosure.
Figure 36E:
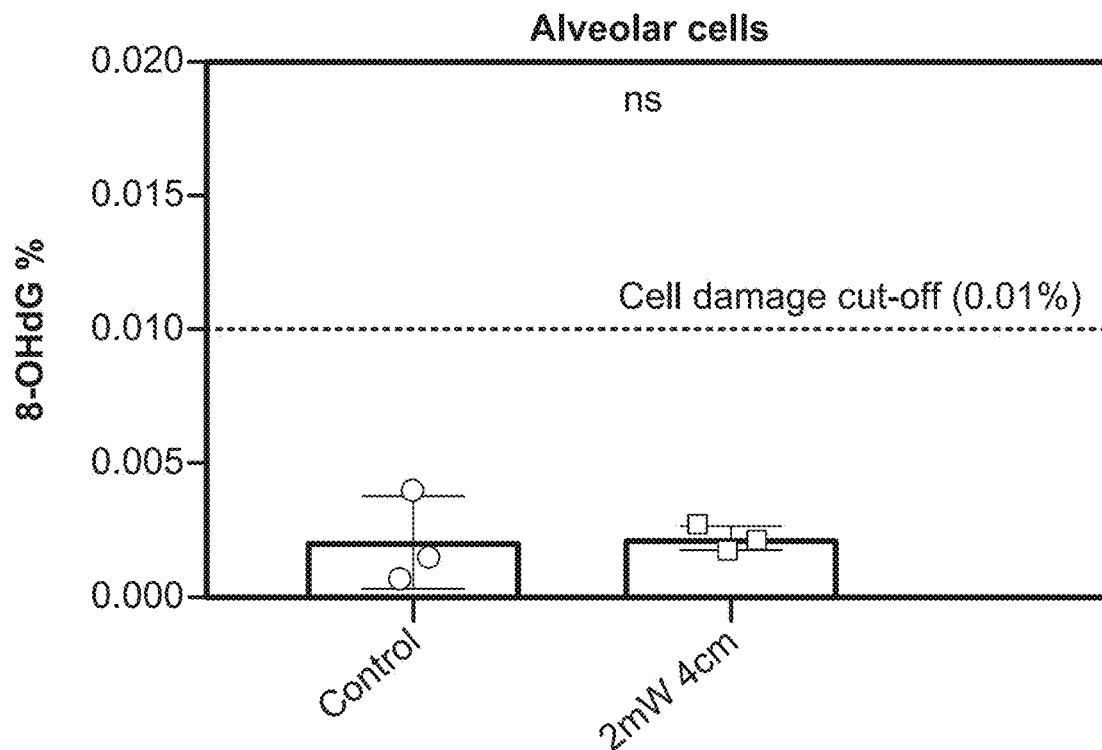
FIG. 36E illustrates a bar graph showing lack of DNA damage to cells during exposure to UV-A light using an exemplary system according to the present disclosure.
Figure 36F:
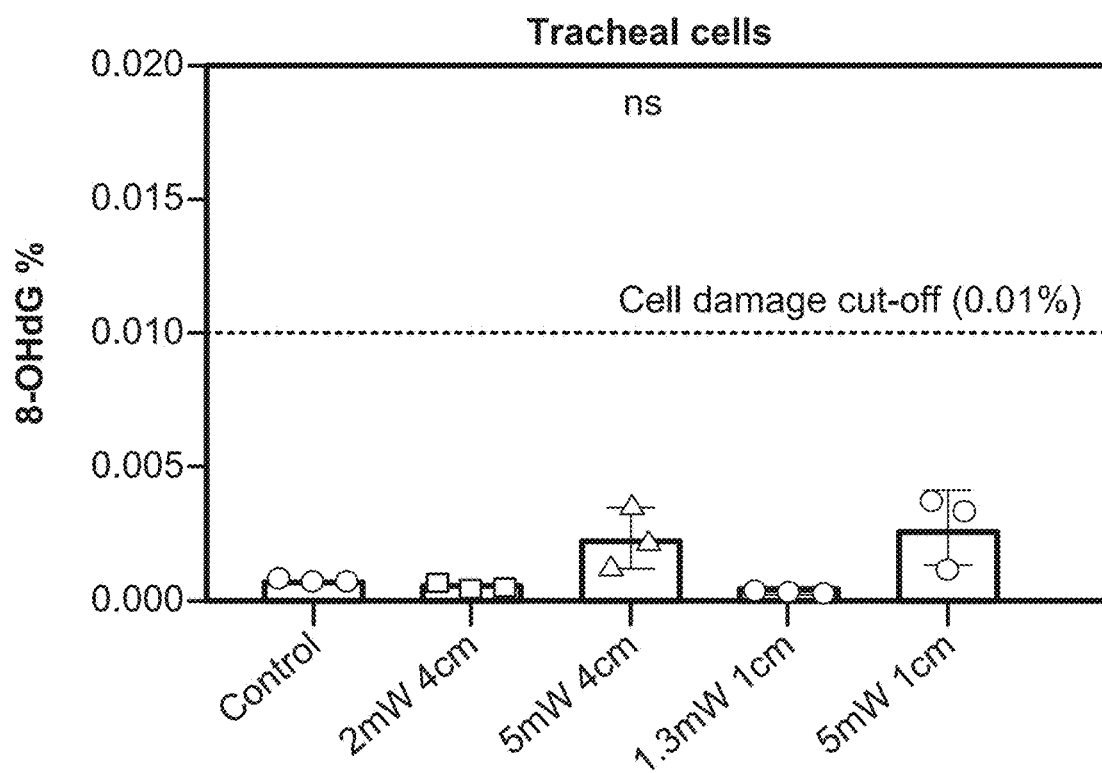
FIG. 36F illustrates a bar graph showing lack of DNA damage to cells during exposure to UV-A light using an exemplary system according to the present disclosure.
Figure 37:
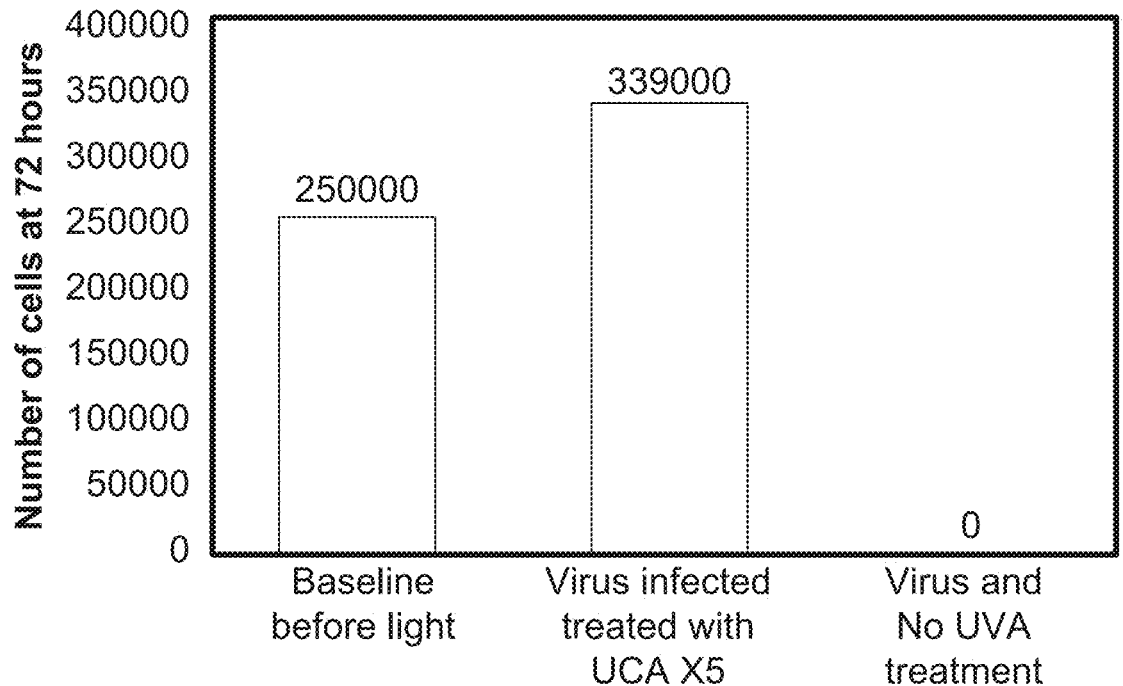
FIG. 37 illustrates a bar graph showing cell growth infected with a virus during exposure to UV light using an exemplary system according to the present disclosure.
Figure 38:
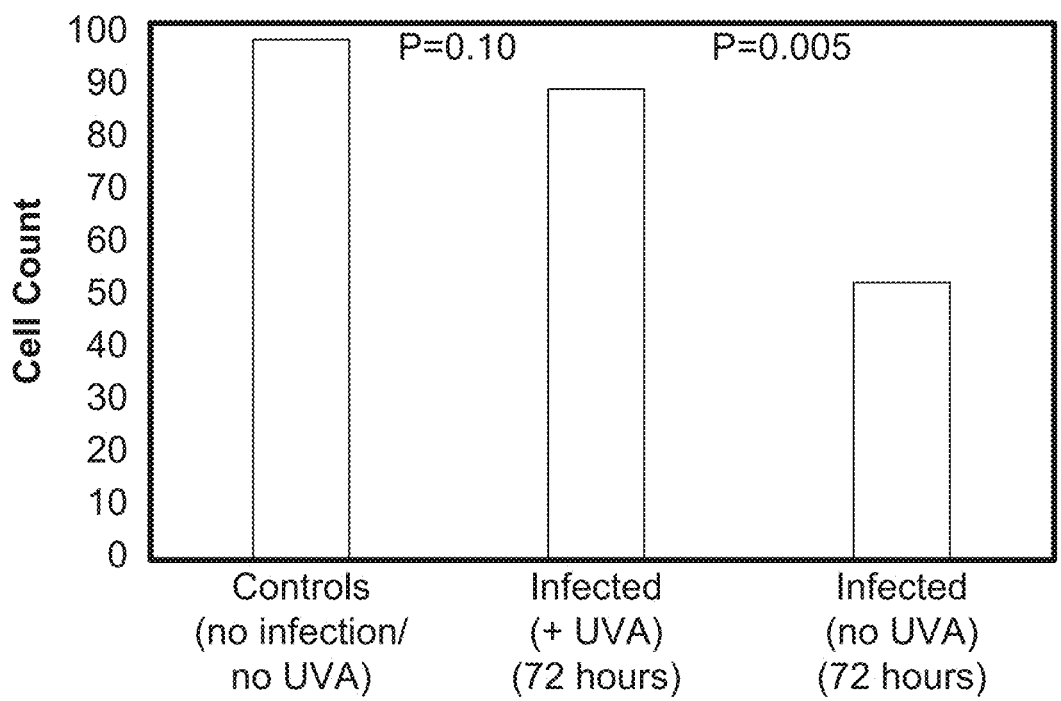
FIG. 38 illustrates a bar graph showing the cell counts of infected cells after 72 hours of UV light application compared to controls using an exemplary system according to the present disclosure.

Moreover, exposure to UVA did not cause DNA damage in any cell line analyzed, and the levels of 8-Oxo-2'-deoxyguanosine (8-OHdG) in cells treated with narrow-band LED UVA was similar to controls not exposed to UVA (P<0.05) as shown in FIG. 36D (HeLa cells), FIG. 36E (Alveolar cells), and FIG. 36F (Tracheal cells). Higher intensity LED UVA (5000 $\mu W/cm^2$) appeared to increase the levels of 8-OHdG (P=0.07) but the percentage of 8-OHdG remained well below the generally accepted threshold of 0.01% of the total DNA.

UVA Light Exposure is not Associated with Endoscopic or Histologic Injury

To assess the safety of UVA therapy on internal visceral cells and tissues, two different wild-type strains of mice were exposed to intracolonic wide-spectrum UVA light using optical rods designed to homogenously side-emit broad-spectrum UVA. Only the left side of the colon up to the splenic flexure were exposed to UVA light; hence, the unexposed right side served as a self-control. In the first experiment, under anesthesia, 5 mice underwent colonic UVA exposure (2,000 μW/cm2) for 30 minutes as compared to 5 mice treated with the same technique with an unlit optic rod.

In the second experiment, 10 mice (129S6/SvEv, male=5) underwent 20 minutes per day of colonic wide spectrum UVA exposure (3,000-3,500 $\mu W/cm^2$) for 2 two consecutive days as compared to 10 mice (male=5) treated with an unlit rod. No perforation, bleeding or fatalities were seen in any of the experiments. The mouse colonoscopy images show no change before and after UVA exposure.

In both experiments, endoscopic evaluation of mice before and after UVA administration demonstrated no macroscopic evidence of mucosal erythema, friability, ulceration or bleeding. Assessed by a blinded pathologist (SS), no chronic/acute inflammation, cystitis, crypt abscesses, granulomata, ulceration or dysplasia was seen on examined full-thickness colonic specimens exposed to wide spectrum UVA as compared controls and untreated segments of the colon.

RNA Virus Experimental Data

Additionally, the disclosed systems and methods were utilized to obtain experimental data in treating various RNA viruses with UVA light. Accordingly, the data illustrates that UV-A light emitted from an LED with a peak wavelength of 340 nm, can kill RNA viruses like Coxsackievirus. For instance, the Hela cells infected with Coxsackievirus survived when this UV-A treatment was applied, but did not survive when there was no UV-A light treatment applied after infection. Furthermore, the experimental data demonstrated only a 15% loss of UV-A light once it passed through an ET Tube.

In late December 2019, an outbreak of a novel coronavirus disease (SARS-CoV-2 or COVID-19; previously known as 2019-nCoV) was reported in Wuhan, China. COVID-19 is a viral infection that replicates efficiently in the upper respiratory tract. As part of the mechanism of action, the virus infects ciliated tracheal epithelial cells, which then slough off and compromise alveolar function. Secondary bacterial infections have also been noted, and both of these processes can lead to further inflammation, acute respiratory distress syndrome (ARDS), and ultimately, death. It is estimated that 10-15% of those infected have a severe clinical course and about 5% become critically ill, requiring mechanical ventilation for failure of the respiratory and other organ system. The case fatality rate of COVID-19 has been estimated to range from 0.5% to 9.5%, although these estimates are confounded by preferential testing of symptomatic patients and a lag time of up to 14 days for symptom presentation. Death is thought to be due to respiratory failure in the setting of ARDS and/or secondary infections including ventilator associated pneumonia (VAP).

Ventilator-associated pneumonia (VAP) may develop in intensive care unit (ICU) patients who are mechanically ventilated for at least 48 hours, which is common in COVID-19 patient. The incidence of VAP ranges broadly from 5% to 67%, depending on the diagnostic criteria used and patient population studied. Causative organisms include Enterobacteriaceae (25%), *Staphylococcus aureus* (20%), *Pseudomonas aeruginosa* (20%), *Haemophilus influenza* (10%), and streptococci (13). Multi-drug resistant bacteria are more common among late-onset cases. Mortality attributed to early-onset VAP is thought to be approximately 6% while that for late-onset VAP is 10%.

Currently, there is no treatment for COVID-19 and conventional means to reduce secondary infections in mechanically ventilated patients have proven insufficient to date. A safe and effective broad antiviral and antibacterial approach to these patients would potentially reduce viral burden, secondary infection and VAP, time on mechanical ventilation, and death due to respiratory failure.

As disclosed herein, ultraviolet (UV) light has antibacterial properties. UVC (110-280 nm) is widely used for industrial sterilization (16), but has harmful effects on human DNA. External UVA (320-400 nm) and UVB (280-320 nm) devices have FDA-approved indications to treat human diseases such as psoriasis, eczema, and skin lymphoma. These wavelengths penetrate the mucosal and submucosal tissue. Of the three spectrums, UVA appears to cause the least damage to mammalian cells. Presently, there are no studies showing the effects of an internal application of UVA light for bacterial or viral infections. Advances in light emitting diodes (LEDs) are making it feasible to apply narrow-band UVA to internal organs.

Accordingly, disclosed is experimental data illustrating the effects of broad and/or narrow band UVA for the treatment of common bacterial pathogens known to be associated with VAP. Additionally, disclosed is data that demonstrates on the effects of a specific wavelength of UVA on group B coxsackievirus and coronavirus 229E. Finally, further data demonstrates the safety of UVA exposure for mammalian cells and in vivo epithelial cells.

Example 4: Coxsackievirus

Coxsackievirus Sample Obtainment and Infection into Cells

Recombinant coxsackievirus B (pMKS1) expressing enhanced green fluorescent protein (EGFP-CVB) plasmid was linearized using ClaI restriction enzyme (ER0142, Thermo Fisher) and linearized plasmid was purified using standard phenol/chloroform extraction and ethanol precipitation. Viral RNA was then produced using mMessage mMachine T7 Transcription kit (AM1344, Thermo Fisher). Viral RNA was then transfected into HeLa cells (~80% confluency) using Lipofectamine 2000 (11668027, Thermo Fisher). Once cells exhibited ~50% cytopathic effect, cells were scraped and the cell/media suspension was collected. This mixture was then subjected to three rounds of rapid freeze-thaw cycles and centrifuged at 1000×g for 10 minutes to clarify media of cellular debris. Supernatant was used as passage 1 viral stock. The passage 1 viral stock was then overlain onto separate HeLa cells (~80% confluency) to expand the stock into passage 2 viral stock which was used for subsequent experiments.

UVA Treatment on HeLa Cells Infected with Group B Coxsackievirus

HeLa cells were used for four different experiments with enhanced green-fluorescent protein (EGFP)-expressing group B coxsackievirus (EGFP-CVB). In the first experiment, HeLa cells (253,000 per plate) (n=12 plates) were cultured for 24 hours. Half of the EGFP-CVB aliquots were exposed to LED UVA (2000 $\mu W/cm^2$; peak wavelength of 340 nm) for 20 minutes while the other was not exposed; HeLa cells were then infected with either UVA-exposed or UVA-unexposed virus (MOI=0.1). Six hours later, the supernatant was removed, and the cells were washed twice with 1× sterile PBS (pH=7.0). New DMEM media was added. Plates that were infected with UVA-exposed virus received an additional 20 minutes of UVA (2000 $\mu W/cm^2$) exposure. Dead cells in the supernatant were collected and quantified 24 hours later. Six plates (3 each of UVA and non-UVA treated) were assessed for live cells. Of the remaining six plates, the 3 plates which had initially been exposed to UVA with a peak wavelength of 340 nm were then exposed to an additional 20 minutes of UVA (2000 $\mu W/cm^2$). After an additional 24 hours, dead and live cells counts were obtained from the remaining plates.

HeLa Cell Pre-Treatment with UVA on Group B Coxsackievirus Infection

In the second experiment, HeLa cells (235,000 cells) were plated and then incubated in DMEM for 24 hours. The plates were then divided into unexposed controls (n=3) and exposed to LED UVA (2000 $\mu W/cm^2$; peak wavelength of 340 nm) for 20 minutes (n=3). After another 24 hours, all plates were infected with EGFP-CVB (MOI=0.1). After an additional 24 hours, cells were counted as previous described.

Pre-Treatment of Group B Coxsackievirus with UVA on HeLa Cell Infection

In the third experiment, HeLa cells were cultured for 24 hours and then infected with EGFP-CVB (MOI=0.1). Just prior to infection, half of the EGFP-CVB aliquots were exposed to LED UVA (2000 $\mu W/cm^2$; peak wavelength of 340 nm) and the other half remained unexposed. Twenty-four hours later, a viable cell count was obtained.

Long-Term UVA Treatment of HeLa Cells During Ongoing Group B Coxsackievirus Infection In this experiment, 250,000 HeLa cells were plated. At 24 hours, cells were divided into three groups. In the first group, cells were infected with EGFP-CVB (MOI=0.1). These cells served as positive infected controls. In group 2, HeLa cells were infected with UVA-treated (2000 µW/cm2 for 20 min; peak wavelength of 340 nm) EGFP-CVB (MOI=0.1) and 6 hours later the infected cells were treated with UVA (2000 $\mu W/cm^2$; peak wavelength of 340 nm) for 20 minutes followed by 4 additional treatments including day 2 for 20 minutes twice 8 hours apart, and day 3 twice for 20 minutes, 8 hours apart. Group 3 was not infected with EGFP-CVB but was treated 5 times with UVA at the same timepoints used for group 2. This was the non-infected positive control to demonstrate safety of UVA. In all conditions, imaging and cell counts were obtained.

UVA Treatment on Alveolar (A549) Cells Infected with Group B Coxsackievirus

Ideal timepoints of cell death from infection were determined in preliminary experiments with alveolar cells to be 48 hours after infection. In this study, 200,000 alveolar cells were plated and counted at 48 hours (cell count of 754,000).

Alveolar cells were then infected with EGFP-CVB (MOI=0.1). Twenty-four hours after infection, the alveolar cell plates were exposed to LED UVA (2000 μW/cm$^2$; peak wavelength of 340 nm) for 0 (control) or 20 minutes (treated) and this was repeated every 24 hours for three days with imaging and cell counts at 96 hours post-infection.

Results

UVA pre-treatment of Group B coxsackievirus only prior to infection of HeLa cells does not mitigate infection In this experiment, half of the plates with HeLa cells were treated with EGFP-CVB and the other half were treated with Group B coxsackievirus that was exposed to ~2000 μW/cm$^2$ LED UVA light with a peak wavelength of 340 nm for 20 minutes. The effect on infection rates at 24 hours were not different between groups.

UVA pre-treatment of HeLa cells prior to Group B coxsackievirus infection does not mitigate viral effects In this experiment, half of the plates with HeLa cells were left untreated and the other half were pre-treated with ~2000 μW/cm$^2$ LED UVA; peak wavelength of 340 nm for 20 minutes with no further UVA treatment. EGFP-CVB was added to both groups. Both groups were equally infected, suggesting that treating HeLa cells before infection did not influence the infection rate.

UVA Treatment after Infection with Group B Coxsackievirus Reduced Viral Effect on HeLa Cells In this study, UVA was applied after the HeLa cells were infected with EGFP-CVB. Treated cells were exposed to 2000 μW/cm$^2$ LED UVA with a peak wavelength of 340 nm at 6 hours post-infection, then twice daily for two additional days, with cell counts at 72 hours post-infection. This was compared to infected but untreated controls. In the treated group, UVA light prevented cell death from EGFP-CVB, with increased cell counts to 339,333±60,781 at 72 hours as shown in the bar graph depicted in FIG. 37, compared to no live cells remaining on plates at 48 and 72 hours in untreated controls. Importantly, a third group of HeLa cells that were not infected but received UVA exposure at the same time intervals showed normal cell proliferation, with a cell count of 2,413,333±403,773 at 72 hours.

The Effect of UVA Treatment on Alveolar (A549) Cells Infected with Group B Coxsackievirus In alveolar cells infected with EGFP-CVB, cell death was far less than that seen in HeLa cells. At 96 hours post infection, there was clear and widespread infection of cells in the control group. Alveolar cells treated with LED UVA with a peak wavelength of 340 nm also demonstrated infection, but visual assessment suggested a lower rate of infection, with far fewer cells producing viral EGFP signals. In addition, viable cell counts appeared to be higher in the UVA treated group when compared to the untreated group.

Example 5: Coronavirus

In another example, coronavirus infected ciliated tracheal epithelial cells (HTeC) were treated with UV light as disclosed below.

Ciliated tracheal epithelial cells (Promocell, Heidelberg, Germany) were plated (135,000 per plate) into three groups. One group was infected with coronavirus 229E (Cov-229E) (50 uL per plate). In the other group, just prior to infection, coronavirus 229E was treated with LED UVA with a peak wavelength of 340 nm (2000 μW/$cm^2$) for 20 minutes. A third group received no infection or UVA. After infection, the cells were treated with UVA (4 cm distance with 2000 μW/$cm^2$ at surface of plate with a peak wavelength of 340 nm) for 20 minutes daily. Plates were imaged at 16, 72 and 96 hours, and cell counts were obtained at 72 and 96 hours after infection.

UVA to Salvage Already Infected (with Coronavirus 229E) Ciliated Tracheal Epithelial Cells In this experiment, plates of ciliated tracheal epithelial cells (HTeC) were infected with Cov-229E as above. At 24 hours, plates were divided into two groups. Group 1 was left to continue the infection. In group 2, plates were treated with UVA with a peak wavelength of 340 nm (4 cm distance with 2000 μW/$cm^2$ at surface of plate) for 20 minutes. At 48 hours, plates were imaged, and viable cell counts were obtained.

UVA to Treat Coronavirus Infected Ciliated Tracheal Epithelial Cells at Close Range In the anticipation of an endotracheal device using UVA technology, another experiment was conducted identical to the above experiments using lower intensity of light (1300 μW/$cm^2$ at the surface of the plate from only 1 cm distance) for 20 minutes daily. This would be the anticipated distance between a light catheter and the tracheal cells in the ventilated patient from the inside of an endotracheal tube.

Level of Coronavirus in Cells with or without UVA Treatment

AllPrep DNA/RNA/Protein Mini Kit (Qiagen) was used to extract total protein from cell samples. Proteins were loaded into a Bolt 4-12% Bis-Tris gel (NW04122 Thermo Fisher) and transferred onto a Biotrace NT nitrocellulose membrane (27376-991, VWR). Total proteins were stained with Ponceau S solution (P7170, Sigma-Aldrich). The membrane was then blocked in blocking solution (tris-buffered saline containing 3% bovine serum albumin (A7030, Sigma-Aldrich) and 0.1% Tween 20 (P1379, Sigma-Aldrich). The membrane was then incubated overnight at 4° C. with either rabbit anti-coronavirus spike protein antibody (1:1000; PA5-81777, Thermo Fisher) or mouse anti-MAVS (mitochondrial antiviral signaling) antibody (1:200; SC-166583, Santa Cruz Biotechnology) diluted in blocking solution. After washing in tris-buffered saline+0.1% Tween 20 (TB S-T), the membrane was then overlain with either horseradish peroxidase (HRP)-conjugated goat anti-rabbit IgG antibody (1:300; 95058-734, VWR) or HRP-conjugated goat anti-mouse IgG antibody (1:300; 5220-0286, SeraCare). The membrane was then washed in TBS-T and subsequently exposed to enhanced chemiluminescence solution (RPN2235, GE Healthcare). Immunoreactive protein bands were imaged using a ChemiDoc Imaging System (Bio-Rad Laboratories, Hercules, CA USA).

LED UVA Light Preserves Ciliated Tracheal Epithelial Cells Infected with Coronavirus 229E Pre-treatment of ciliated tracheal epithelial cells with coronavirus 229E and daily LED UVA (2000 μW/$cm^2$; peak wavelength of 340 nm) for 20 minutes was compared to control cells (no UVA and no infection) and cells infected with coronavirus but no UVA exposure. Direct visualization showed definitive changes in cell morphology with infection (no UVA). However, control cells and infected cells treated with daily UVA exhibited similar morphology. At 96 hours, the supernatant was removed and the viable cells (adherent to the plate) were counted. There was no difference in tracheal cell number between control and infected cells treated with UVA. However, there was a marked reduction in viable cells among those infected compared to UVA treated cells (P=0.005) as illustrated in the bar graph shown in FIG. 38.

Interestingly, infected cells treated with LED UVA revealed decreased Cov-229E spike (S) protein (~130 kDa)

when compared to the infected cells not treated. Moreover, the levels infected with Cov-229E and treated with UVA had increased levels of MAVS when compared to cells infected with Cov-229E but not treated with UVA.

Accordingly, the experimental data confirms that UV-A light will kill coronavirus 229 E after infecting the epithelial lung tissue, and validates its application in conjunction with ET Tubes and other devices to irradiate the lung tissues as a treatment for coronavirus infected patients.

CONCLUSION

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Certain embodiments of this application are described herein. Variations on those embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

Particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

The invention claimed is:

1. A system for performing intra-corporeal ultraviolet therapy on a subject, the system comprising:

a delivery tube adapted to be positioned inside an intra-corporeal cavity of a subject, wherein the intra-corporeal cavity is a rectum, vagina, urethra, urinary tract, bladder, sigmoid, colon, anus, mouth, esophagus, gastroesophageal junction, stomach, intestines, or biliary tract; and at least one ultraviolet (UV) light source connected to the delivery tube positioned to deliver UV light outward from the delivery tube, wherein the at least one UV light source is configured to emit the UV light at wavelengths between 335 nm and 349 nm;

wherein a temperature of the delivery tube does not exceed 40° C.; and wherein the at least one ultraviolet (UV) light source is a light emitting diode (LED) or a string of LED light sources.

2. The system of claim 1, wherein the at least one ultraviolet (UV) light source is multiple ultraviolet (UV) light sources.

3. The system of claim 1, wherein the delivery tube is rigid or flexible.

4. The system of claim 1, wherein the delivery tube comprises a biocompatible polymer or a polymer having a biocompatible coating.

5. The system of claim 1, wherein the delivery tube comprises an outer surface, wherein the outer surface is selected from borosilicate glass, silicon, silica, polyurethane, polyethylene, or polytetrafluoroethylene (PTFE).

6. The system of claim 1, wherein the delivery tube is partially coated with borosilicate glass.

7. The system of claim 1, wherein the delivery tube comprises a proximal end and a distal end.

8. The system of claim 7, wherein the distal end is configured for insertion into the intra-corporeal cavity of the subject.

9. The system of claim 7, wherein the proximal end is configured for maneuvering the delivery tube.

10. The system of claim 7, further comprising a gripping element, wherein the gripping element is attached to the proximal end.

11. The system of claim 7, wherein the delivery tube comprises a rotating base at the distal end.

12. The system of claim 1, further comprising a memory; and a control system coupled to the memory and comprising one or more processors, the control system configured to execute machine executable code to cause the at least one UV light source to emit wavelengths between 335 nm 349 nm.

13. The system of claim 1, further comprising a power source to power the system.

14. The system of claim 1, wherein the delivery tube comprises four-sides.

15. The system of claim 14, wherein the at least one ultraviolet (UV) light source is positioned on each side of the delivery tube.

16. The system of claim 1, wherein the delivery tube is a catheter.

17. The system of claim 1, wherein the delivery tube is an endoscope.

18. The system of claim 1, wherein the intra-corporeal cavity is a vagina, rectum, sigmoid, colon, or anus.

19. The system of claim 1, wherein the intra-corporeal cavity is a mouth, esophagus, gastroesophageal junction, stomach, intestines, or biliary tract.

20. A method of treating a subject for an infectious condition inside the subject's body, the method comprising:
    obtaining a system of claim 1;
    inserting a delivery tube of the system inside an intra-corporeal cavity of a subject, wherein the intra-corporeal cavity is a rectum, vagina, urethra, urinary tract, bladder, sigmoid, colon, anus, mouth, esophagus, gastroesophageal junction, stomach, intestines, or biliary tract, and wherein the system comprises at least one ultraviolet (UV) light source connected to the delivery tube positioned to deliver UV light outward from the delivery tube, wherein the at least one UV light source is configured to emit the UV light at wavelengths between 335 nm and 349 nm; and
    emitting UV light at wavelengths between 335 nm and 349 nm from the at least one ultraviolet (UV) light source connected to the delivery tube to deliver UV wavelengths outward from the delivery tube for a threshold duration and a threshold intensity to treat the infectious condition.

21. The method of claim 20, wherein the UV light at wavelengths between 335 nm and 349 nm has intracellular penetration into target cells leading to intracellular antimicrobial properties without causing UV induced DNA damage.

22. The method of claim 20, wherein the infectious condition is selected from the group consisting of a bacterial infection, a viral infection, a fungal infection, and combinations thereof.

\* \* \* \* \*